(12) United States Patent
Lin

(10) Patent No.: US 7,786,125 B2
(45) Date of Patent: Aug. 31, 2010

(54) NEUROPROTECTIVE SMALL ORGANIC MOLECULES, COMPOSITIONS AND USES OF RELATED THERETO

(76) Inventor: Leu-Fen H. Lin, 10 Stewart Pl., Unit 6BW, White Plains, NY (US) 10603

( * ) Notice: Subject to any disclaimer, the term of this patent is extended or adjusted under 35 U.S.C. 154(b) by 0 days.

(21) Appl. No.: 12/384,620

(22) Filed: Apr. 7, 2009

(65) Prior Publication Data

US 2009/0227790 A1    Sep. 10, 2009

Related U.S. Application Data

(63) Continuation of application No. 10/894,336, filed on Jul. 19, 2004, now Pat. No. 7,671,077.

(51) Int. Cl.
*A01N 51/00* (2006.01)
*A61K 31/655* (2006.01)
*A61K 31/497* (2006.01)
*C07D 419/00* (2006.01)
*C07D 401/00* (2006.01)
*C07D 417/00* (2006.01)

(52) U.S. Cl. .................... 514/253.1; 514/158; 544/368; 546/272.4; 546/276.7; 546/270.7; 546/270.1

(58) Field of Classification Search ................. 514/158, 514/253.1; 544/368; 546/272.4, 276.7, 270.7, 546/270.1
See application file for complete search history.

(56) References Cited

U.S. PATENT DOCUMENTS

2004/0175382 A1*  9/2004  Schafer ................... 424/145.1

FOREIGN PATENT DOCUMENTS

WO    WO 2005013914 A2  *  2/2005

OTHER PUBLICATIONS

Lin et al. Journal of Neurochemistry. Jun. 15, 2004, vol. 89, Issue 6, pp. 1387-1395.*

* cited by examiner

*Primary Examiner*—Shengjun Wang
*Assistant Examiner*—Samira Jean-Louis

(57) ABSTRACT

The present application is directed to therapeutic compounds, compositions, and methods for culturing neuronal cells and for preventing and the treatment of neurodegenerative diseases, such as Parkinson's disease and amyotrophic lateral sclerosis (ALS).

14 Claims, 36 Drawing Sheets

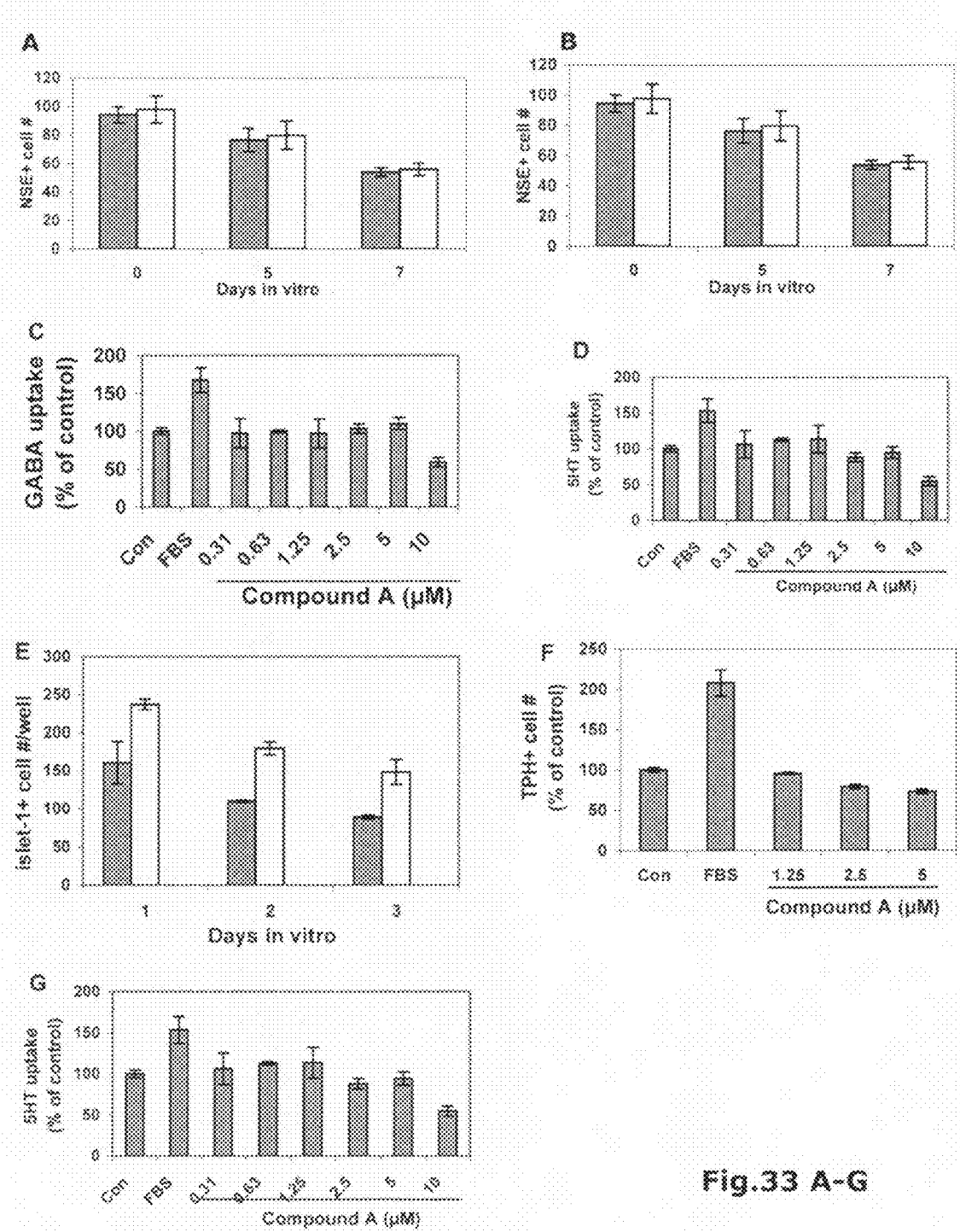
Fig.33 A-G

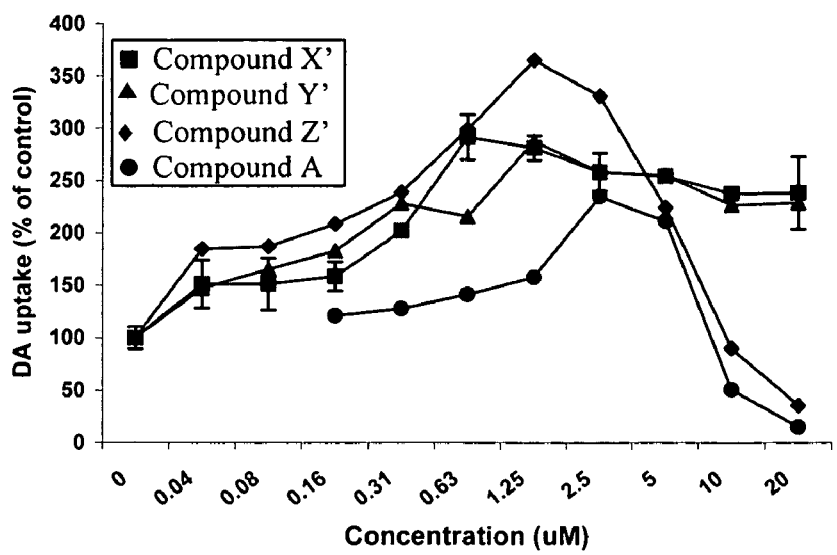
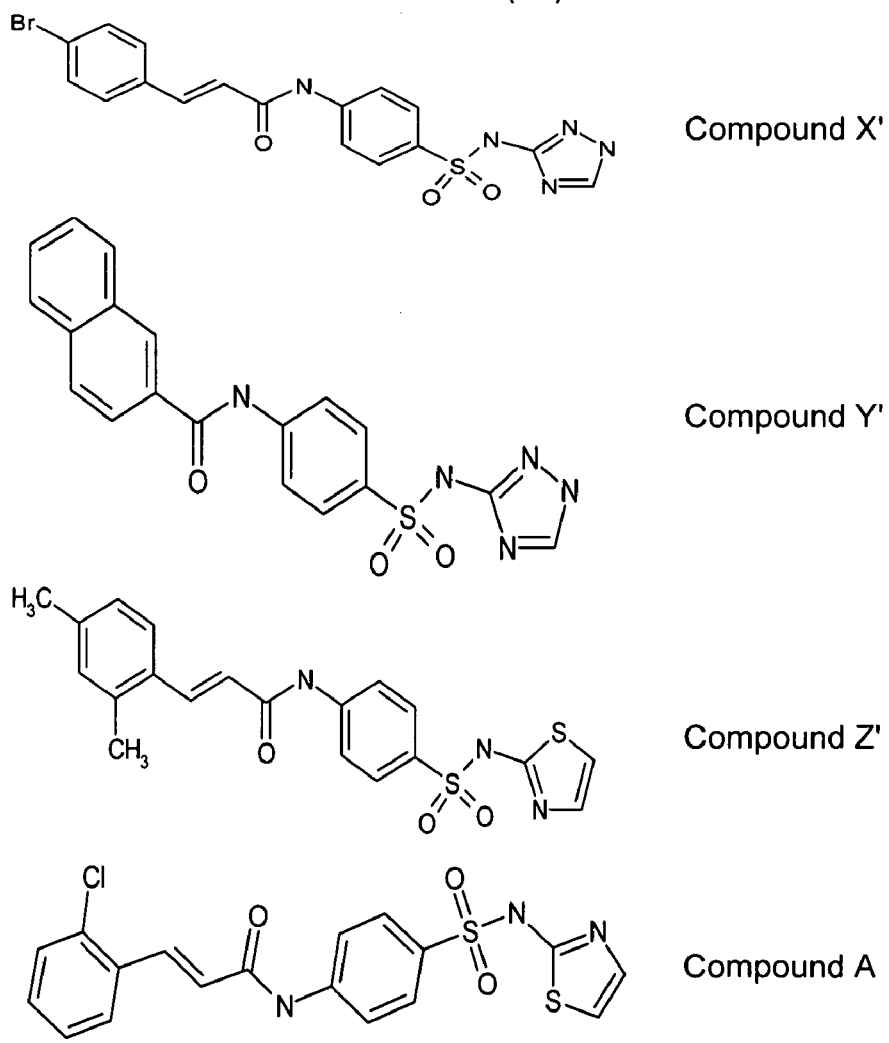
Fig. 36

NEUROPROTECTIVE SMALL ORGANIC MOLECULES, COMPOSITIONS AND USES OF RELATED THERETO

RELATED APPLICATION

This application is a continuation application of, and claims the benefit of, U.S. patent application Ser. No. 10/894,336, filed Jul. 19, 2004 now U.S. Pat. No. 7,671,077 entitled "Neuroprotective Small Organic Molecules, Compositions and Uses Related Thereto", the contents of which are incorporated by reference herein in their entirety. No new matter has been added.

BACKGROUND OF THE INVENTION

The individual symptoms of Parkinson's disease have been described by physicians from the time of Galen, but their occurrence as a syndrome was not recognized until 1817. In that year James Parkinson, a London physician, published an essay in which he argued that several different motor symptoms could be considered together as a group forming a distinctive condition. His observations are interesting not only because his conclusion was correct but also because he made his observations in part at a distance by watching the movements of Parkinsonian victims in the street of London. Parkinson's disease has been called at different times the shaking palsy or its Latin equivalent, paralysis agitans, but received its more common designation from Jean Charcot, who suggested that the disease be renamed to honor James Parkinson's recognition of its essential nature.

Parkinson's disease is fairly common, estimates of its incidence varying from 0.1 to 1.0% of the population. It is also of considerable interest for a number of other reasons. First, the disease seems related to the degeneration of the substantia nigra, and to the loss of the neurotransmitter substance dopamine, which is produced by cells of this region. The disease, therefore, provides an important insight into the role of this brainstem nucleus and its neurotransmitter in the control of movement. Second, because a variety of pharmacological treatments for Parkinson's disease relieve different features of its symptoms to some extent, the disease provides a model for understanding pharmacological treatments of motor disorders in their more general aspects. Third, although Parkinson's disease is described as a disease entity, the symptoms vary enormously among people, thus making manifest the complexity with which the components of movement are organized to produce fluid motion. Fourth, because many of the symptoms of Parkinson's disease strikingly resemble changes in motor activity that occur as a consequence of aging, the disease provides indirect insight into the more general problems of neural changes in aging.

There are three major types of Parkinson's disease: idiopathic, postencephalitic, and drug-induced. Parkinson's diseases may also result from arteriosclerosis, may follow poisoning by carbon monoxide or manganese intoxication, or may result from syphilis or the development of tumors. As is suggested by its name, the cause of idiopathic Parkinson's disease is not known. Its origin may be familiar, or it may be part of the aging process, but it is also widely thought that it might have a viral origin. It most often occurs in people who are over 50 years of age. The postencephalitic form originated in the sleeping sickness that appeared in the winter of 1916-1917 and vanished by 1927. Although the array of symptoms was bewilderingly varied, such that hardly any two patients seemed alike, Constantin von Economo demonstrated a unique pattern of brain damage associated with a virus infection in the brains of patients who had died from the disease. A third of those affected died in the acute stages of sleeping sickness in states either of coma or of sleeplessness. Although many people seemed to completely recover from the sickness, most subsequently developed neurological or psychiatric disorders and parkinsonism. The latency between the initial and subsequent occurrences of the disease has never been adequately explained. Searches for viral particles or virus-specific products in Parkinson patients have revealed no evidence of viral cause. The third major cause of Parkinson's disease is more recent, and is associated with ingestion of various drugs, particularly major tranquilizers that include reserpine and several phenothiazine and butyrophenone derivatives. The symptoms are usually reversible, but they are difficult to distinguish from those of the genuine disorder.

Recently it has been found that external agents can cause symptoms quite rapidly. Langston and coworkers have reported that a contaminant of synthetic heroin, MPTP, when taken by drug users is converted into $MPP^+$, which is extremely toxic to dopamine cells. A number of young drug users were found to display a complete parkinsonian syndrome after using contaminated drugs. This finding has suggested that other substances might cause similar effects. Demographic studies of patient admission in the cities of Vancouver and Helsinki show an increase in the incidence of patients getting the disease at ages younger than 40. This has raised the suggestion that water and air might contain environmental toxins that work in a fashion similar to MPTP.

Although Parkinsonian patients can be separated into clinical groups on the basis of cause of the disease, it is nevertheless likely that the mechanisms producing the symptoms have a common origin. Either the substantia nigra is damaged, as occurs in idiopathic and postencephalitic cases, or the activity of its cells is blocked or cells are killed, as occurs in drug-induced parkinsonism. The cells of the substantia nigra contain a dark pigment in Parkinson's disease that is depigmented by degeneration of the melatonin-containing neurons of the area. The cells of the substantia nigra are the point of origin of fibers that go to the basal ganglial frontal cortex and to the spinal cord. The neurotransmitter at the synapses of these projections is dopamine. It has been demonstrated by bioassay of the brains of deceased parkinsonian patients, and by analysis of the major metabolite of dopamine, homovanallic acid, which is excreted in the urine, that the amount of brain dopamine is reduced by over 90% and is often reduced to undetectable amounts. Thus, the cause of Parkinson's disease has been identified with some certainty as a lack of dopamine or, in drug-induced cases, with a lack of dopamine action.

Accordingly, pharmaceuticals and methods of treatment for treatment or prophylaxis of Parkinson's disease are needed.

SUMMARY OF THE INVENTION

One aspect of the present application relates to a method for promoting the survival of dopaminergic neurons or motoneurons by contacting the cells, in vitro or in vivo, with a compound as described herein in an amount effective to increase the rate of survival of the neurons relative to the absence of administration of the compound.

One aspect of the present application relates to a method for promoting the survival of neurons of the substantia nigra by contacting the cells, in vitro or in vivo, with a compound as described herein in an amount effective to increase the rate of survival of the neurons relative to the absence of administration of the compound.

In other embodiments, the subject method can be used for protecting dopaminergic neurons and/or motoneurons of a mammal from neurodegeneration, for preventing or treating neurodegenerative disorder, for treatment of Parkinson's disease, and/or for treatment of motoneuron diseases such as amyotrophic lateral sclerosis (ALS).

BRIEF DESCRIPTION OF THE DRAWINGS

FIG. 33 illustrates the Selectivity of compound A in cultures of midbrain (A-E) and hindbrain (F, G). All treatments were initiated at the time of plating. Where indicated, data represent percent of untreated control (Con). (A) Compound A does not increase total number of $NSE^+$ cells. Cultures were left untreated (solid bars) or treated with 2.5 µM compound A (open bars), fixed at DIV 0 (1 hr), 5 or 7, and stained with anti-NSE. (B) Unlike forskolin (Fk), compound A does not affect $GFAP^+$ cell number. Cultures were treated with compound A or 25 µM Fk, and stained with anti-GFAP at DIV 7. (C, D) Addition of compound A does not lead to an increase in GABA or 5-HT uptake. Cells were treated with fetal bovine serum (FBS, 2% as positive control) or compound A. Uptake was measured at DIV 8. (F) Compound A treatment does produce an increase in islet-$1^+$ cell numbers. Cultures were left untreated (solid bars) or treated with 2.5 µM compound A (open bars), stained with islet-1 at DIV 1, 2, and 3. *$p<0.05$ versus corresponding untreated cultures (solid bar); $p<0.05$ between DIV, two-way ANOVA test. (F, G) Compound A treatment does not change either the number of $TPH^+$ cells nor the amount of serotonin uptake in hindbrain cultures. Cells were treated with FBS (2% as positive control) or compound A, stained with anti-TPH at DIV 13 and counted (F). 5-HT uptake was measured at DIV 8 (G). All data represent averages (n=2) with SD shown in error bars.

FIG. 36 illustrates the effects of compounds X', Y' and Z' on dopamine uptake as compared to compound A. Each data point is the average of duplicate assays. SDs are within 15% and are shown in error bars in compound X' only. The 3 analogs all show significant differences ($p<0.05$ versus untreated control) at concentrations 0.16 µM and up. Compound Z' also shows $p<0.05$ at 0.04 µM.

DETAILED DESCRIPTION OF THE INVENTION

Figure 1:
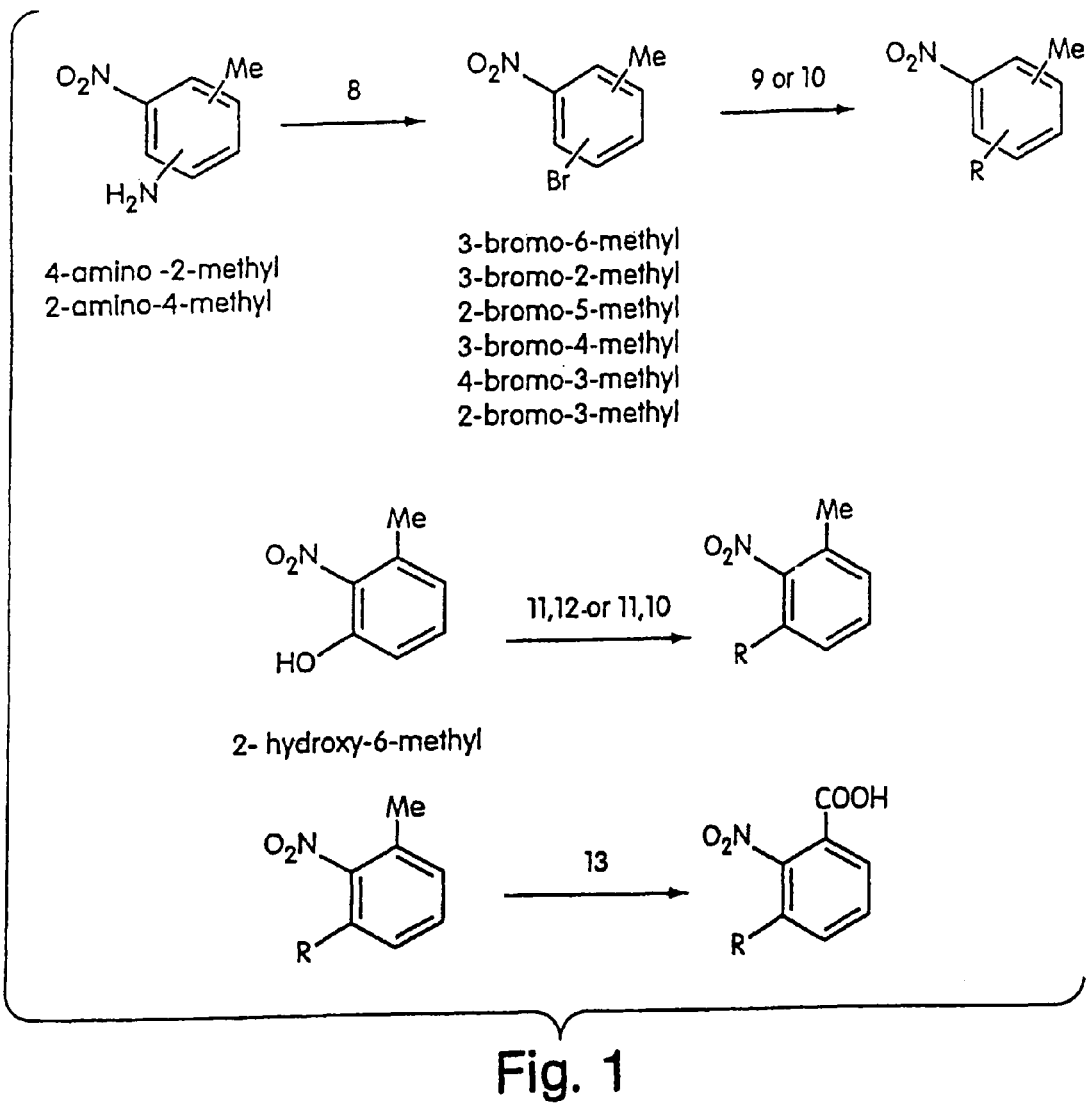
FIGS. 1-31 depict reactions useful for synthesizing compounds according to the present invention.
Figure 2:
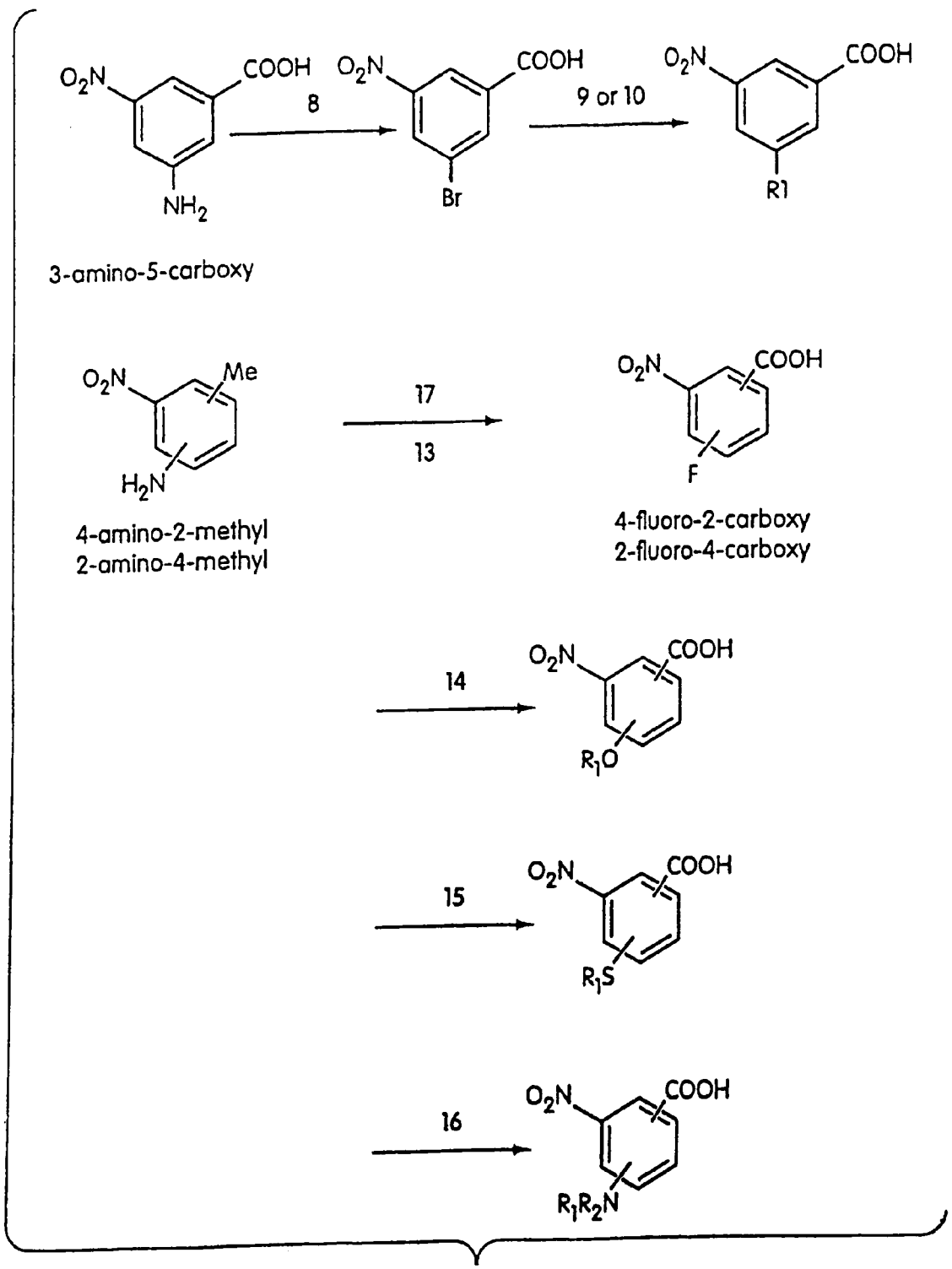
Figure 3:
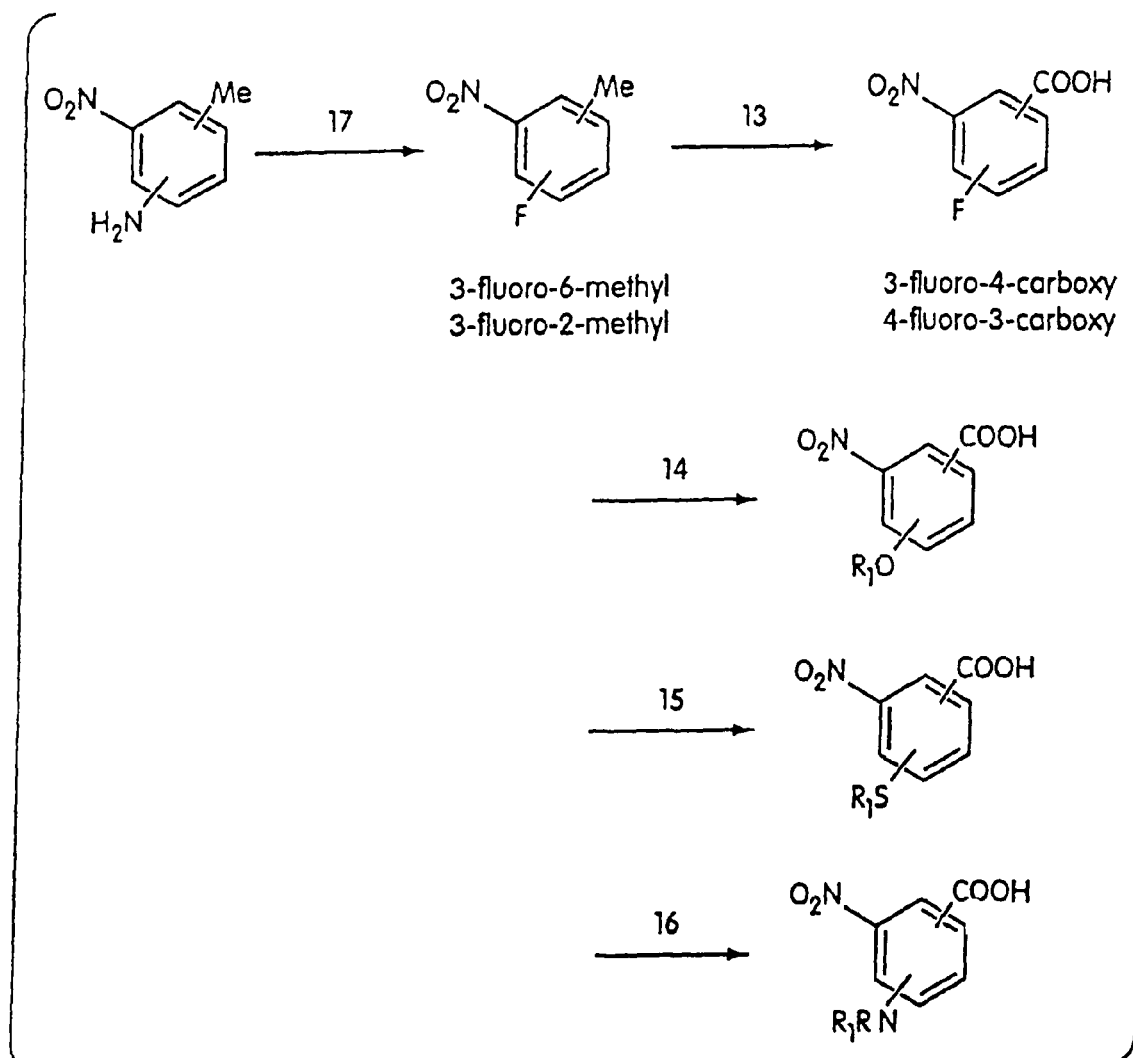
Figure 4:
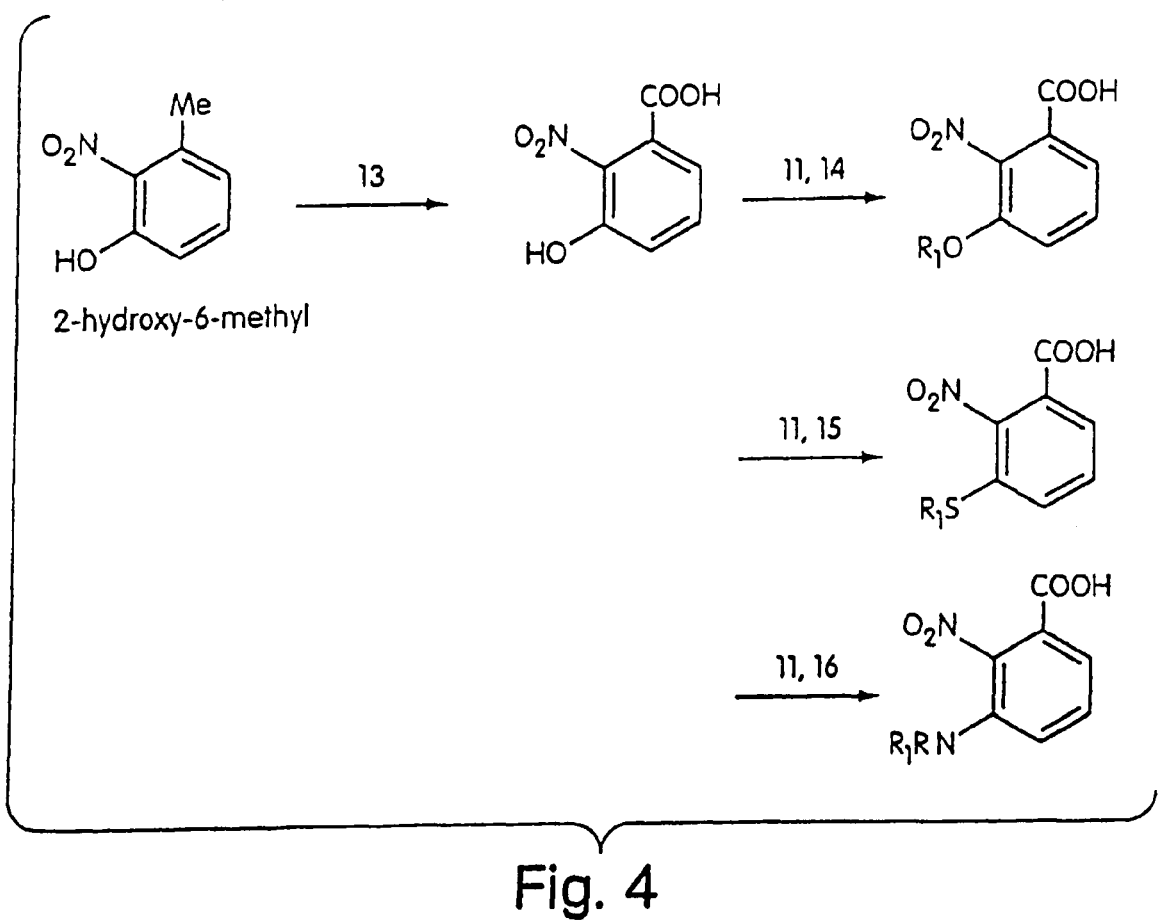
Figure 5:
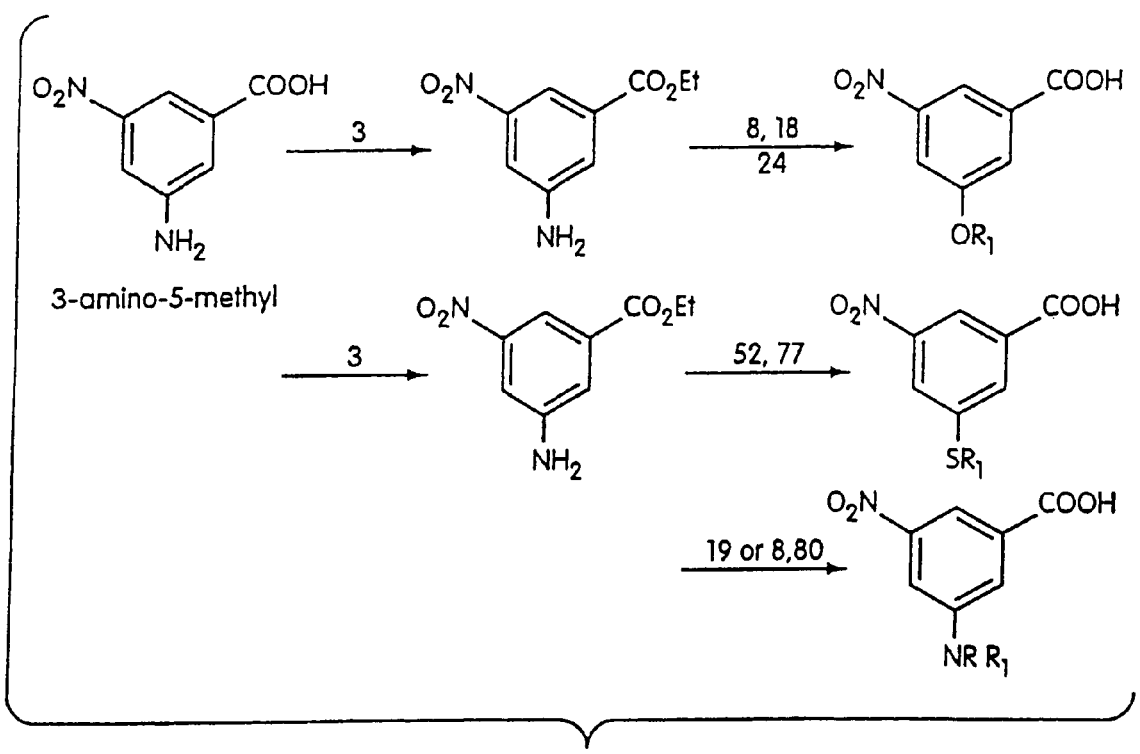
Figure 6:
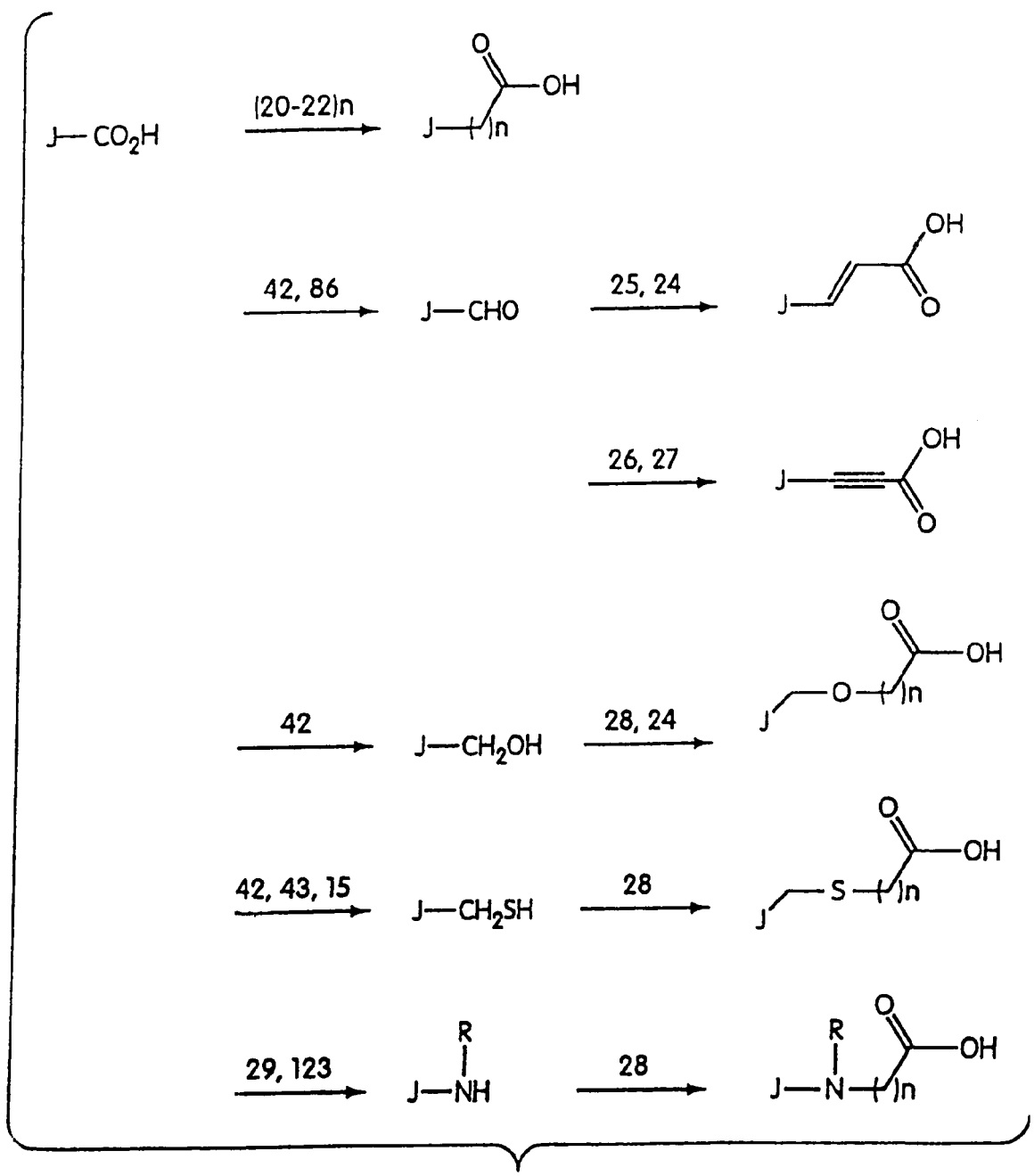
Figure 7:
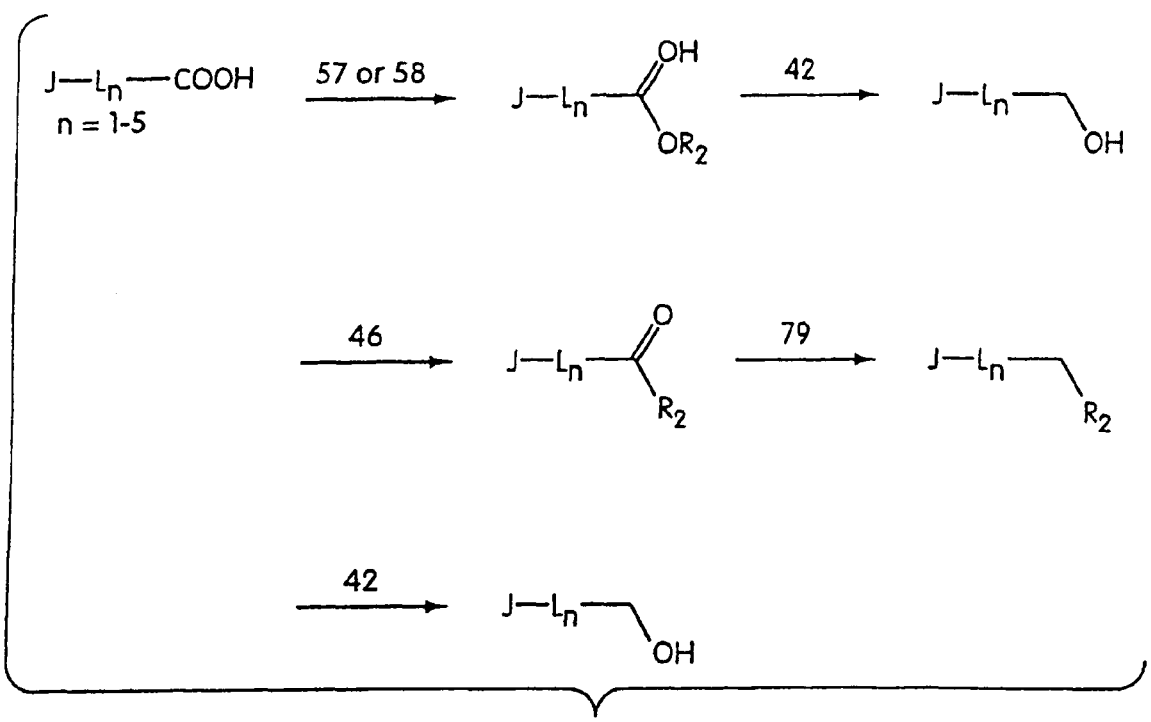
Figure 8:
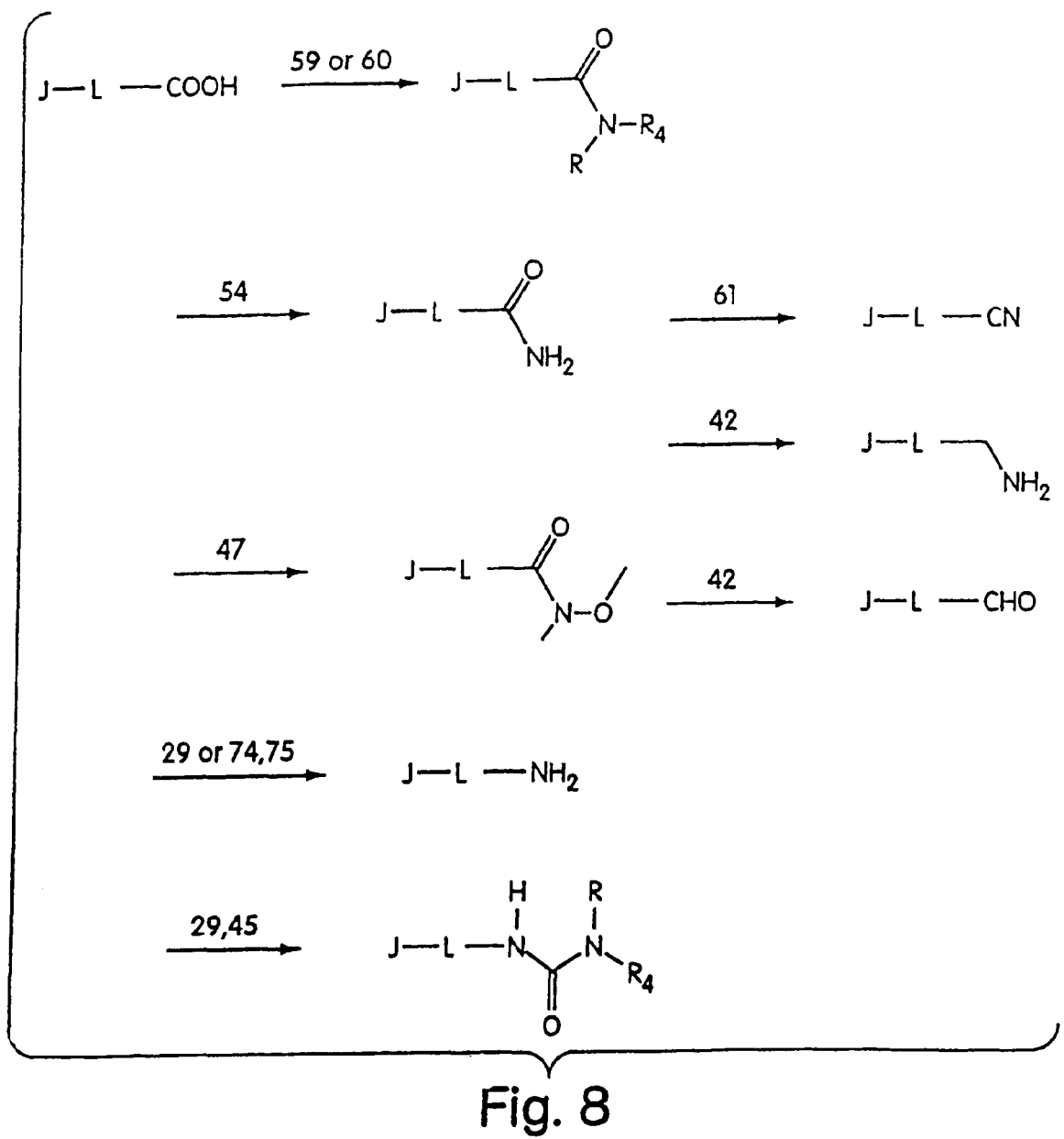
Figure 9:
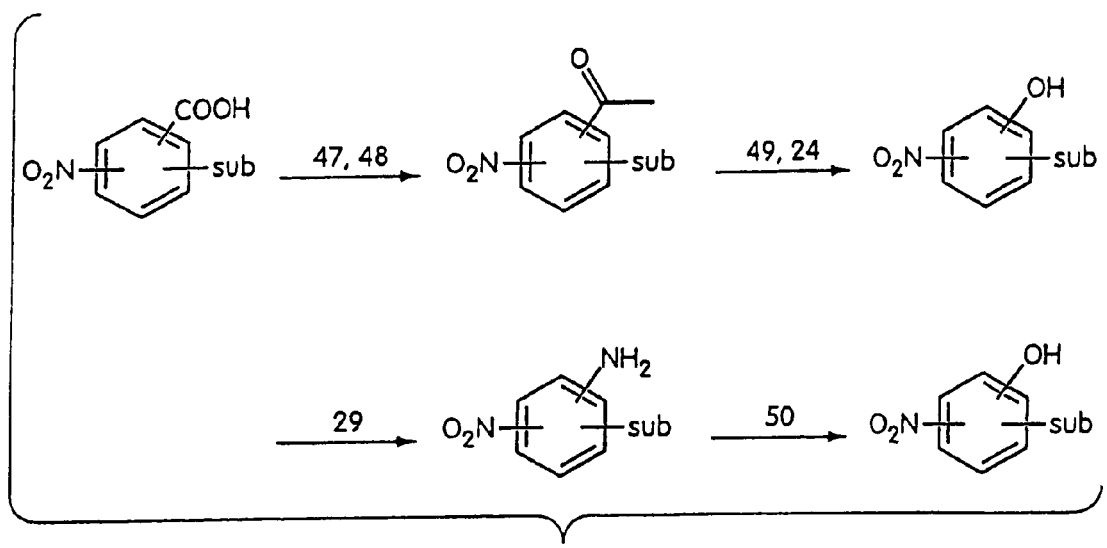
Figure 10:
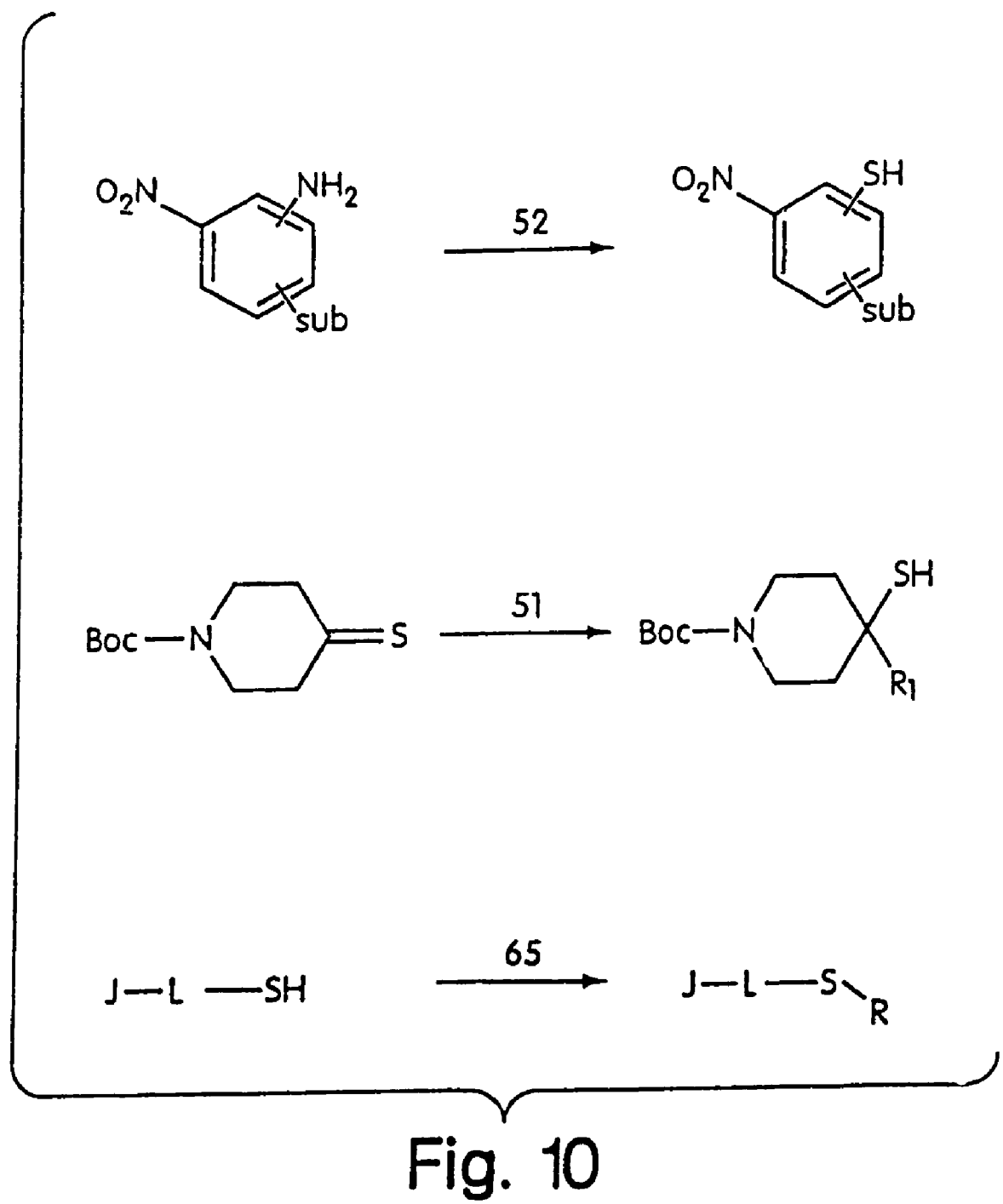
Figure 11:
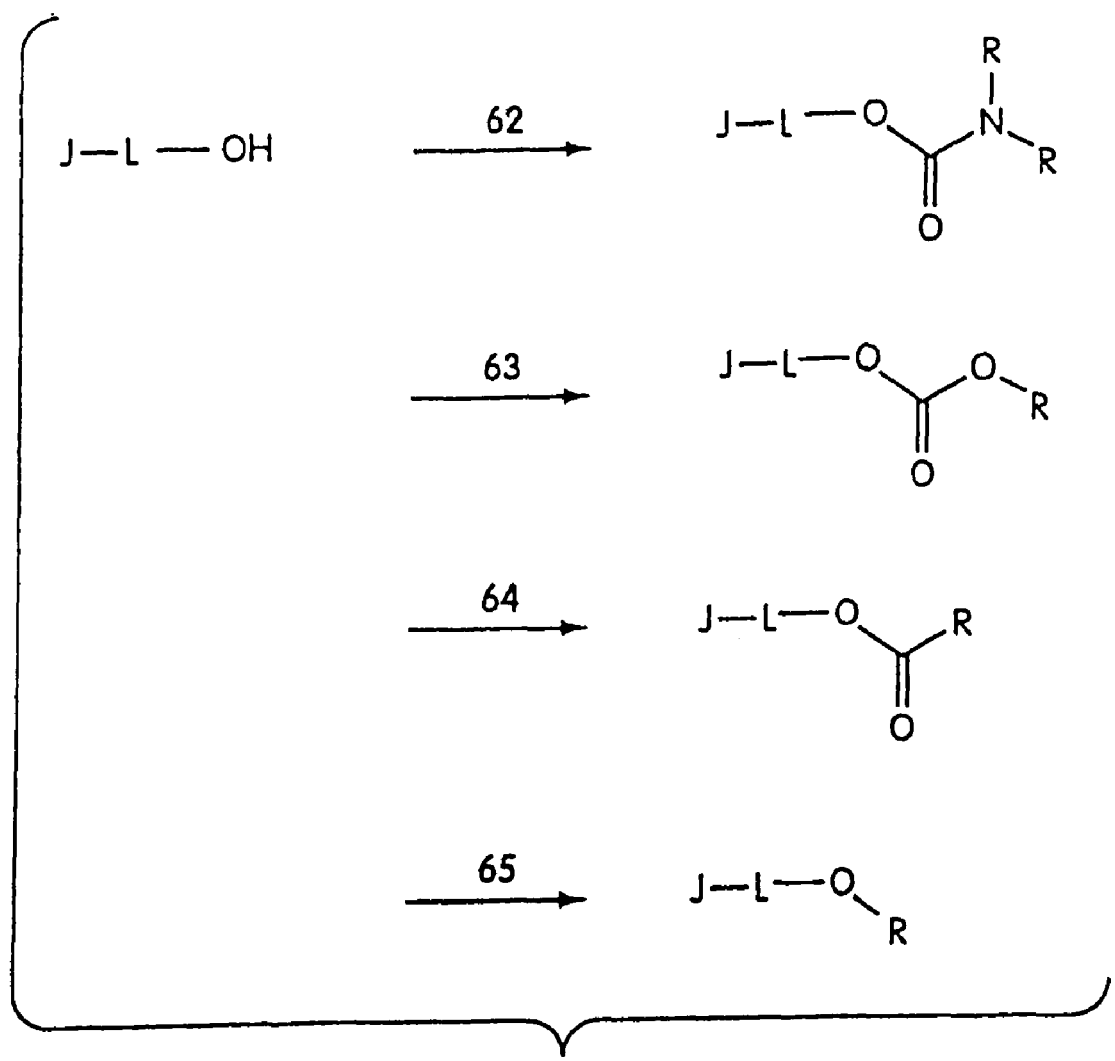
Figure 12:
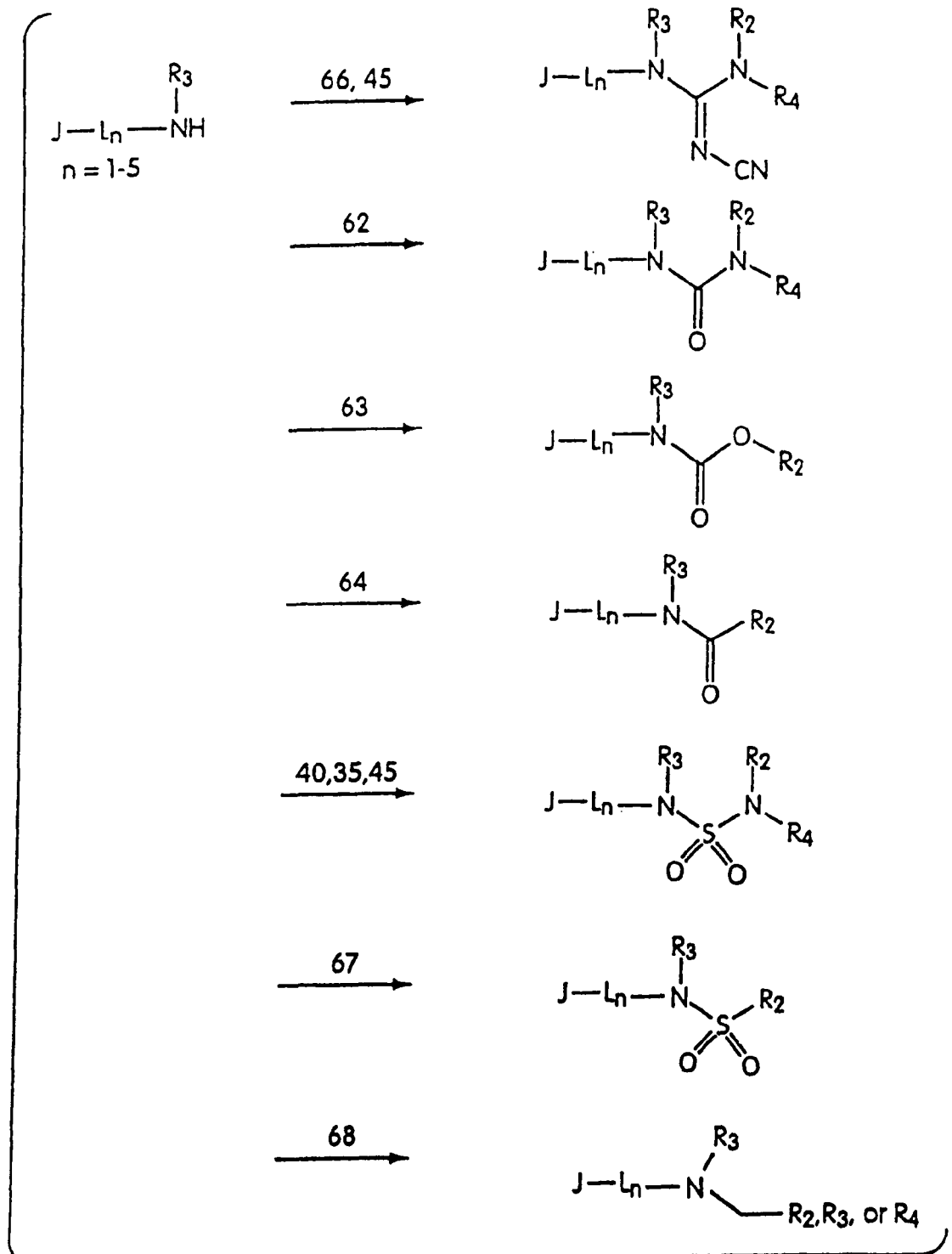
Figure 13:
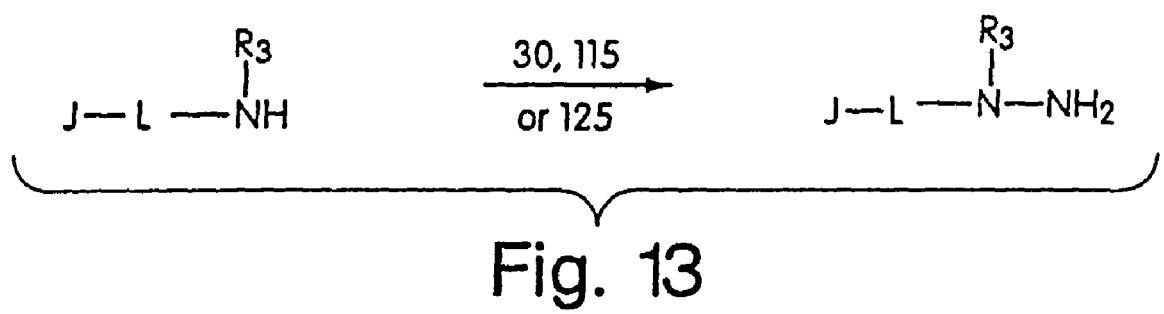
Figure 14:
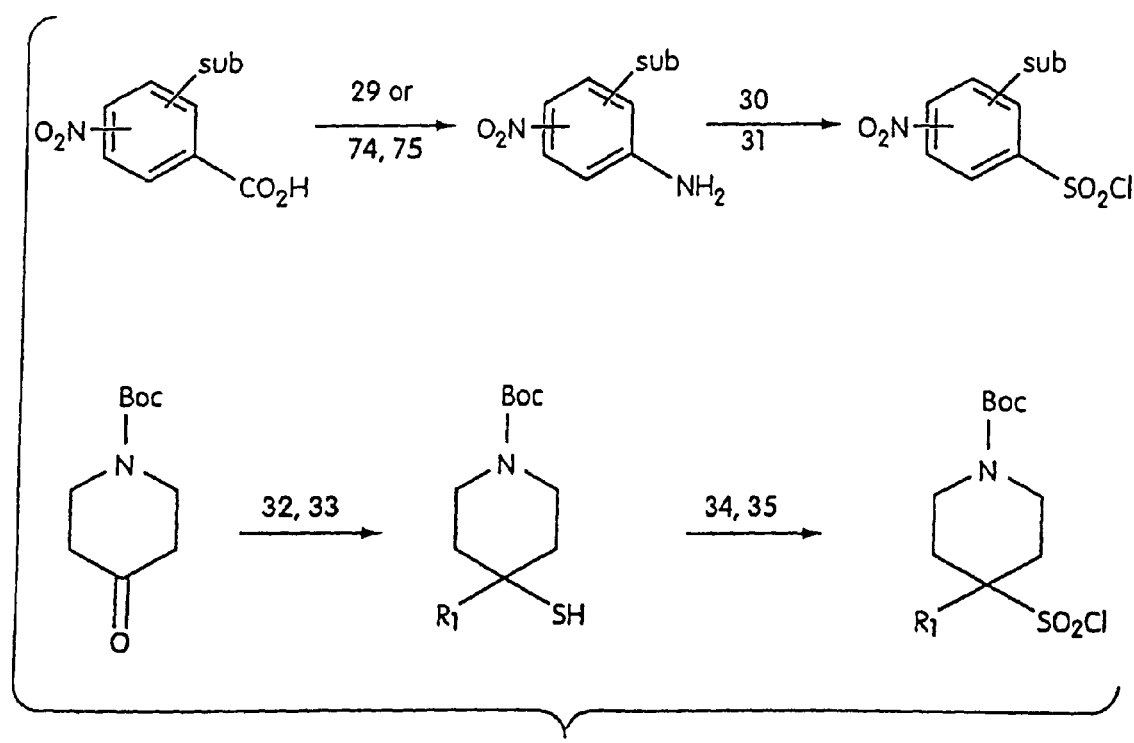
Figure 15:
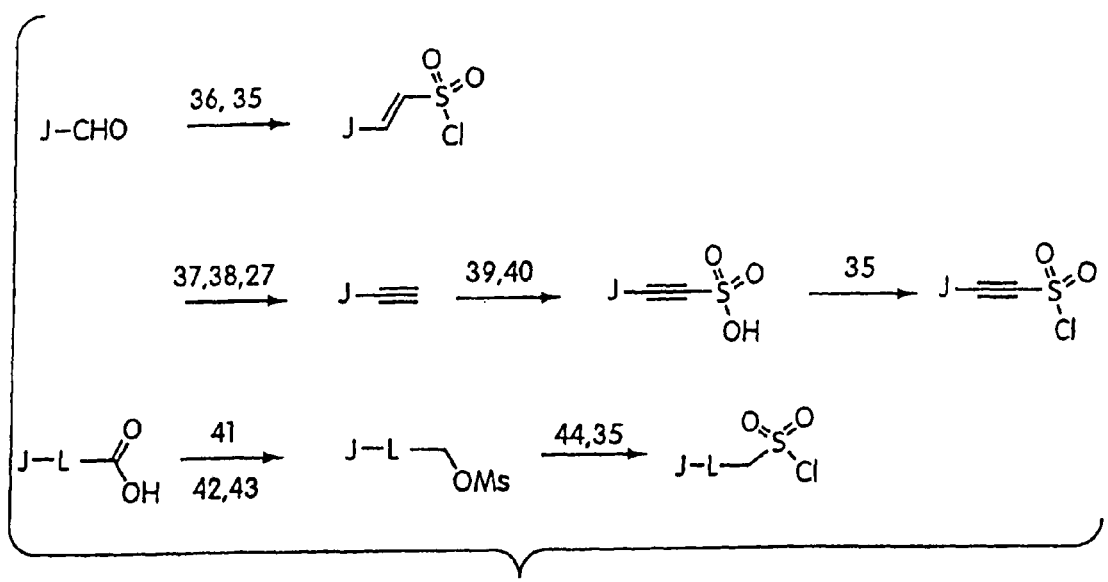
Figure 16:
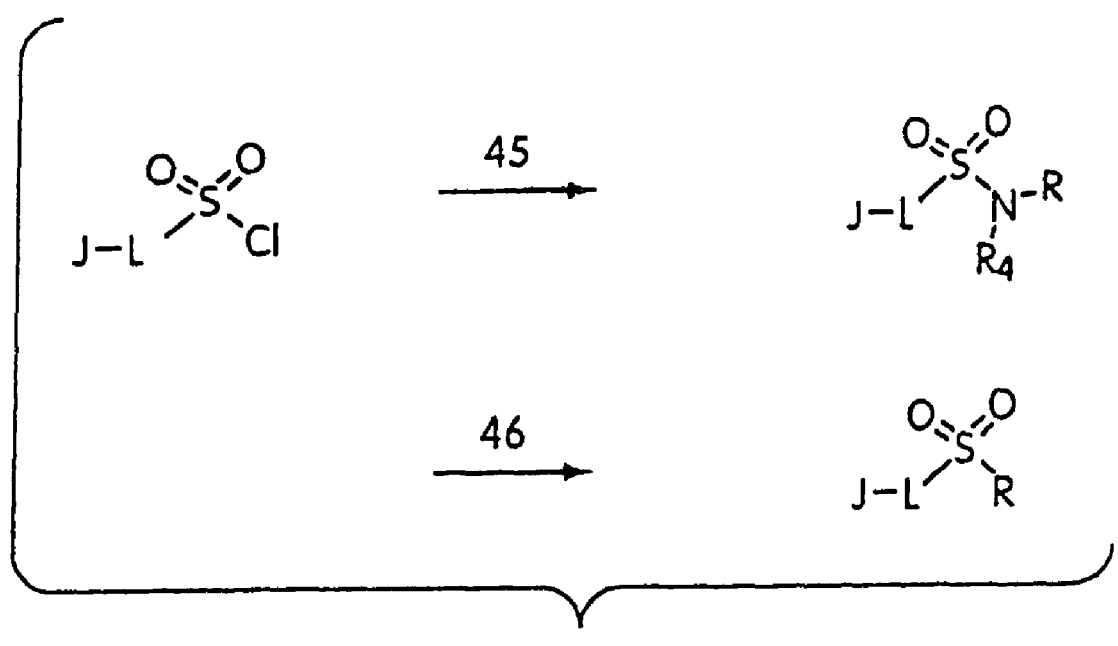
Figure 17:
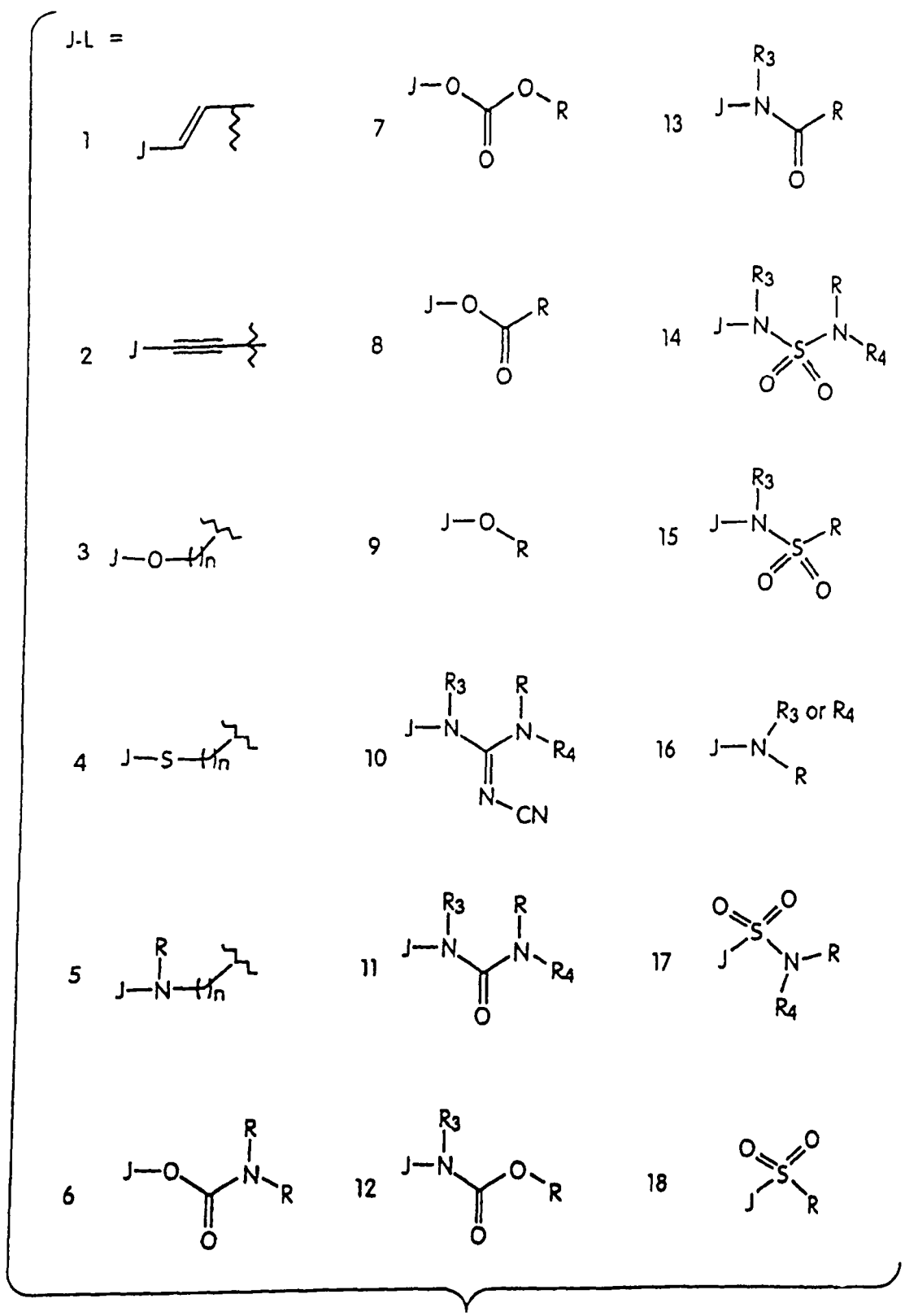
Figure 18:
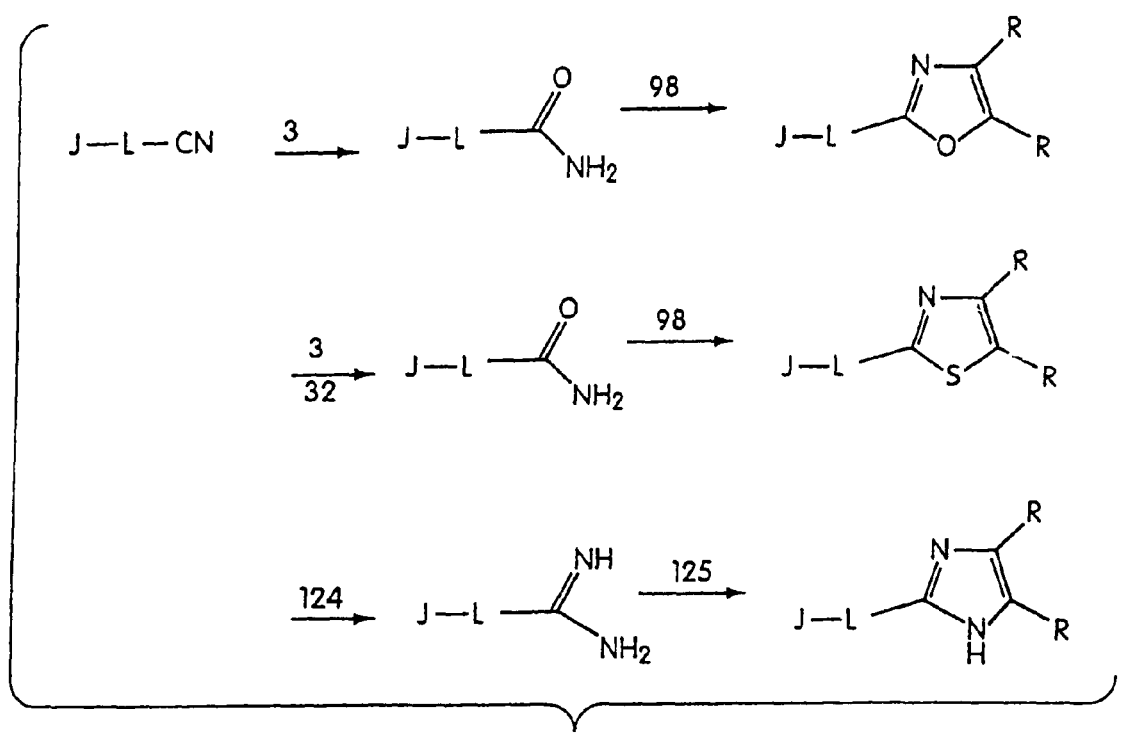
Figure 19:
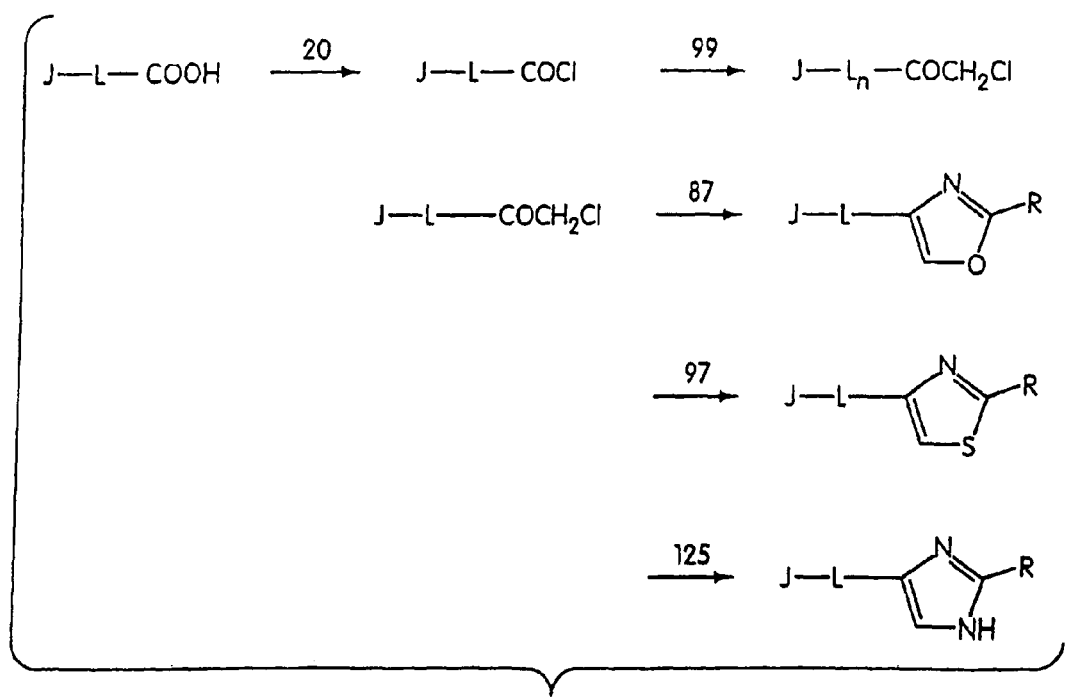
Figure 20:
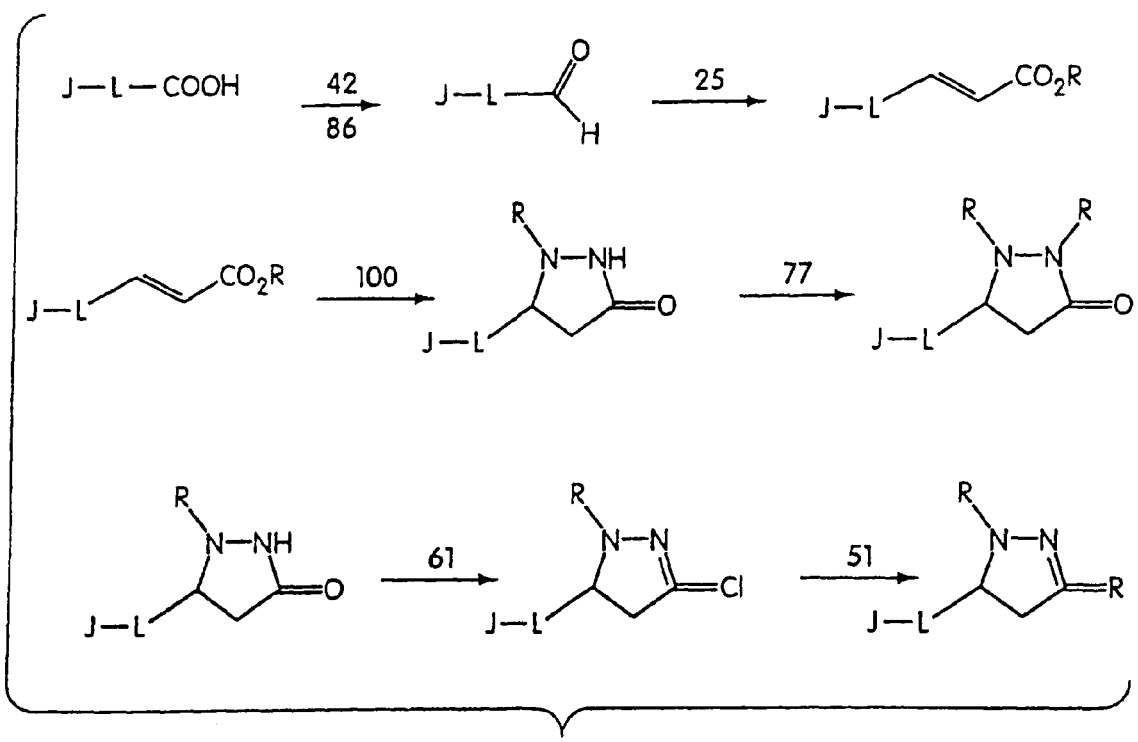
Figure 21:
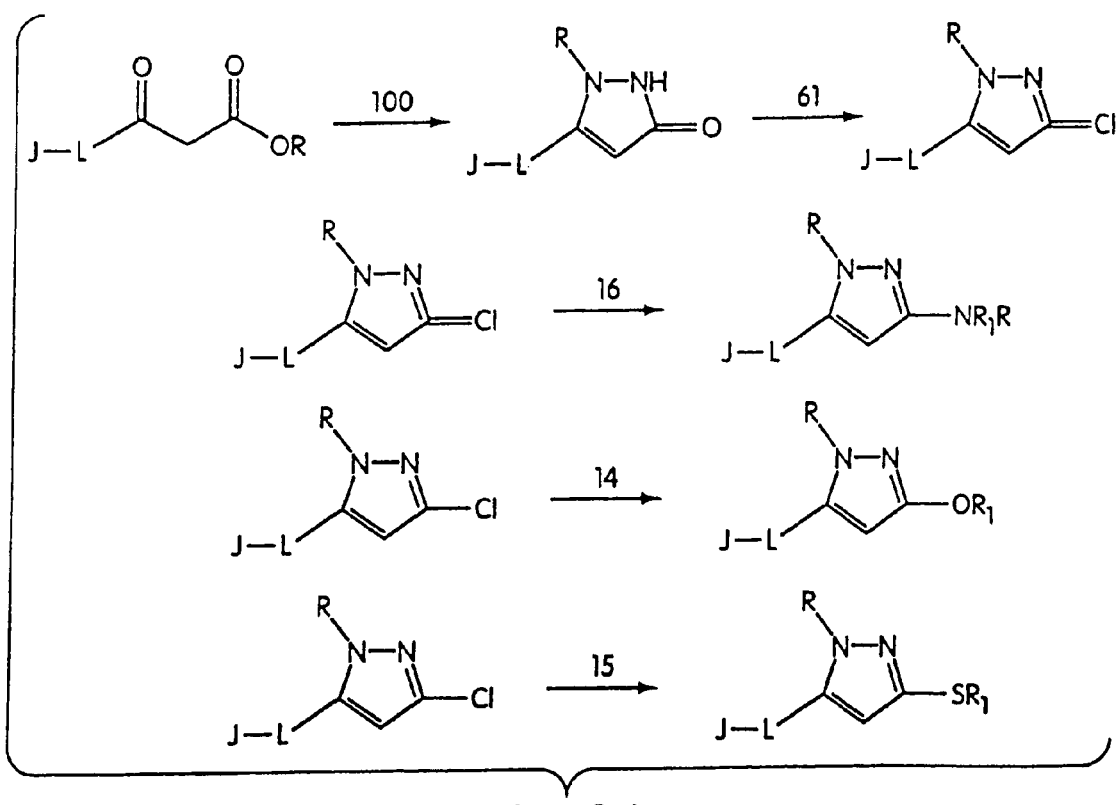
Figure 22:
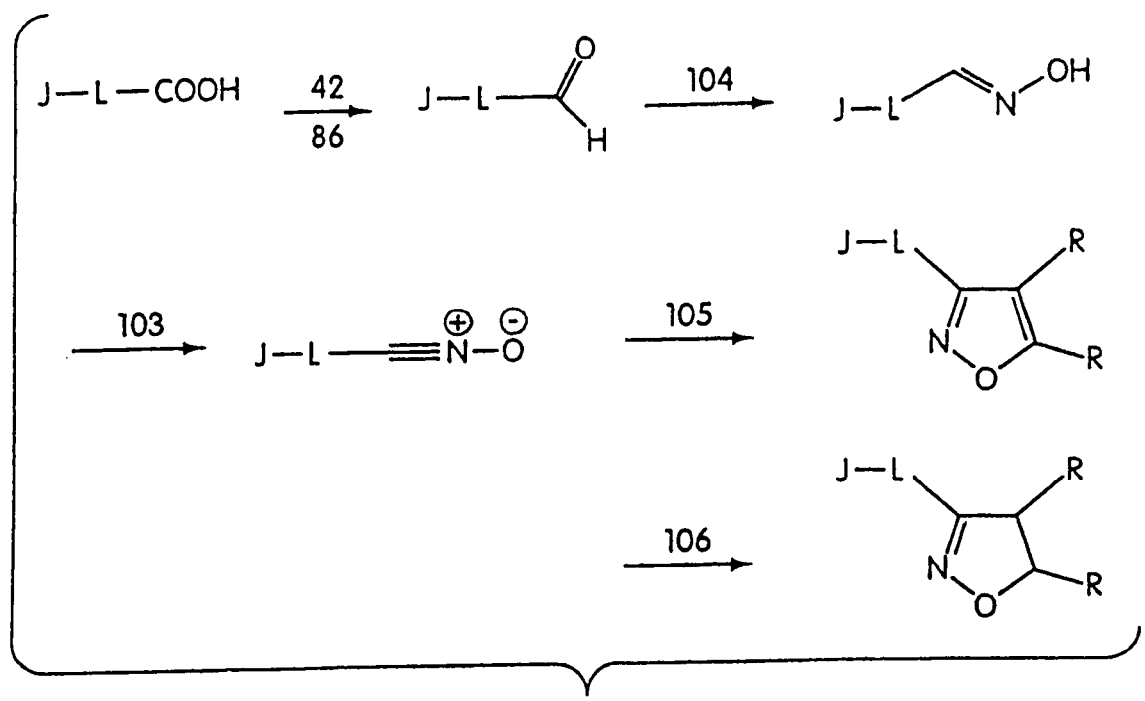
Figure 23:
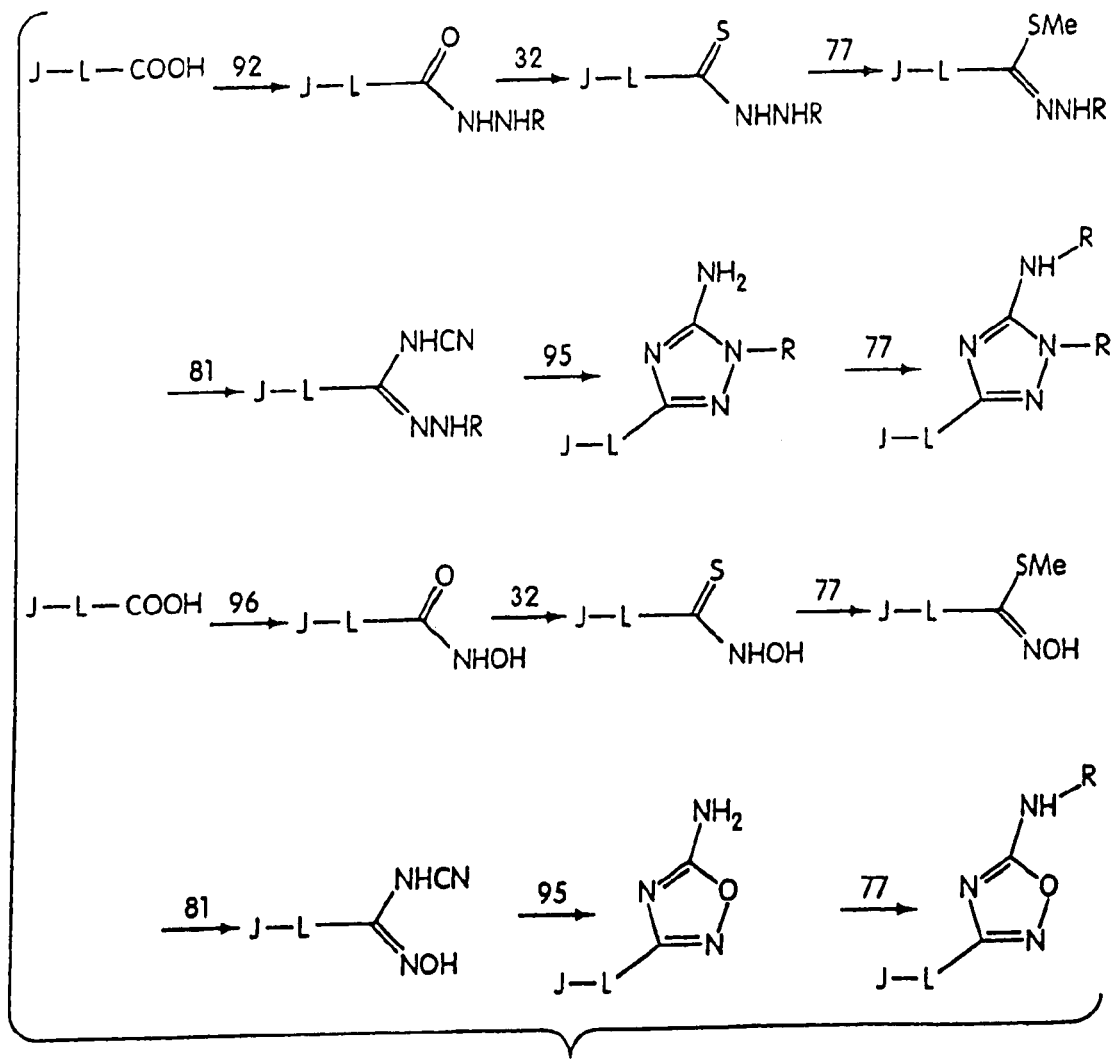
Figure 24:
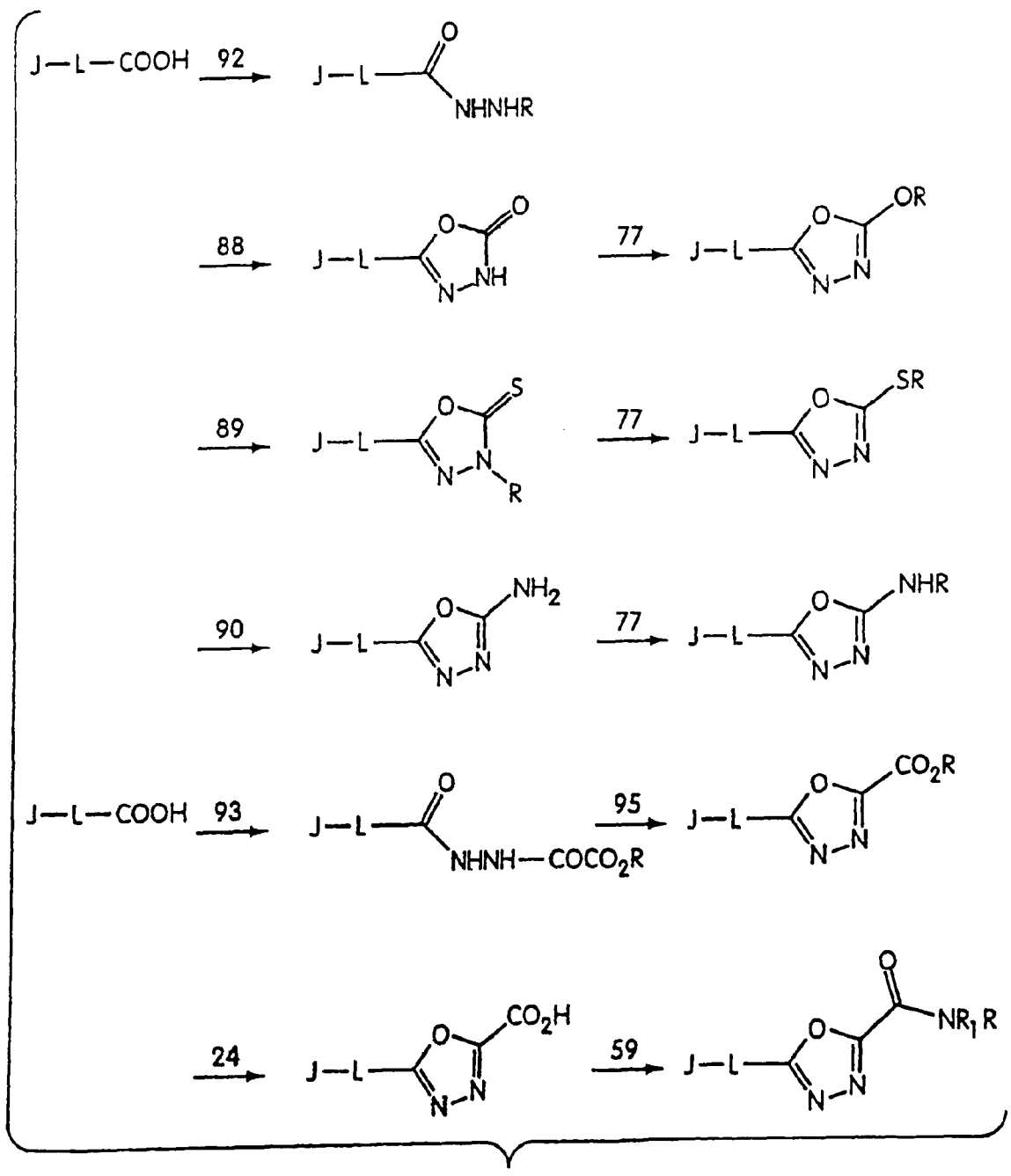
Figure 25:
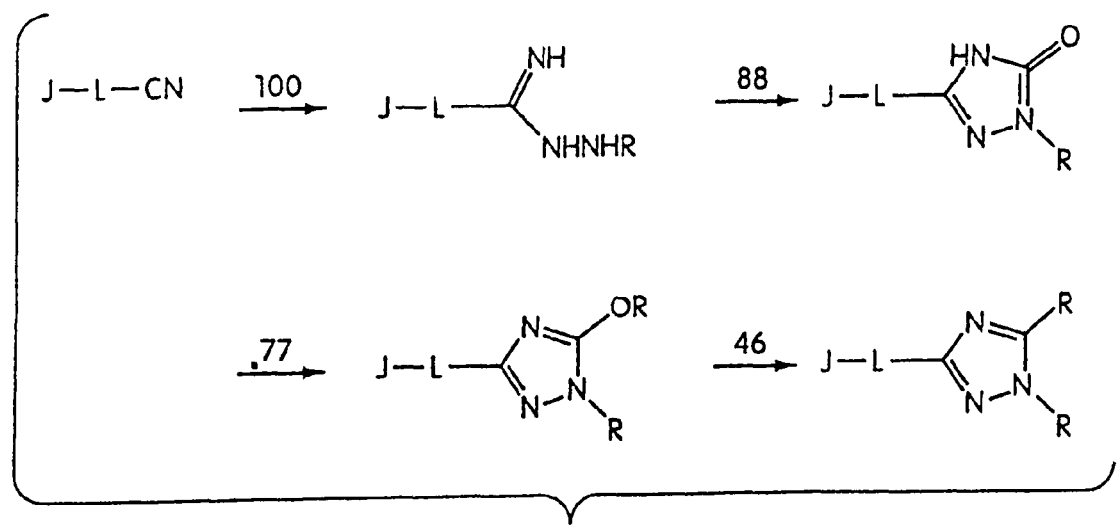
Figure 26:
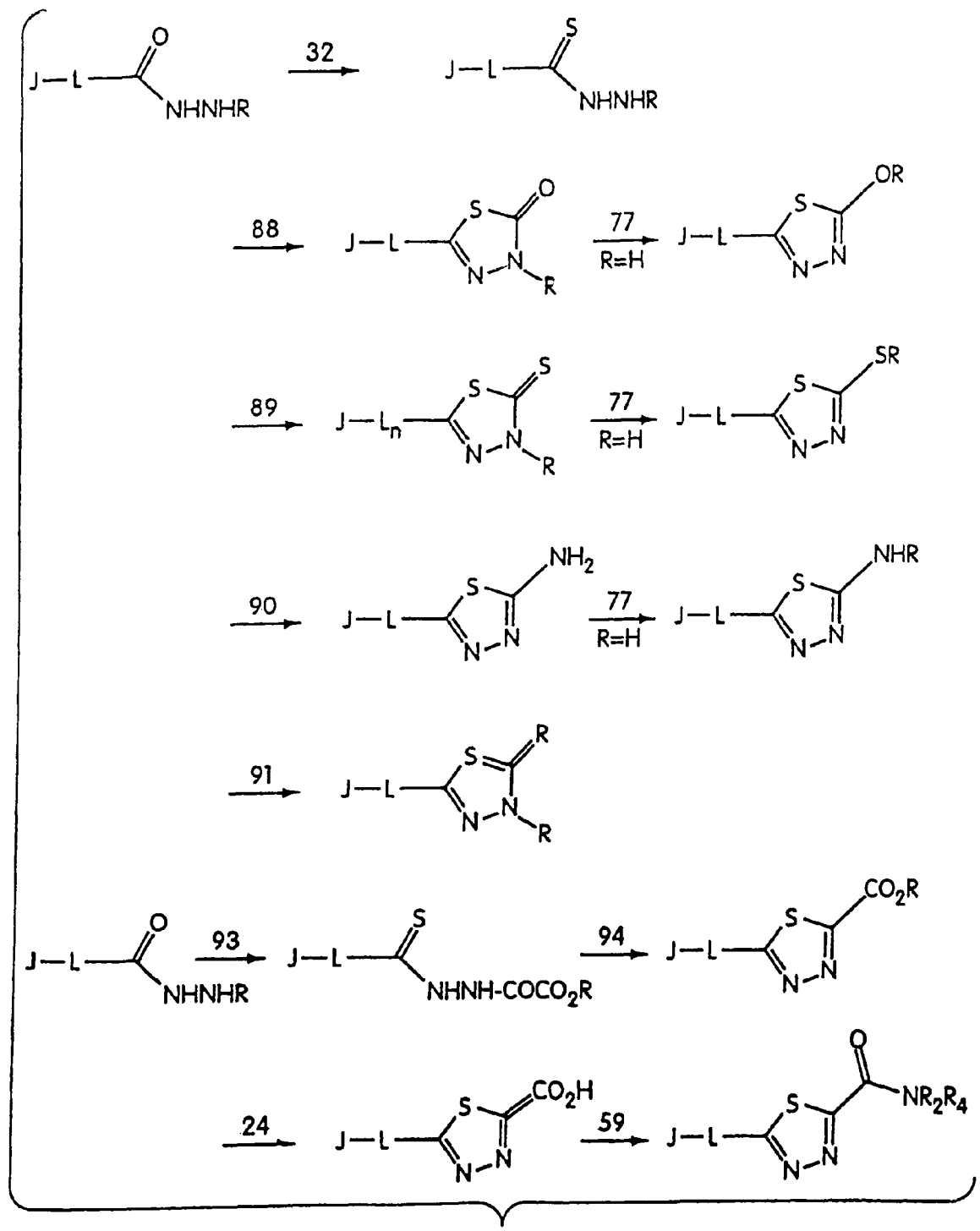
Figure 27:
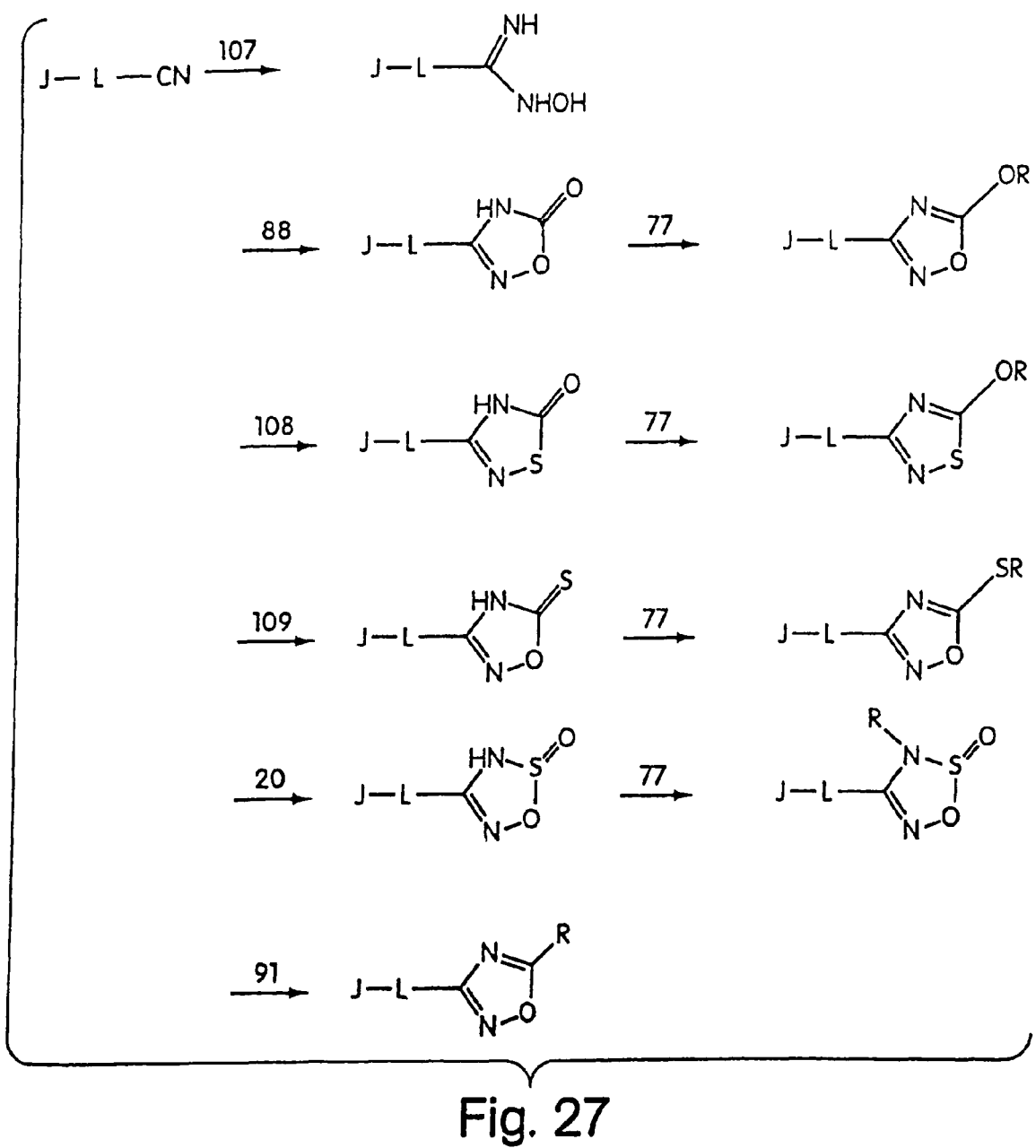
Figure 28:
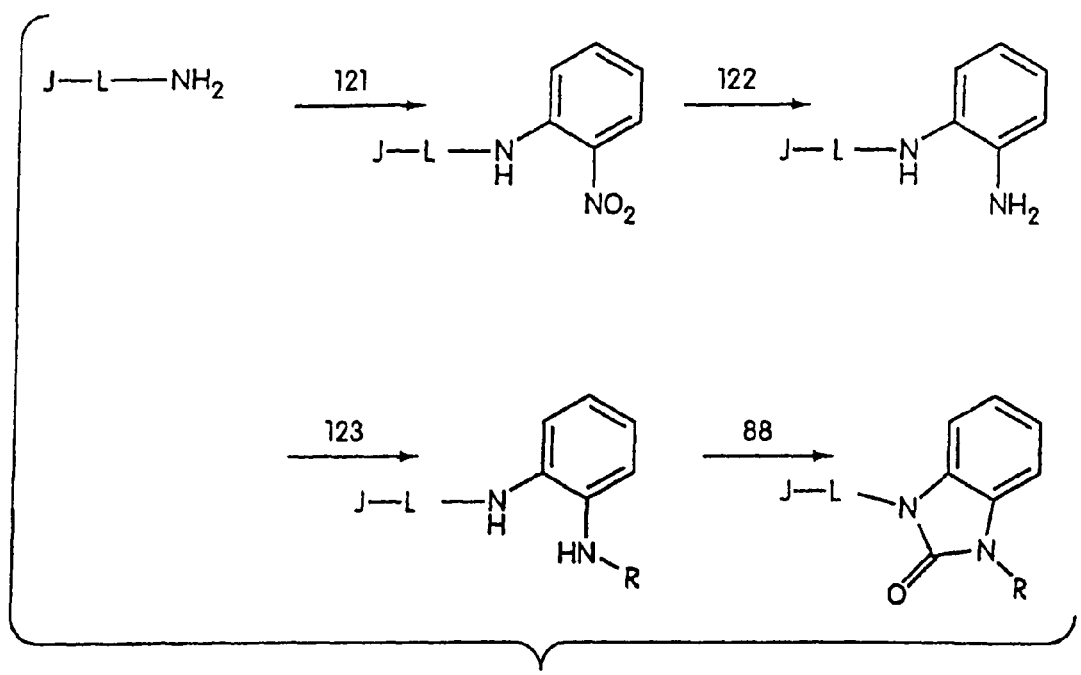
Figure 29:
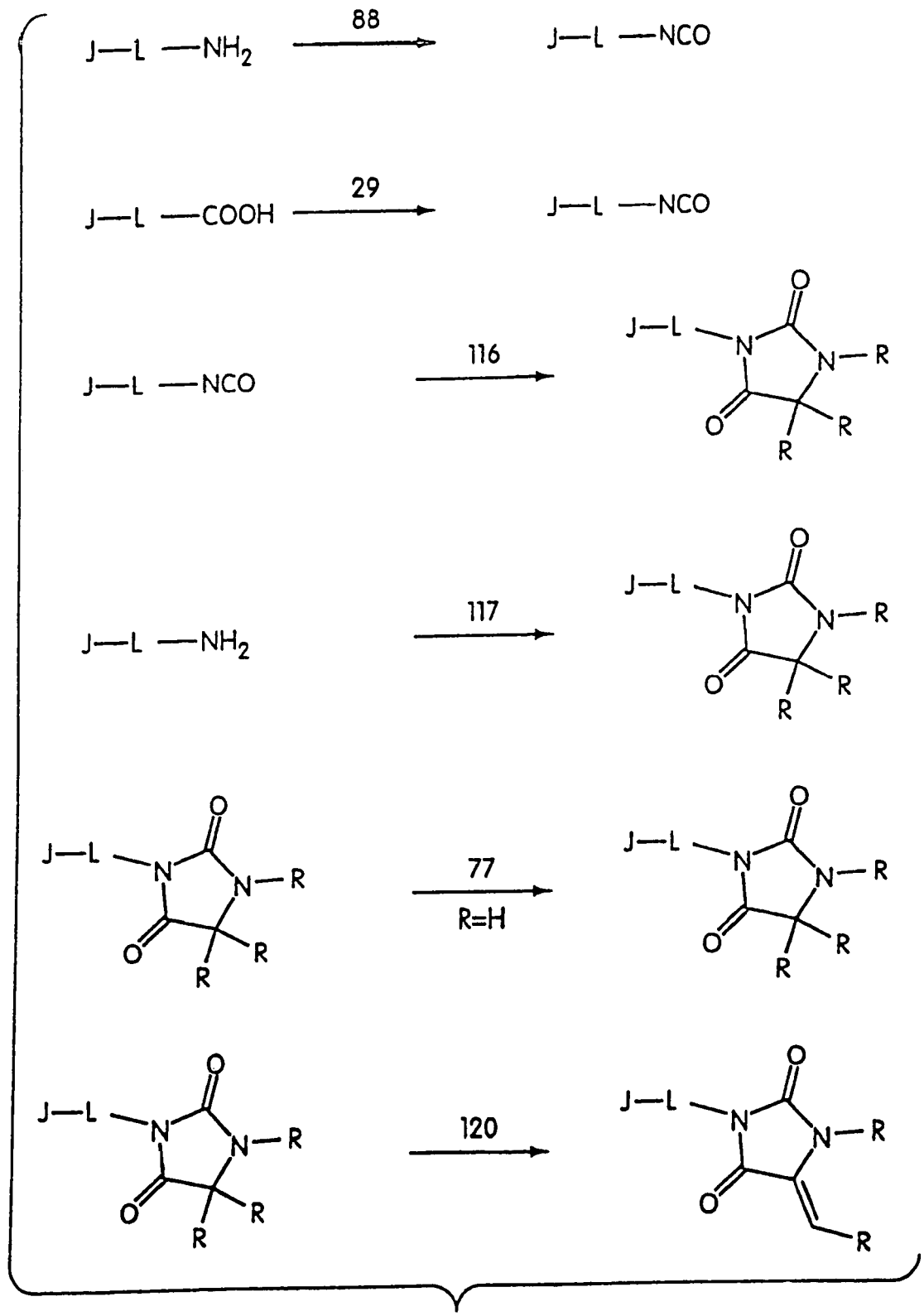
Figure 30:
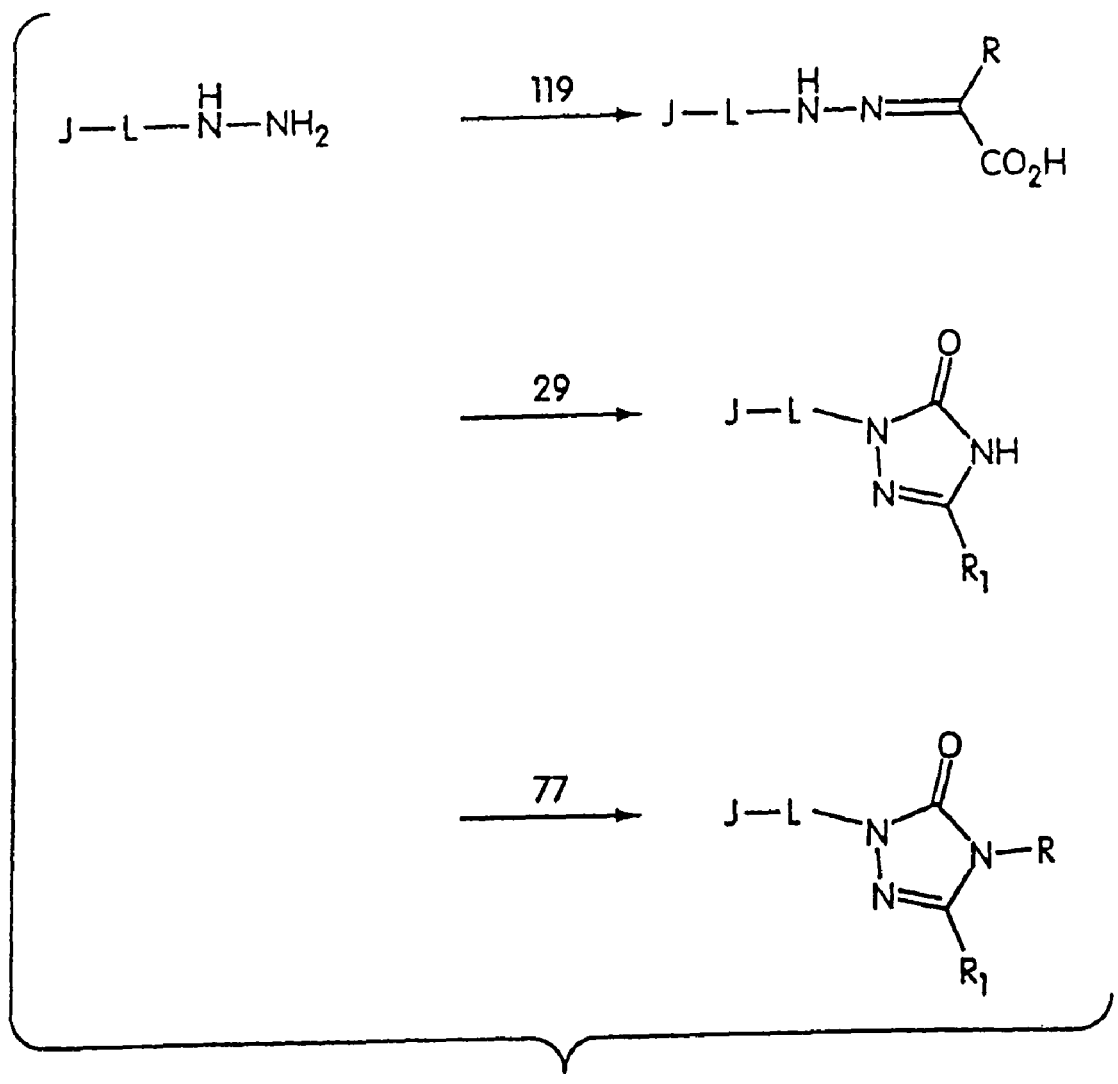
Figure 31:
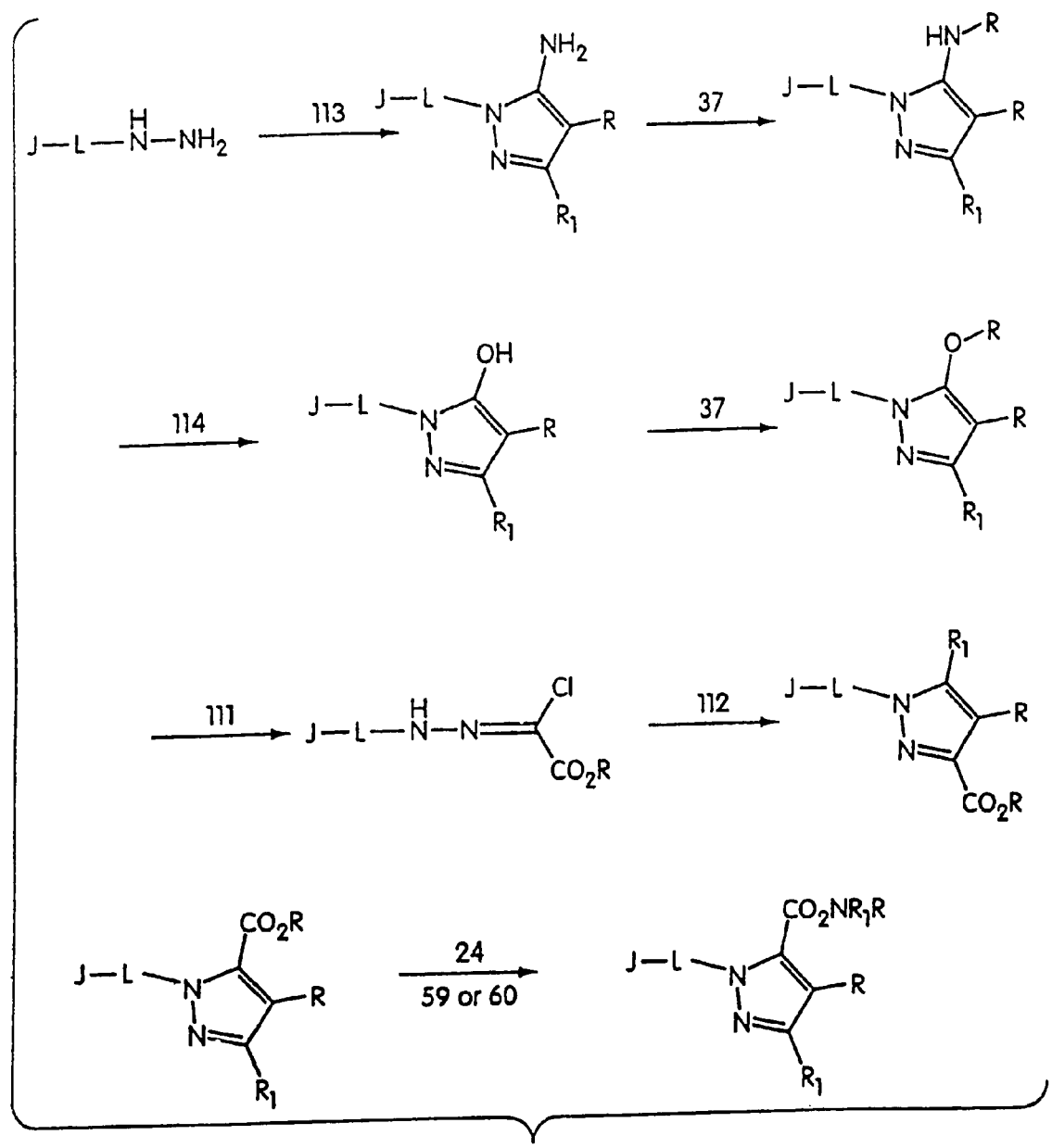

The subject compounds, as described in detail below, are useful as protective agents in the treatment and prophylaxis of neurodegenerative disorders, particularly those resulting from the loss of dopaminergic neurons and/or motoneurons, or the general loss tissue from the substantia nigra. As described with greater detail below, exemplary disorders ("candidate disorders") suitable for treatment with subject inhibitors include Parkinson's disease, amyotrophic lateral sclerosis (ALS) and the like. In terms of treatment, once a patient experiences symptoms of a candidate disorder, a goal of therapy is prevention of further loss of neuron function.

The subject invention also utilizes such compounds as cell culture additives for the maintenance of differentiated neurons in cultures, e.g., in cultures of dopaminergic neurons and motoneurons. The subject methods and compositions can also be used to augment the implantation of such neuronal cells in an animal.

I. Overview

The present application is directed to compositions and methods for the treatment and prophylaxis of neurodegenerative disorders, particularly those resulting from the loss of dopaminergic neurons and/or motoneurons, or the general loss tissue from the substantia nigra. The subject methods are effective on both human and animal subjects afflicted with these conditions. Animal subjects include both domestic animals and livestock, raised either as pets or for commercial purposes, such as dogs, cats, cattle, horses, sheep, hogs, and goats.

II. Definitions

For convenience, certain terms employed in the specification, examples, and appended claims are collected here.

The term "$ED_{50}$" means the dose of a drug that produces 50% of its maximum response or effect.

An "effective amount" of a subject compound, with respect to the subject method of treatment, refers to an amount of the therapeutic in a preparation which, when applied as part of a desired dosage regimen causes a increase in survival of a neuronal cell population according to clinically acceptable standards for the treatment or prophylaxis of a particular disorder.

The term "$LD_{50}$" means the dose of a drug that is lethal in 50% of test subjects.

A "patient" or "subject" to be treated by the subject method are mammals, including humans.

By "prevent degeneration" it is meant reduction in the loss of cells (such as from apoptosis), or reduction in impairment of cell function, e.g., release of dopamine in the case of dopaminergic neurons. Generally, as used herein, a therapeutic that "prevents" a disorder or condition refers to a compound that, in a sample, reduces the occurrence of the disorder or condition in the sample, relative to an untreated control sample, or delays the onset of one or more symptoms of the disorder or condition.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

The term "therapeutic index" refers to the therapeutic index of a drug defined as $LD_{50}/ED_{50}$.

A "trophic factor" is a molecule that directly or indirectly affects the survival or function of a neuronal cell, e.g., a dopaminergic cell or motoneuron.

A "trophic amount" of a subject compound is an amount sufficient to, under the circumstances, cause an increase in the rate of survival or the functional performance of a neuronal cell, e.g., a dopaminergic neuron or motoneuron.

'Acyl' refers to a group suitable for acylating a nitrogen atom to form an amide or carbamate, a carbon atom to form a ketone, a sulfur atom to form a thioester, or an oxygen atom to form an ester group, e.g., a hydrocarbon attached to a —C(=O)— moiety. Preferred acyl groups include benzoyl, acetyl, tert-butyl acetyl, pivaloyl, and trifluoroacetyl. More preferred acyl groups include acetyl and benzoyl. The most preferred acyl group is acetyl.

The term 'acylamino' is art-recognized and preferably refers to a moiety that can be represented by the general formula:

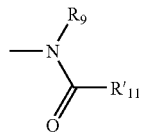

wherein $R_9$ and $R'_{11}$ each independently represent hydrogen or a hydrocarbon substituent, such as alkyl, heteroalkyl, aryl, heteroaryl, carbocyclic aliphatic, and heterocyclic aliphatic.

The terms 'amine' and 'amino' are art-recognized and refer to both unsubstituted and substituted amines as well as ammonium salts, e.g., as can be represented by the general formula:

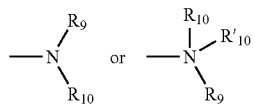

wherein $R_9$, $R_{10}$, and $R'_{10}$ each independently represent hydrogen or a hydrocarbon substituent, or $R_9$ and $R_{10}$ taken together with the N atom to which they are attached complete a heterocycle having from 4 to 8 atoms in the ring structure. In preferred embodiments, none of $R_9$, $R_{10}$, and $R'_{10}$ is acyl, e.g., $R_9$, $R_{10}$, and $R'_{10}$ are selected from hydrogen, alkyl, heteroalkyl, aryl, heteroaryl, carbocyclic aliphatic, and heterocyclic aliphatic. The term 'alkylamine' as used herein means an amine group, as defined above, having at least one substituted or unsubstituted alkyl attached thereto. Amino groups that are positively charged (e.g., $R'_{10}$ is present) are referred to as 'ammonium' groups. In amino groups other than ammonium groups, the amine is preferably basic, e.g., its conjugate acid has a $pK_a$ above 7.

The terms 'amido' and 'amide' are art-recognized as an amino-substituted carbonyl, such as a moiety that can be represented by the general formula:

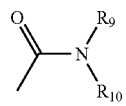

wherein $R_9$ and $R_{10}$ are as defined above. In certain embodiments, the amide will include imides.

'Alkyl' refers to a saturated or unsaturated hydrocarbon chain having 1 to 18 carbon atoms, preferably 1 to 12, more preferably 1 to 6, more preferably still 1 to 4 carbon atoms. Alkyl chains may be straight (e.g., n-butyl) or branched (e.g., sec-butyl, isobutyl, or t-butyl). Preferred branched alkyls have one or two branches, preferably one branch. Preferred alkyls are saturated. Unsaturated alkyls have one or more double bonds and/or one or more triple bonds. Preferred unsaturated alkyls have one or two double bonds or one triple bond, more preferably one double bond. Alkyl chains may be unsubstituted or substituted with from 1 to 4 substituents. Preferred alkyls are unsubstituted. Preferred substituted alkyls are mono-, di-, or trisubstituted. Preferred alkyl substituents include halo, haloalkyl, hydroxy, aryl (e.g., phenyl, tolyl, alkoxyphenyl, alkyloxycarbonylphenyl, halophenyl), heterocyclyl, and heteroaryl.

The terms 'alkenyl' and 'alkynyl' refer to unsaturated aliphatic groups analogous in length and possible substitution to the alkyls described above, but that contain at least one double or triple bond, respectively. When not otherwise indicated, the terms alkenyl and alkynyl preferably refer to lower alkenyl and lower alkynyl groups, respectively. When the term alkyl is present in a list with the terms alkenyl and alkynyl, the term alkyl refers to saturated alkyls exclusive of alkenyls and alkynyls.

The terms 'alkoxyl' and 'alkoxy' as used herein refer to an —O-alkyl group. Representative alkoxyl groups include methoxy, ethoxy, propyloxy, tert-butoxy, and the like. An 'ether' is two hydrocarbons covalently linked by an oxygen. Accordingly, the substituent of a hydrocarbon that renders that hydrocarbon an ether can be an alkoxyl, or another moiety such as —O-aryl, —O-heteroaryl, —O-heteroalkyl, —O-aralkyl, —O-heteroaralkyl, —O-carbocyclic aliphatic, or —O-heterocyclic aliphatic.

An 'alkylseleno' or 'selenoalkyl' refers to a —Se-alkyl group. 'Selenoethers' more broadly refers to two hydrocarbon groups linked by a selenium atom. Accordingly, the substituent of a hydrocarbon that renders that hydrocarbon a selenoether can be an alkylseleno, or another moiety such as —Se-aryl, —Se-heteroaryl, —Se-heteroalkyl, —Se-aralkyl, —Se-heteroaralkyl, —Se-carbocyclic aliphatic, or —Se-heterocyclic aliphatic.

The term 'alkylthio' refers to an —S-alkyl group. Representative alkylthio groups include methylthio, ethylthio, and the like. 'Thioether' refers to a sulfur atom bound to two hydrocarbon substituents, e.g., an ether wherein the oxygen is replaced by sulfur. Thus, a thioether substituent on a carbon atom refers to a hydrocarbon-substituted sulfur atom substituent, such as alkylthio or arylthio, etc.

The term 'aralkyl', as used herein, refers to an alkyl group substituted with an aryl group.

'Aryl ring' refers to an aromatic hydrocarbon ring system. Aromatic rings are monocyclic or fused bicyclic ring systems, such as phenyl, naphthyl, etc. Monocyclic aromatic rings contain from about 5 to about 10 carbon atoms, preferably from 5 to 7 carbon atoms, and most preferably from 5 to 6 carbon atoms in the ring. Bicyclic aromatic rings contain from 8 to 12 carbon atoms, preferably 9 or 10 carbon atoms in the ring. The term 'aryl' also includes bicyclic ring systems wherein only one of the rings is aromatic, e.g., the other ring is cycloalkyl, cycloalkenyl, or heterocyclyl. Aromatic rings may be unsubstituted or substituted with from 1 to about 5 substituents on the ring. Preferred aromatic ring substituents include: halo, cyano, lower alkyl, heteroalkyl, haloalkyl, phenyl, phenoxy, or any combination thereof. More preferred substituents include lower alkyl, cyano, halo, and haloalkyl.

'Biohydrolyzable amide' refers to an amide moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Biohydrolyzable ester' refers to an ester moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Biohydrolyzable imide' refers to an imide moiety that is cleaved (e.g., to form a hydroxyl and a carboxylic acid) under physiological conditions. Physiological conditions include the acidic and basic environments of the digestive tract (e.g., stomach, intestines, etc.), enzymatic cleavage, metabolism, and other biological processes, and preferably refer to physiological conditions in a vertebrate, such as a mammal.

'Carbocyclic aliphatic ring' refers to a saturated or unsaturated hydrocarbon ring. Carbocyclic aliphatic rings are not aromatic. Carbocyclic aliphatic rings are monocyclic, or are fused, spiro, or bridged bicyclic ring systems. Monocyclic carbocyclic aliphatic rings contain from about 4 to about 10 carbon atoms, preferably from 4 to 7 carbon atoms, and most preferably from 5 to 6 carbon atoms in the ring. Bicyclic carbocyclic aliphatic rings contain from 8 to 12 carbon atoms, preferably from 9 to 10 carbon atoms in the ring. Carbocyclic aliphatic rings may be unsubstituted or substituted with from 1 to 4 substituents on the ring. Preferred carbocyclic aliphatic ring substituents include halo, cyano, alkyl, heteroalkyl, haloalkyl, phenyl, phenoxy or any combination thereof. More preferred substituents include halo and haloalkyl. Preferred carbocyclic aliphatic rings include cyclopentyl, cyclohexyl, cyclohexenyl, cycloheptyl, and cyclooctyl. More preferred carbocyclic aliphatic rings include cyclohexyl, cycloheptyl, and cyclooctyl.

The term 'carbonyl' is art-recognized and includes such moieties as can be represented by the general formula:

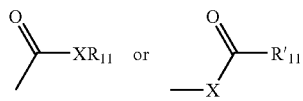

wherein X is a bond or represents an oxygen or a sulfur, and $R_{11}$ represents a hydrogen, hydrocarbon substituent, or a pharmaceutically acceptable salt, $R_{11'}$ represents a hydrogen or hydrocarbon substituent. Where X is an oxygen and $R_{11}$ or $R_{11'}$ is not hydrogen, the formula represents an 'ester'. Where X is an oxygen, and $R_{11}$ is as defined above, the moiety is referred to herein as a carboxyl group, and particularly when $R_{11'}$ is a hydrogen, the formula represents a 'carboxylic acid'. Where X is an oxygen, and $R_{11'}$ is hydrogen, the formula represents a 'formate'. In general, where the oxygen atom of the above Formula IIs replaced by sulfur, the formula represents a 'thiocarbonyl' group. Where X is a sulfur and $R_{11}$ or $R_{11'}$ is not hydrogen, the formula represents a 'thioester.' Where X is a sulfur and $R_{11}$ is hydrogen, the formula represents a 'thiocarboxylic acid.' Where X is a sulfur and $R_{11'}$ is hydrogen, the formula represents a 'thioformate.' On the other hand, where X is a bond, $R_{11}$ is not hydrogen, and the carbonyl is bound to a hydrocarbon, the above formula represents a 'ketone' group. Where X is a bond, $R_{11}$ is hydrogen, and the carbonyl is bound to a hydrocarbon, the above formula represents an 'aldehyde' or 'formyl' group.

'Ci alkyl' is a heteroalkyl chain having i member atoms. For example, C4 alkyls contain four carbon member atoms. C4 alkyls containing may be saturated or unsaturated with one or two double bonds (cis or trans) or one triple bond. Preferred C4 alkyls are saturated. Preferred unsaturated C4 alkyl have one double bond. C4 alkyl may be unsubstituted or substituted with one or two substituents. Preferred substituents include lower alkyl, lower heteroalkyl, cyano, halo, and haloalkyl.

'Halogen' refers to fluoro, chloro, bromo, or iodo substituents. Preferred halo are fluoro, chloro and bromo; more preferred are chloro and fluoro.

'Haloalkyl' refers to a straight, branched, or cyclic hydrocarbon substituted with one or more halo substituents. Preferred haloalkyl are C1-C12; more preferred are C1-C6; more preferred still are C1-C3. Preferred halo substituents are fluoro and chloro. The most preferred haloalkyl is trifluoromethyl.

'Heteroalkyl' is a saturated or unsaturated chain of carbon atoms and at least one heteroatom, wherein no two heteroatoms are adjacent. Heteroalkyl chains contain from 1 to 18 member atoms (carbon and heteroatoms) in the chain, preferably 1 to 12, more preferably 1 to 6, more preferably still 1 to 4. Heteroalkyl chains may be straight or branched. Preferred branched heteroalkyl have one or two branches, preferably one branch. Preferred heteroalkyl are saturated. Unsaturated heteroalkyl have one or more double bonds and/or one or more triple bonds. Preferred unsaturated heteroalkyl have one or two double bonds or one triple bond, more preferably one double bond. Heteroalkyl chains may be unsubstituted or substituted with from 1 to about 4 substituents unless otherwise specified. Preferred heteroalkyl are unsubstituted. Preferred heteroalkyl substituents include halo, aryl (e.g., phenyl, tolyl, alkoxyphenyl, alkoxycarbonylphenyl, halophenyl), heterocyclyl, heteroaryl. For example, alkyl chains substituted with the following substituents are heteroalkyl: alkoxy (e.g., methoxy, ethoxy, propoxy, butoxy, pentoxy), aryloxy (e.g., phenoxy, chlorophenoxy, tolyloxy, methoxyphenoxy, benzyloxy, alkoxycarbonylphenoxy, acyloxyphenoxy), acyloxy (e.g., propionyloxy, benzoyloxy, acetoxy), carbamoyloxy, carboxy, mercapto, alkylthio, acylthio, arylthio (e.g., phenylthio, chlorophenylthio, alkylphenylthio, alkoxyphenylthio, benzylthio, alkoxycarbonylphenylthio), amino (e.g., amino, mono- and di-C1-C3 alkylamino, methylphenylamino, methylbenzylamino, C1-C3 alkylamido, carbamamido, ureido, guanidino).

'Heteroatom' refers to a multivalent non-carbon atom, such as a boron, phosphorous, silicon, nitrogen, sulfur, or oxygen atom, preferably a nitrogen, sulfur, or oxygen atom. Groups containing more than one heteroatom may contain different heteroatoms.

'Heteroaryl ring' refers to an aromatic ring system containing carbon and from 1 to about 4 heteroatoms in the ring. Heteroaromatic rings are monocyclic or fused bicyclic ring systems. Monocyclic heteroaromatic rings contain from about 5 to about 10 member atoms (carbon and heteroatoms), preferably from 5 to 7, and most preferably from 5 to 6 in the ring. Bicyclic heteroaromatic rings contain from 8 to 12 member atoms, preferably 9 or 10 member atoms in the ring. The term 'heteroaryl' also includes bicyclic ring systems wherein only one of the rings is aromatic, e.g., the other ring is cycloalkyl, cycloalkenyl, or heterocyclyl. Heteroaromatic rings may be unsubstituted or substituted with from 1 to about 4 substituents on the ring. Preferred heteroaromatic ring substituents include halo, cyano, lower alkyl, heteroalkyl, haloalkyl, phenyl, phenoxy or any combination thereof. Preferred heteroaromatic rings include thienyl, thiazolyl, oxazolyl, pyrrolyl, purinyl, pyrimidyl, pyridyl, and furanyl. More preferred heteroaromatic rings include thienyl, furanyl, and pyridyl.

'Heterocyclic aliphatic ring' is a non-aromatic saturated or unsaturated ring containing carbon and from 1 to about 4 heteroatoms in the ring, wherein no two heteroatoms are adjacent in the ring and preferably no carbon in the ring attached to a heteroatom also has a hydroxyl, amino, or thiol group attached to it. Heterocyclic aliphatic rings are monocyclic, or are fused or bridged bicyclic ring systems. Monocyclic heterocyclic aliphatic rings contain from about 4 to about 10 member atoms (carbon and heteroatoms), preferably from 4 to 7, and most preferably from 5 to 6 member atoms in the ring. Bicyclic heterocyclic aliphatic rings contain from 8 to 12 member atoms, preferably 9 or 10 member atoms in the ring. Heterocyclic aliphatic rings may be unsubstituted or substituted with from 1 to about 4 substituents on the ring. Preferred heterocyclic aliphatic ring substituents include halo, cyano, lower alkyl, heteroalkyl, haloalkyl, phenyl, phenoxy or any combination thereof. More preferred substituents include halo and haloalkyl. Heterocyclyl groups include, for example, thiophene, thianthrene, furan, pyran, isobenzofuran, chromene, xanthene, phenoxathin, pyrrole, imidazole, pyrazole, isothiazole, isoxazole, pyridine, pyrazine, pyrimidine, pyridazine, indolizine, isoindole, indole, indazole, purine, quinolizine, isoquinoline, hydantoin, oxazoline, imidazolinetrione, triazolinone, quinoline, phthalazine, naphthyridine, quinoxaline, quinazoline, quinoline, pteridine, carbazole, carboline, phenanthridine, acridine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. Preferred heterocyclic aliphatic rings include piperazyl, morpholinyl, tetrahydrofuranyl, tetrahydropyranyl and piperidyl. Heterocycles can also be polycycles.

The term 'hydroxyl' means —OH.

'Lower alkyl' refers to an alkyl chain comprised of 1 to 5, preferably 1 to 4 carbon member atoms, more preferably 1 or 2 carbon member atoms. Lower alkyls may be saturated or unsaturated. Preferred lower alkyls are saturated. Lower alkyls may be unsubstituted or substituted with one or about two substituents. Preferred substituents on lower alkyl include cyano, halo, trifluoromethyl, amino, and hydroxyl. Throughout the application, preferred alkyl groups are lower alkyls. In preferred embodiments, a substituent designated herein as alkyl is a lower alkyl. Likewise, 'lower alkenyl' and 'lower alkynyl' have similar chain lengths.

'Lower heteroalkyl' refers to a heteroalkyl chain comprised of 1 to 4, preferably 1 to 3 member atoms, more preferably 1 to 2 member atoms. Lower heteroalkyl contain one or two non-adjacent heteroatom member atoms. Preferred lower heteroalkyl contain one heteroatom member atom. Lower heteroalkyl may be saturated or unsaturated. Preferred lower heteroalkyl are saturated. Lower heteroalkyl may be unsubstituted or substituted with one or about two substituents. Preferred substituents on lower heteroalkyl include cyano, halo, trifluoromethyl, and hydroxyl.

'Mi heteroalkyl' is a heteroalkyl chain having i member atoms. For example, M4 heteroalkyls contain one or two non-adjacent heteroatom member atoms. M4 heteroalkyls containing 1 heteroatom member atom may be saturated or unsaturated with one double bond (cis or trans) or one triple bond. Preferred M4 heteroalkyl containing 2 heteroatom member atoms are saturated. Preferred unsaturated M4 heteroalkyl have one double bond. M4 heteroalkyl may be unsubstituted or substituted with one or two substituents. Preferred substituents include lower alkyl, lower heteroalkyl, cyano, halo, and haloalkyl.

'Member atom' refers to a polyvalent atom (e.g., C, O, N, or S atom) in a chain or ring system that constitutes a part of the chain or ring. For example, in cresol, six carbon atoms are member atoms of the ring and the oxygen atom and the carbon atom of the methyl substituent are not member atoms of the ring.

As used herein, the term 'nitro' means —NO$_2$.

'Pharmaceutically acceptable salt' refers to a cationic salt formed at any acidic (e.g., hydroxamic or carboxylic acid) group, or an anionic salt formed at any basic (e.g., amino or guanidino) group. Such salts are well known in the art. See e.g., World Patent Publication 87/05297, Johnston et al., published Sep. 11, 1987, incorporated herein by reference. Such salts are made by methods known to one of ordinary skill in the art. It is recognized that the skilled artisan may prefer one salt over another for improved solubility, stability, formulation ease, price and the like. Determination and optimization of such salts is within the purview of the skilled artisan's practice. Preferred cations include the alkali metals (such as sodium and potassium), and alkaline earth metals (such as magnesium and calcium) and organic cations, such as trimethylammonium, tetrabutylammonium, etc. Preferred anions include halides (such as chloride), sulfonates, carboxylates, phosphates, and the like. Clearly contemplated in such salts are addition salts that may provide an optical center where once there was none. For example, a chiral tartrate salt may be prepared from the compounds of the invention. This definition includes such chiral salts.

'Phenyl' is a six-membered monocyclic aromatic ring that may or may not be substituted with from 1 to 5 substituents. The substituents may be located at the ortho, meta or para position on the phenyl ring, or any combination thereof. Preferred phenyl substituents include: halo, cyano, lower alkyl, heteroalkyl, haloalkyl, phenyl, phenoxy or any combination thereof. More preferred substituents on the phenyl ring include halo and haloalkyl. The most preferred substituent is halo.

The terms 'polycyclyl' and 'polycyclic group' refer to two or more rings (e.g., cycloalkyls, cycloalkenyls, heteroaryls, aryls and/or heterocyclyls) in which two or more member atoms of one ring are member atoms of a second ring. Rings that are joined through non-adjacent atoms are termed 'bridged' rings, and rings that are joined through adjacent atoms are 'fused rings'.

The term 'sulfhydryl' means —SH, and the term 'sulfonyl' means —SO$_2$—.

The term 'sulfamoyl' is art-recognized and includes a moiety represented by the general formula:

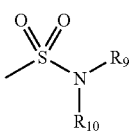

in which $R_9$ and $R_{10}$ are as defined above.

The term 'sulfate' is art-recognized and includes a moiety that can be represented by the general formula:

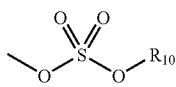

in which $R_{10}$ is as defined above.

The term 'sulfonamido' is art-recognized, and includes a moiety represented by the general formula:

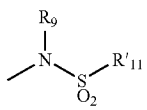

in which $R_9$ and $R'_{11}$ are as defined above.

The terms 'sulfoxido' and 'sulfinyl', as used herein, are art-recognized and include a moiety represented by the general formula:

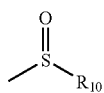

in which $R_9$ is as defined above.

A 'substitution' or 'substituent' on a small organic molecule generally refers to a position on a multi-valent atom bound to a moiety other than hydrogen, e.g., a position on a chain or ring exclusive of the member atoms of the chain or ring. Such moieties include those defined herein and others as are known in the art, for example, halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl or heteroaryl. It will be understood by those skilled in the art that certain substituents, such as aryl, heteroaryl, polycyclyl, alkoxy, alkylamino, alkyl, cycloalkyl, heterocyclyl, alkenyl, alkynyl, heteroalkyl, heteroalkenyl, and heteroalkynyl, can themselves be substituted, if appropriate. This invention is not intended to be limited in any manner by the permissible substituents of organic compounds. It will be understood that 'substitution' or 'substituted with' includes the implicit proviso that such substitution is in accordance with permitted valence of the substituted atom and the substituent, and that the substitution results in a stable compound, e.g., which does not spontaneously undergo transformation such as by rearrangement, cyclization, elimination, hydrolysis, etc.

As used herein, the definition of each expression, e.g., alkyl, m, n, etc., when it occurs more than once in any structure, is intended to be independent of its definition elsewhere in the same structure.

The abbreviations Me, Et, Ph, Tf, Nf, Ts, and Ms represent methyl, ethyl, phenyl, trifluoromethanesulfonyl, nonafluorobutanesulfonyl, p-toluenesulfonyl, and methanesulfonyl, respectively. A more comprehensive list of the abbreviations utilized by organic chemists of ordinary skill in the art appears in the first issue of each volume of the *Journal of Organic Chemistry*; this list is typically presented in a table entitled *Standard List of Abbreviations*. The abbreviations contained in said list, and all abbreviations utilized by organic chemists of ordinary skill in the art are hereby incorporated by reference.

The terms ortho, meta and para apply to 1,2-, 1,3- and 1,4-disubstituted benzenes, respectively. For example, the names 1,2-dimethylbenzene and ortho-dimethylbenzene are synonymous.

The phrase 'protecting group' as used herein means temporary substituents that protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis,* $2^{nd}$ ed.; Wiley: New York, 1991; and Kocienski, P. J. *Protecting Groups*, Georg Thieme Verlag: New York, 1994).

For purposes of this invention, the chemical elements are identified in accordance with the Periodic Table of the Elements, CAS version, Handbook of Chemistry and Physics, 67th Ed., 1986-87, inside cover. Also for purposes of this invention, the term 'hydrocarbon' is contemplated to include all permissible compounds or moieties having at least one carbon-hydrogen bond. In a broad aspect, the permissible hydrocarbons include acyclic and cyclic, branched and unbranched, carbocyclic and heterocyclic, aromatic and non-aromatic organic compounds which can be substituted or unsubstituted.

Certain compounds of the present invention may exist in particular geometric or stereoisomeric forms. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts can be formed with an appropriate optically active acid or base, followed by resolution of the diastereomers thus formed by fractional crystallization or chromatographic means well known in the art, and subsequent recovery of the purified enantiomers. Enantiomers may also be separated using a 'chiral column', i.e., by chromatographically separating the enantiomers using chiral molecules bound to a solid support.

Contemplated equivalents of the compounds described above include compounds which otherwise correspond thereto, and which have the same useful properties thereof, wherein one or more simple variations of substituents are made which do not adversely affect the efficacy of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

III. Exemplary Applications of Method and Compositions

One aspect of the present invention relates to a method of maintaining a differentiated state, e.g., enhancing survival, of a neuronal cell, by contacting the cells with a trophic amount of a subject compound. For instance, it is contemplated by the invention that, the subject method could be used to maintain differentiated neuronal tissue both in vitro and in vivo.

The present method is applicable to cell culture techniques. In vitro neuronal culture systems have proved to be fundamental and indispensable tools for the study of neural development, as well as the identification of neurotrophic factors such as nerve growth factor (NGF), ciliary neurotrophic factors (CNTF) (see Lin et al. *Science* 1989, 246, 1023-1025), glial cell line-derived neurotrophic factor (GDNF) (see Lin et al. *Science* 1993, 260, 1130-1132), and brain-derived neurotrophic factor (BDNF) (see Leibrock et al. *Nature* 1989, 341, 149-152). Once a neuronal cell has become terminally differentiated it typically will not change to another terminally differentiated cell-type. However, neuronal cells can nevertheless readily lose their differentiated state. This is commonly observed when they are grown in culture from adult tissue, and when they form a blastema during regeneration. The present method provides a means for ensuring an adequately restrictive environment in order to maintain dopaminergic neuron and motoneuron in differentiated states, and can be employed, for instance, in cell cultures designed to test the specific activities of other trophic factors.

In such embodiments of the subject method, a culture of differentiated cells including dopaminergic neurons and/or motoneurons can be contacted with a subject compound in order to maintain the integrity of a culture of terminally differentiated neuronal cells by preventing loss of differentiation. Such neuronal cultures can be used as convenient assay systems as well as sources of implantable cells for therapeutic treatments.

The subject method can be used in conjunction with agents that induce the differentiation of neuronal precursors, e.g., progenitor or stem cells, into dopaminergic neurons or motoneurons.

Cells can be obtained from embryonic, post-natal, juvenile or adult neural tissue from any animal. By any animal is meant any multicellular animal that contains nervous tissue. More particularly, is meant any fish, reptile, bird, amphibian or mammal and the like. The most preferable donors are mammals, especially humans and non-human primates, pigs, cows, and rodents.

Intracerebral neural grafting has emerged recently as an additional potential to CNS therapy. For example, one approach to repairing damaged brain tissues involves the transplantation of cells from fetal or neonatal animals into the adult brain (Dunnett et al. *J Exp Biol* 1987, 123, 265-289; and Freund et al. *J Neurosci* 1985. 5, 603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. Transplantation of fetal brain cells, which contain precursors of the dopaminergic neurons, has been examined with success as a treatment for Parkinson's disease. In animal models and in patients with this disease, fetal brain cell transplantations have resulted in the reduction of motor abnormalities. Furthermore, it appears that the implanted fetal dopaminergic neurons form synapses with surrounding host neurons. However, in the art, the transplantation of fetal brain cells is limited due, for example, to the limited survival time of the implanted neuronal precursors and differentiated neurons arising therefrom. The subject invention provides a means for extending the usefulness of such transplants by enhancing the survival of dopaminergic neurons and/or motoneurons in the transplant.

In the specific case of Parkinson's disease, treatment with a subject compound can improve the in vivo survival of fetal and adult dopaminergic neurons, and thus can provide a more effective treatment of this disease.

In the case of a heterologous donor animal, the animal may be euthanized, and the brain and specific area of interest removed using a sterile procedure. Brain areas of particular interest include any area from which progenitor cells can be obtained which will provide dopaminergic neurons or motoneurons upon differentiation. These regions include areas of the central nervous system (CNS) including the substantia nigra pars compacta, which is found to be degenerated in Parkinson's Disease patients.

Human heterologous neural progenitor cells may be derived from fetal tissue obtained from elective abortion, or from a post-natal, juvenile or adult organ donor. Autologous neural tissue can be obtained by biopsy, or from patients undergoing neurosurgery in which neural tissue is removed, such as during epilepsy surgery.

Cells can be obtained from donor tissue by dissociation of individual cells from the connecting extracellular matrix of the tissue. Dissociation can be obtained using any known procedure, including treatment with enzymes such as trypsin, collagenase and the like, or by using physical methods of dissociation such as with a blunt instrument. Dissociation of fetal cells can be carried out in tissue culture medium, while a preferable medium for dissociation of juvenile and adult cells is artificial cerebral spinal fluid (aCSF). Regular aCSF contains 124 mM NaCl, 5 mM KCl, 1.3 mM $MgCl_2$, 2 mM $CaCl_2$, 26 mM $NaHCO_3$, and 10 mM D-glucose. Low $Ca^{2+}$ aCSF contains the same ingredients except for $MgCl_2$ at a concentration of 3.2 mM and $CaCl_2$ at a concentration of 0.1 mM.

Dissociated cells can be placed into any known culture medium capable of supporting cell growth, including MEM, DMEM, RPMI, F-12, and the like, containing supplements which are required for cellular metabolism such as glutamine and other amino acids, vitamins, minerals and useful proteins such as transferrin and the like. Medium may also contain antibiotics to prevent contamination with yeast, bacteria and fungi such as penicillin, streptomycin, gentamicin and the like. In some cases, the medium may contain serum derived from bovine, equine, chicken and the like. A particularly preferable medium for cells is a mixture of DMEM and F-12.

Conditions for culturing should be close to physiological conditions. The pH of the culture media should be close to physiological pH, preferably between pH 6-8, more preferably close to pH 7, even more particularly about pH 7.4. Cells should be cultured at a temperature close to physiological temperature, preferably between 30° C.-40° C., more preferably between 32° C.-38° C., and most preferably between 35° C.-37° C.

Cells can be grown in suspension or on a fixed substrate, but proliferation of the progenitors is preferably done in suspension to generate large numbers of cells by formation of "neurospheres" (see, for example, Reynolds et al. *Science* 1992, 255, 1070-1709; and PCT Publications WO93/01275, WO94/09119, WO94/10292, and WO94/16718). In the case of propagating (or splitting) suspension cells, flasks are shaken well and the neurospheres allowed to settle on the bottom corner of the flask. The spheres are then transferred to a 50 ml centrifuge tube and centrifuged at low speed. The medium is aspirated, the cells resuspended in a small amount of medium with growth factor, and the cells mechanically dissociated and resuspended in separate aliquots of media.

Cell suspensions in culture medium are supplemented with any growth factor that allows for the proliferation of progenitor cells and seeded in any receptacle capable of sustaining cells, though as set out above, preferably in culture flasks or roller bottles. Cells typically proliferate within 3-4 days in a 37° C. incubator, and proliferation can be reinitiated at any time after that by dissociation of the cells and resuspension in fresh medium containing growth factors.

In the absence of substrate, cells lift off the floor of the flask and continue to proliferate in suspension forming a hollow sphere of undifferentiated cells. After approximately 3-10 days in vitro, the proliferating clusters (neurospheres) are fed every 2-7 days, and more particularly every 2-4 days by gentle centrifugation and resuspension in medium containing growth factor.

After 6-7 days in vitro, individual cells in the neurospheres can be separated by physical dissociation of the neurospheres with a blunt instrument, more particularly by triturating the neurospheres with a pipette. Single cells from the dissociated neurospheres are suspended in culture medium containing growth factors, and differentiation of the cells can be induced by plating (or resuspending) the cells in the presence of a factor capable of sustaining differentiation, e.g., such as a subject compound of the present invention.

Stem cells useful in the present invention are generally known. For example, several neural crest cells have been identified, some of which are multipotent and likely represent uncommitted neural crest cells. The role of subject compounds employed in the present method to culture such stem cells is to maintain differentiation a committed progenitor cell and/or a terminally differentiated dopaminergic neuron or motoneuron. The subject compound can be used alone, or can be used in combination with other neurotrophic factors that act to more particularly enhance a particular differentiation fate of the neuronal progenitor cell.

In addition to the implantation of cells cultured in the presence of a subject compound and other in vitro uses described above, yet another aspect of the present invention concerns the therapeutic application of a subject compound to enhance survival of dopaminergic neurons and motoneurons in vivo. The ability of a subject compound to maintain neuronal differentiation of dopaminergic neuron and motoneuron indicates that such compounds can reasonably be expected to facilitate control of these neuronal cell-types in adult tissue with regard to maintenance, functional performance, aging and prevention of degeneration and premature death which result from loss of differentiation in certain pathological conditions. In light of this understanding, the present invention specifically contemplates applications of the subject method to the treatment of (prevention and/or reduction of the severity of) neurological conditions deriving from (i) loss of dopaminergic cells, (ii) loss of motoneurons, and/or (iii) loss of neurons of the substantia nigra. In this regard, the subject method is useful in the treatment of chronic neurodegenerative diseases of the nervous system, including Parkinson's disease, amylotrophic lateral sclerosis and the like.

Many neurological disorders are associated with degeneration of discrete populations of neuronal elements and may be treatable with a therapeutic regimen that includes a compound according to the subject invention. As described in the appended examples, subject compounds exert trophic and survival-promoting actions on substantia nigra dopaminergic neurons. In vivo, treatment with a subject compound is expected to stimulate the dopaminergic phenotype of substantia nigra neurons and restore functional deficits induced by axotomy or dopaminergic neurotoxins, and may be used the treatment of Parkinson's disease, a neurodegenerative disease characterized by the loss of dopaminergic neurons. Thus, in one embodiment, the subject method comprises administering to an animal afflicted with Parkinson's disease, or at risk of developing Parkinson's disease, an amount of a subject compound effective for increasing the rate of survival of dopaminergic neurons in the animal. In preferred embodiments, the method includes administering to the animal an amount of a subject compound that would otherwise be effective at protecting the substantia nigra from MPTP-mediated toxicity when MPTP is administered at a dose of 05 mg/kg, more preferably at a dose of 2 mg/kg, 5 mg/kg, 10 mg/kg, 20 mg/kg or 50 mg/kg and, still more preferably, at a dose of 100 g/kg.

Amyotrophic lateral sclerosis (ALS) is a fatal neurodegenerative disease in which the loss of spinal and cranial motoneurons is a defining feature. Treatment of patients suffering from such degenerative conditions can include the application of a subject compound in order to control, for example, apoptotic events that give rise to loss of motoneurons (e.g., to enhance survival of existing neurons).

Recently it has been reported that in certain ALS patients and animal models a significant loss of midbrain dopaminergic neurons occurs in addition to the loss of spinal motor neurons. For instance, the literature describes degeneration of the substantia nigra in some patients with familial amyotrophic lateral sclerosis (Kostic et al. *Ann Neurol* 1997, 41, 497-504). According the subject invention, a trophic amount of a subject compound can be administered to an animal suffering from, or at risk of developing, ALS.

In general, the therapeutic method of the present invention can be characterized as including a step of administering to an animal an amount of a subject compound effective to enhance the survival of a dopaminergic neurons and/or motoneurons. The mode of administration and dosage regimens will vary depending on the severity of the degenerative disorder being treated, e.g., the dosage may be altered as between a prophylaxsis and treatment. In preferred embodiments, the subject compound is administered systemically initially, then locally for medium- to long-term care. In certain embodiments, a source of a subject compound is stereotactically provided within or proximate the area of degeneration. The subject method may also find particular utility in treating or preventing the adverse neurological consequences of surgery. For example, certain cranial surgery can result in degeneration of neuronal populations for which the subject method can be applied.

In other embodiments, the subject method can be used to prevent or treat neurodegenerative conditions arising from the use of certain drugs, such as the compound MPTP (1-methyl-4-phenyl-1,2,3,6-tetrahydropyridine).

In still other embodiments, the subject method can be used in the prevention and/or treatment of hypoxia, e.g., as a neuroprotective agent. For instance, the subject method can be used prophylactically to lessen the neuronal cell death caused by altitude-induced hypoxia.

A method which is "neuroprotective", in the case of dopaminergic neurons and motoneurons, results in diminished loss of cells of those phenotype relative to that which would occur in the absence of treatment with a subject compound.

The subject method further has wide applicability to the treatment or prophylaxis of disorders affecting the regulation of peripheral nerves, including peripheral ganglionic neurons, sympathetic, sensory neurons, and motoneurons. In general, the method can be characterized as including administering to an animal an amount of a subject compound effective to alter the proliferative and/or differentiation state of treated peripheral nerve cells. Such therapeutic compositions may be useful in treatments designed to rescue, for example, retinal ganglia, inner ear and acoustic nerves, and motor neurons, from lesion-induced death as well as guiding reprojection of these neurons after such damage. Such diseases and conditions include, but are not limited to, chemical or mechanical trauma, infection (such as viral infection with varicella zoster), metabolic disease such as diabetes, nutritional deficiency, and toxic agents (such as cisplatin used in the treatment of a tumor). The goals of treatment in each case can be twofold: (1) to eliminate the cause of the disease and (2) to relieve its symptoms.

Peripheral neuropathy is a condition involving nerve-ending damage in the hands and feet. Peripheral neuropathy generally refers to a disorder that affects the peripheral nerves, most often manifested as one or a combination of motor, sensory, sensorimotor, or autonomic neural dysfunction. The wide variety of morphologies exhibited by peripheral neuropathies can each be uniquely attributed to an equally wide variety of causes. For instance, peripheral neuropathies can be genetically acquired, can result from a systemic disease, or can be induced by a toxic agent. Some toxic agents that cause neurotoxicities are therapeutic drugs, antineoplastic agents, contaminants in foods or medicinals, and environmental and industrial pollutants.

Peripheral neuropathy is a term used to describe disorders resulting from injury (e.g., mechanical, chemical, viral, bacterial, or genetic) to the peripheral nerves. It can be caused by diseases that affect only the peripheral nerves or by conditions that affect other parts of the body as well. Symptoms almost always involve weakness, numbness, or pain—usually in the arms and legs.

To further illustrate, the subject method can be used in the treatment of such acquired neuropathies as diabetic neuropathies; immune-mediated neuropathies such as Guillain-Barre syndrome (GBS) and variants, chronic inflammatory demyelinating polyneuropathy (CIDP), chronic polyneuropathies with antibodies to peripheral nerves, neuropathies associated with vasculitis or inflammation of the blood vessels in peripheral nerve, brachial or lumbosacral plexitis, and neuropathies associated with monoclonal gammopathies; neuropathies associated with tumors or neoplasms such as sensory neuropathy associated with lung cancer, neuropathy associated with multiple myeloma, neuropathy associated with waldenstrom's macroglobulemia, chronic lymphocytic leukemia, or B-cell lymphoma; neuropathy associated with amyloidosis; neuropathies caused by infections; neuropathies caused by nutritional imbalance; neuropathy in kidney disease; hypothyroid neuropathy; neuropathy caused by alcohol and toxins; neuropathies caused by drugs; neuropathy resulting from local irradiation; neuropathies caused by trauma or compression; and idiopathic neuropathies.

Likewise, the subject method can be used in the treatment of such hereditary neuropathies as Charcot-Marie-Tooth disease (CMT); familial amyloidotic neuropathy and other hereditary neuropathies; and hereditary porphyria.

In another embodiment, the subject method can be used to inhibit or otherwise slow neurodegenerative events associated with age-related neuropathology.

In particular, chemotherapeutic agents known to cause sensory and/or motor neuropathies include vincristine, an antineoplastic drug used to treat haematological malignancies and sarcomas, as well as cisplatin, taxol, and others. The neurotoxicity is dose-related, and exhibits as reduced intestinal motility and peripheral neuropathy, especially in the distal muscles of the hands and feet, postural hypotension, and atony of the urinary bladder. Similar problems have been documented with taxol and cisplatin (Mollman, J. E., *New Eng Jour Med* 1990, 322, 126-127), although cisplatin-related neurotoxicity can be alleviated with nerve growth factor (NGF) (Apfel, S. C. et al, *Annals of Neurology* 1992, 31, 76-80). Although the neurotoxicity is sometimes reversible after removal of the neurotoxic agent, recovery can be a very slow process (Legha, S., *Medical Toxicology* 1986, 1, 421-427; Olesen, et al., *Drug Safety* 1991, 6, 302-314).

There are a number of inherited peripheral neuropathies, including: Refsum's disease, Abetalipoproteinemia, Tangier disease, Krabbe's disease, metachromatic leukodystrophy, Fabry's disease, Dejerine-Sottas syndrome, and others. Of all the inherited neuropathies, the most common by far is Charcot-Marie-Tooth disease.

Charcot-Marie-Tooth (CMT) Disease (also known as peroneal muscular atrophy, or hereditary motor sensory neuropathy (HMSN)) is the most common hereditary neurological disorder. It is characterized by weakness and atrophy, primarily of the peroneal muscles, due to segmental demyelination of peripheral nerves and associated degeneration of axons and anterior horn cells. Autosomal dominant inheritance is usual, and associated degenerative CNS disorders, such as Friedreich's ataxia, are common.

In one aspect, the method of the present invention can be used in the treatment and maintenance of hereditary neuropathies. This group of neuropathies is now becoming increasingly recognized due to the dramatic advances in molecular genetics. The symptoms of the various hereditary neuropathies are wide ranging. A common denominator is usually the early onset of mild numbness and tingling in the feet that slowly progresses to involve the legs and the hands and later the rest of the upper extremities. Most of the hereditary neuropathies do have a motor component consisting of distal weakness in the lower and upper extremities. A majority of patients with hereditary neuropathies have high arches in their feet or other bony deformities. The symptoms are very slowly progressive and the majority of the patients are still walking two decades after the onset of their symptoms.

The diagnosis of a hereditary neuropathy is usually suggested with the early onset of neuropathic symptoms, especially when a positive family history is also present. Prior to the recent genetic advances, the diagnosis was supported by typical findings of marked slowing of the nerve conduction studies on electromyography and a nerve biopsy. Typical findings on a nerve biopsy include the presence of so-called onion-bulbs, indicating a recurring demyelinating and remyelinating of the nerve fibers. With the most recent genetic advances, two major hereditary neuropathies known as "Charcot-Marie-Tooth disease" and "hereditary neuropathy with liability to pressure palsies" can be diagnosed with a simple blood test that identifies the different mutations responsible for these two entities.

Hereditary neuropathies are caused by genetic abnormalities transmitted from generation to generation. For several of these, the genetic defect is known, and tests are available for diagnosis and prenatal counseling.

As set forth above, the subject method can be used as part of a therapeutic regimen in the treatment of Charcot-Marie Tooth Disease (CMT). This is a general term given to the hereditary sensorimotor neuropathies. CMT type 1 (CMT 1) is associated with demyelination or breakdown of the myelin sheaths. Several different abnormalities have been identified. CMT Type 1A is most commonly caused by duplication of a gene encoding a myelin protein called PMP-22, and CMT type 1B is caused by a mutation in a myelin protein called the Po glycoprotein. CMTX is a hereditary sensorimotor neuropathy that affects only men. It is caused by a mutation in a gene encoding a protein called Connexin 32 on the X-chromosome.

In certain embodiments, the subject method can be used to treat, or at least reduce the severity of, amyotrophic lateral sclerosis (ALS). According the subject invention, a trophic amount of a subject compound can be administered to an animal suffering from, or at risk of developing, ALS.

In another embodiment, the subject method can be used in the treatment of familial amyloidotic neuropathy and other related hereditary neuropathies. Amyloidotic neuropathy usually presents with pain, sensory loss and autonomic dysfunction. It is caused by a mutation in a protein called transthyretin, resulting in deposition of the protein as amyloid in the peripheral nerves.

The subject method can be used in the treatment of hereditary porphyria, which can have components of peripheral neuropathy.

Still another hereditary neuropathy for which the subject methods can be used for treatment is hereditary sensory neuropathy Type II (HSN II).

The methods and compositions of the present invention can also be used in the treatment and maintenance of acquired neuropathies.

For example, subject compounds can be used to prevent diabetic neuropathies. Diabetes is the most common known cause of neuropathy. It produces symptoms in approximately 10% of people with diabetes. In most cases, the neuropathy is predominantly sensory, with pain and sensory loss in the hands and feet. But some diabetics have mononeuritis or mononeuritis multiplex, which causes weakness in one or more nerves, or lumbosacral plexopathy or amyotrophy, which causes weakness in the legs.

The instant method can also be used in the treatment of immune-mediated neuropathies. The main function of the immune system is to protect the body against infectious organisms which enter from outside. In some cases, however the immune system turns against the body and causes autoimmune disease. The immune system consists of several types of white blood cells, including T-lymphocytes, which also regulate the immune response; and B-lymphocytes or plasma cells, which secrete specialized proteins called antibodies. Sometimes, for unknown reasons, the immune system mistakenly attacks parts of the body such as the peripheral nenes. This is autoimmune peripheral neuropathy. There are several different types, depending on the part of the peripheral nerve that is attacked and the type of the immune reaction. The following are brief descriptions of the neuropathies that are mediated by the immune system.

For instance, a subject compound can be used to treat Guillain-Barre Syndrome (GBS), an acute neuropathy because it comes on suddenly or rapidly. Guillain-Barre Syndrome can progress to paralysis and respiratory failure within days or weeks after onset. The neuropathy is caused when the immune system destroys the myelin sheaths of the motor and sensory nerves. It is often preceded by infection, vaccination or trauma, and that is thought to be what triggers the autoimmune reaction. The disease is self-limiting, with spontaneous recovery within six to eight weeks. But the recovery is often incomplete.

Other neuropathies which begin acutely, and which can be treated by the method of the present invention, include acute motor neuropathy, acute sensory neuropathy, and acute autonomic neuropathy, in which there is an immune attack against the motor, sensory or autonomic nerves, respectively. The Miller-Fisher syndrome is another variant in which there is paralysis of eye gaze, incoordination, and unsteady gait.

Still another acquired neuropathy which is may be treated by the subject method is chronic inflammatory demyelinating polyneuropathy (CIDP). CIDP is thought to be a chronic and more indolent form of the Guillain-Barre syndrome. The disease progresses either with repeated attacks, called relapses, or in a stepwise or steady fashion. As in GBS, there appears to be destruction of the myelin sheath by antibodies and T-lymphocytes. But since there is no specific test for CIDP, the diagnosis is based on the clinical and laboratory characteristics.

Chronic polyneuropathies with antibodies to peripheral nerves is still another peripheral neuropathy for which the subject methods can be employed to treat or prevent. In some types of chronic neuropathies, antibodies to specific components of nerve have been identified. These include demyelinating neuropathy associated with antibodies to the myelin-associated glycoprotein (MAG), motor neuropathy associated with antibodies to the gangliosides GM1 or GD1a, and sensory neuropathy associated with anti-sulfatide or GD1b ganglioside antibodies. The antibodies in these cases bind to oligosaccharide or sugar like molecules, which are linked to proteins (glycoproteins) or lipids (glycolipids or gangliosides) in the nerves. It is suspected that these antibodies may be responsible for the neuropathies.

The subject method can also be used as part of a therapeutic plan for treating neuropathies associated with vasculitis or inflammation of the blood vessels in peripheral nerves. Neuropathy can also be caused by vasculitis—an inflammation of the blood vessels in peripheral nerve. It produces small "strokes" along the course of the peripheral nerves, and may be restricted to the nerves or it may be generalized, include a skin rash, or involve other organs. Several rheumatological diseases like rheumatoid arthritis, lupus, periarteritis nodosa, or Sjogren's syndrome, are associated with generalized vasculitis, which can also involve the peripheral nerves. Vasculitis can cause polyneuritis, mononeuritis, or mononeuritis multiplex, depending on the distribution and severity of the lesions.

In still another embodiment, the method of the present invention can be used for treatment of brachial or lumbosacral plexitis. The brachial plexus, which lies under the armpit, contains the nerves to the arm and hand. Brachial plexitis is the result of inflammation of that nerve bundle, and produces weakness and pain in one or both arms. Lumbosacral plexitis, which occurs in the pelvis, causes weakness and pain in the legs.

Subject compounds may also be suitable for use in the treatment of neuropathies associated with monoclonal gammopathies. In monoclonal gammopathy, single clones of B-cells or plasma cells in the bone marrow or lymphoid organs expand to form benign or malignant tumors and secrete antibodies. The term 'monoclonal' is used because there are single clones of antibodies, and 'gammopathy' stands for gammaglobulins, which is another name for antibodies. In some cases, the antibodies react with nerve components; in others, fragments of the antibodies form amyloid deposits.

Yet another aspect of the present invention relates to the use of the subject method in the treatment of neuropathies associated with tumors or neoplasms. Neuropathy can be due to direct infiltration of nerves by tumor cells or to indirect effect of the tumor. The latter is called paraneoplastic neuropathy. Several types have been described. For instance, the subject methods can be used to manage sensory neuropathy associated with lung cancer. This neuropathy is associated with antibodies to a protein called Hu, which is present in the sensory neurons of the peripheral nerves. Likewise, the subject method can be used to treat neuropathies associated with multiple myeloma. Multiple myeloma is a bony tumor that is caused by antibody-secreting plasma cells in the bone marrow. The tumor is made up of a single clone of plasma cells, and the antibodies they produce are identical or monoclonal. Some people with multiple myeloma develop a sensorimotor polyneuropathy with degeneration of axons in the peripheral nerves. In other embodiments, the subject method can be used to treat neuropathies associated with Waldenstrom's macroglobulemia, chronic lymphocytic leukemia, or B-cell lymphoma. These are tumors caused by antibody-secreting B-lymphocytes in the spleen, bone marrow or lymph nodes. These antibodies are monoclonal and frequently react with peripheral nerve components such as MAG, GM1, or sulfatide. In still other embodiments, the compounds of the present invention can be used as part of therapeutic protocol for the treatment of patients with cancers where neuropathy is a consequence of local irradiation or be caused by medications such as vincristine and cisplatinum.

The present invention also contemplates the use of subject compounds for the treatment of neuropathies associated with amyloidosis. Amyloid is a substance that is deposited in the peripheral nerves and interferes with their operation: the resultant disorder is amyloidosis. There are two main types: primary amyloidosis, in which the deposits contain fragments of monoclonal antibodies (see the monoclonal gammopathy paragraph above); and hereditary amyloidosis in which the deposits contain a mutated protein called transthyretin. Primary amyloidosis is usually associated with monoclonal gammopathies or myeloma (see above).

Still another aspect of the present invention provides the subject method as a means for treating neuropathies caused by infections. Peripheral neuropathies can be caused by infection of the peripheral nerves. Viruses that cause peripheral neuropathies include the AIDS virus, HIV-I, which causes slowly progressive sensory neuropathy, cytomegalovirus, which causes a rapidly progressive paralytic neuropathy, Herpes zoster, which causes shingles, and poliovirus, which causes a motor neuropathy. Hepatitis B or C infections are sometimes associated with vasculitic neuropathy.

Bacterial infections that cause neuropathy include leprosy, which causes a patchy sensory neuropathy, and diphtheria, which can cause a rapidly progressive paralytic neuropathy. Other infectious diseases that cause neuropathy include Lyme disease, which is caused by a spirochete, and trypanosomiasis, which is caused by a parasite. Both commonly present a multifocal neuropathy.

Neuropathies caused by nutritional imbalance are also candidate disorders for treatment by the subject method. Deficiencies of vitamins B12, B1 (thiamine), B6 (pyridoxine), or E, for example, can produce polyneuropathies with degeneration of peripheral nerve axons. This can be due to poor diet, or inability to absorb the nutrients from the stomach or gut.

Moreover megadoses of vitamin B6 can also cause a peripheral neuropathy, and the subject method can be used as part of a de-toxification program in such cases.

Yet another use of the subject method is in the treatment of neuropathies arising in kidney diseases. Chronic renal failure can cause a predominantly sensory peripheral neuropathy with degeneration of peripheral nerve axons.

Another aspect of the present invention provides a method for treating hypothyroid neuropathies. Hypothyroidism is sometimes associated with a painful sensory polyneuropathy with axonal degeneration. Mononeuropathy or mononeuropathy multiplex can also occur due to compression of the peripheral nerves by swollen tissues.

The subject method can also be used in the treatment of neuropathies caused by alcohol and toxins. Certain toxins can cause peripheral neuropathy. Lead toxicity is associated with a motor neuropathy. Arsenic and mercury cause a sensory neuropathy. Thallium can cause a sensory and autonomic neuropathy. Several organic solvents and insecticides can also cause polyneuropathy. Alcohol is directly toxic to nerves and alcohol abuse is a major cause of neuropathy. The subject method can be used, in certain embodiments, as part of a broader detoxification program.

In still another embodiment, the methods and compositions of the present invention can be used for the treatment of neuropathies caused by drugs. Several drugs are known to cause neuropathy. They include, among others, vincristine and cisplatinum in cancer, nitrofurantoin, which is used in pyelonephritis, amiodarone in cardiac arrhythmias, disulfuram in alcoholism, ddC and ddI in AIDS, and dapsone which is used to treat leprosy. As above, the subject method can be used, in certain embodiments, as part of a broader detoxification program.

The method of the present invention can also be used in the treatment of neuropathies caused by trauma or compression. Localized neuropathies can result from compression of nerves by external pressure or overlying tendons and other tissues. The best known of these are the carpal tunnel syndrome which results from compression at the wrist, and cervical or lumbar radiculopathies (sciatica), which result from compression of nerve roots as they exit the spine. Other common areas of nerve compression include the elbows, armpits, and the back of the knees.

The subject method is also useful in variety of idiopathic neuropathies. The term "idiopathic" is used whenever the cause of the neuropathy cannot be found. In these cases, the neuropathy is classified according to its manifestations, i.e., sensory, motor, or sensorimotor idiopathic polyneuropathy.

Another aspect of the invention provides a conjoint therapy wherein one or more other therapeutic agents are administered with the subject compound. Such conjoint treatment may be achieved by way of the simultaneous, sequential or separate dosing of the individual components of the treatment. Conjoint administration thus includes administration as part of the same pharmaceutical preparation, simultaneous administration of separate pharmaceutical preparations, as well as administration of separate pharmaceutical preparations at different times on the same day, adjacent days, or otherwise as part of a single therapeutic regimen. For example, the subject method can be carried out conjointly with other neuroprotective agents. The dosages recited herein would be adjusted to compensate for such additional components in the therapeutic composition. Progress of the treated patient can be monitored by conventional methods.

In yet other embodiments, the subject method can be carried out conjointly with the administration of growth and/or trophic factors. For instance, the combinatorial therapy can include a trophic factor such as glial cell line-derived neurotrophic factor, nerve growth factor, cilliary neurotrophic factor, schwanoma-derived growth factor, glial growth factor, striatal-derived neuronotrophic factor, platelet-derived growth factor, brain-derived neurotrophic factor (BDNF), and scatter factor (HGF-SF). Antimitogenic agents can also be used, as for example, cytosine, arabinoside, 5-fluorouracil, hydroxyurea, and methotrexate.

Determination of a therapeutically effective amount and/or a prophylactically effective amount of a subject compound, e.g., to be adequately neuroprotective, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician, the severity of the condition being treated, the risk of further degeneration to the CNS, and the particular agent being employed. In determining the therapeutically effective trophic amount or dose, and/or the prophylactically effective amount or dose, a number of factors are considered by the attending clinician, including, but not limited to: the specific cause of the degenerative state and its likelihood of recurring or worsening; pharmacodynamic characteristics of the particular agent and its mode and route of administration; the desired time course of treatment; the species of mammal; its size, age, and general health; the response of the individual patient; the particular compound administered; the bioavailability characteristics of the preparation administered; the dose regimen selected; the kind of concurrent treatment (i.e., the interaction of the subject compound with other co-administered therapeutics); and other relevant circumstances.

Treatment can be initiated with smaller dosages that are less than the optimum dose of the agent. Thereafter, the dosage should be increased by small increments until the optimum effect under the circumstances is reached. For convenience, the total daily dosage may be divided and administered in portions during the day if desired. A therapeutically effective trophic amount and a prophylactically effective neuroprotective amount of a subject compound, for instance, is expected to vary from concentrations about 0.1 nanogram per kilogram of body weight per day (ng/kg/day) to about 100 mg/kg/day.

Compounds which are determined to be effective for the prevention or treatment of degeneration of dopaminergic neurons and motoneurons and the like in animals, e.g., dogs, rodents, may also be useful in treatment of disorders in humans. Those skilled in the art of treating in such disorders in humans will be guided, from the data obtained in animal studies, to the correct dosage and route of administration of the compound to humans. In general, the determination of dosage and route of administration in humans is expected to be similar to that used to determine administration in animals.

The identification of those patients who are in need of prophylactic treatment for disorders marked by degeneration of dopaminergic neurons and/or motoneurons is well within the ability and knowledge of one skilled in the art. Certain of the methods for identification of patients that are at risk and that can be treated by the subject method are appreciated in the medical arts, such as family history of the development of a particular disease state and the presence of risk factors associated with the development of that disease state in the subject patient. A clinician skilled in the art can readily identify such candidate patients, by the use of, for example, clinical tests, physical examination and medical/family history.

IV. Exemplary Compounds

Compounds suitable for use in the various compositions and methods of the invention include compounds having a structure represented in general Formula I:

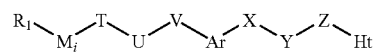

wherein, as valence and stability permit,

M represents, independently for each occurrence, a heteroatom or a substituted or unsubstituted methylene group, such as —$CH_2$—, —CHF—, —CHOH—, —CH(Me)—, —C(=O)—, etc., or two M taken together represent substituted or unsubstituted ethene or ethyne;

R, independently for each occurrence, represents H or lower alkyl, preferably H;

T and V, independently, are absent or represent —N(R)—, —O—, —S—, or —Se—, preferably N(R), O, or S, most preferably N(R);

U and Y, independently, represent —C(=O)—, —C(=S)—, —$S(O_2)$—, —S(O)—, or a methylene group optionally substituted with 1-2 C1-C2 lower alkyl groups, preferably —C(=O)—, —C(=S)—, or —$S(O_2)$—;

X and Z, independently, are absent or represent —N(R)—, —O—, —S—, or —Se—, preferably N(R), O, or S, most preferably N(R);

$R_1$ represents a substituted or unsubstituted alkyl, heteroalkyl, carbocyclic aliphatic, heterocyclic aliphatic, aryl, or heteroaryl group;

Ar represents a substituted or unsubstituted aryl or heteroaryl group;

Ht represents a substituted or unsubstituted heterocyclic aliphatic or heteroaryl group, preferably having a nitrogen member atom; and i represents an integer from 0 to 4, preferably from 0 to 2.

Certain compounds of Formula I suitable for use in the various compositions and methods of the invention have a structure represented in general Formula II:

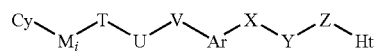

wherein, as valence and stability permit,

M represents, independently for each occurrence, a heteroatom or a substituted or unsubstituted methylene group, such as —$CH_2$—, —CHF—, —CHOH—, —CH(Me)—, —C(=O)—, etc., or two M taken together represent substituted or unsubstituted ethene or ethyne;

R, independently for each occurrence, represents H or lower alkyl, preferably H;

T and V, independently, are absent or represent —N(R)—, —O—, —S—, or —Se—, preferably N(R), O, or S, most preferably N(R);

U and Y, independently, represent —C(=O)—, —C(=S)—, —S(O$_2$)—, —S(O)—, or a methylene group optionally substituted with 1-2 C1-C2 lower alkyl groups, preferably —C(=O)—, —C(=S)—, or —S(O$_2$)—;

X and Z, independently, are absent or represent —N(R)—, —O—, —S—, or —Se—, preferably N(R), O, or S, most preferably N(R);

Cy represents a substituted or unsubstituted carbocyclic aliphatic, heterocyclic aliphatic, aryl, or heteroaryl group;

Ar represents a substituted or unsubstituted aryl or heteroaryl group;

Ht represents a substituted or unsubstituted heterocyclic aliphatic or heteroaryl group, preferably having a nitrogen member atom; and i represents an integer from 0 to 4, preferably from 0 to 2.

In certain embodiments of the above formulae, each of TUV and XYZ, independently, comprises an amide, ester, or sulfonamide linkage. In certain such embodiments, TUV comprises an amide (e.g., T is absent, U represents a carbonyl, and V represents N(R)), and XYZ comprises a sulfonamide (e.g., X is absent, Y represents a sulfonyl, and Z represents N(R)). In certain embodiments, R is H for all occurrences. In certain embodiments, X and Z are absent, and Ht represents a heterocyclic aliphatic ring, such as a piperidino, morpholino, or piperazinyl ring, e.g., forming an amide or sulfonamide with Y.

In certain embodiments of the above formulae, Cy represents a substituted or unsubstituted aryl or heteroaryl group, preferably a monocyclic group. In certain embodiments, substituents on Cy are selected from halogen, lower alkyl, lower heteroalkyl, azide, lower haloalkyl, hydroxyl, lower acyl, amine, amide, cyano, nitro, azido, sulfhydryl, sulfate, sulfonate, sulfamoyl, and sulfonamido, preferably halogen, lower alkyl, lower heteroalkyl, lower haloalkyl, hydroxyl, lower acyl, amine, amide, cyano, and nitro.

In certain embodiments, Ar is a phenyl ring, wherein V and X are preferably disposed in a para relationship. In certain embodiments, Ar is otherwise unsubstituted, while in other embodiments, additional substituents on Ar are selected from amino, hydroxyl, halogen, lower alkyl, and lower heteroalkyl.

In certain embodiments, Ht represents a nitrogen-containing heteroaryl ring, such as oxazole, thiazole, imidazole, or pyridyl, preferably oxazole or thiazole.

In certain embodiments, M$_i$ is absent (i.e., i=0) or represents a heteroalkyl or alkyl chain having from 1-3 member atoms.

In certain embodiments, the present invention contemplates the use of compounds having a structure represented in Formula III:

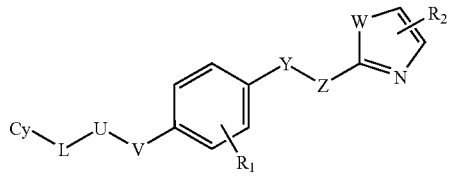

wherein, as valence and stability permit,

L is absent or represents C1-C3 alkyl or heteroalkyl;

V represents N(R), O, or S, preferably N(R);

U and Y, independently, represent —C(=O)—, —C(=S)—, —S(O$_2$)—, —S(O)—, or a methylene group optionally substituted with 1-2 C1-C2 lower alkyl groups, preferably —C(=O)—, —C(=S)—, or —S(O$_2$)—;

W represents NH, O, or S, preferably O or S;

Z represents —N(R)—, —O—, —S—, or —Se—, preferably N(R), O, or S, most preferably N(R);

Cy represents a substituted or unsubstituted carbocyclic aliphatic, heterocyclic aliphatic, aryl, or heteroaryl group; and R$_1$ is absent or represents from 1 to 4 substituents on the ring to which it is attached, such as halogen, alkyl, alkenyl, alkynyl, azide, haloalkyl, hydroxyl, carbonyl (such as carboxyl, alkoxycarbonyl, formyl, ketone, or acyl), thiocarbonyl (such as thioester, thioacetate, or thioformate), alkoxyl, phosphoryl, phosphonate, phosphinate, amine, amide, amidine, imine, cyano, nitro, azido, sulfhydryl, alkylthio, sulfate, sulfonate, sulfamoyl, sulfonamido, sulfonyl, silyl, ether, cycloalkyl, heterocyclyl, heteroalkyl, heteroalkenyl, and heteroalkynyl, heteroaralkyl, aralkyl, aryl or heteroaryl; and R$_2$ is absent or represents from 1 to 2 substituents on the ring to which it is attached, selected from halogen, lower alkyl, lower haloalkyl, hydroxyl, formyl, acetyl, thiocarbonyl, lower alkoxyl, amine, amide, cyano, nitro, lower alkylthio, sulfate, and sulfamoyl, preferably from halogen, lower alkyl, lower haloalkyl, hydroxyl, acetyl, methoxy, amine, and cyano, most preferably from halogen, lower alkyl, and lower haloalkyl.

In certain embodiments, R$_1$ is selected from halogen, hydroxyl, amino, lower alkyl, and lower heteroalkyl. In certain embodiments, R$_1$ is absent.

In certain embodiments, R$_2$ is selected from halogen, hydroxyl, amino, lower alkyl, and lower heteroalkyl. In certain embodiments, R$_2$ is absent.

In certain embodiments, UV taken together represent amine or thioamide, preferably amide, and YZ taken together represent sulfonamide.

In certain embodiments, Cy represents a substituted or unsubstituted aryl or heteroaryl group, preferably a monocyclic group. In certain embodiments, substituents on Cy are selected from halogen, lower alkyl, lower heteroalkyl, azide, lower haloalkyl, hydroxyl, lower acyl, amine, amide, cyano, nitro, azido, sulfhydryl, sulfate, sulfonate, sulfamoyl, and sulfonamido, preferably halogen, lower alkyl, lower heteroalkyl, lower haloalkyl, hydroxyl, lower acyl, amine, amide, cyano, and nitro.

Certain compounds of Formula I suitable for use in the various compositions and methods of the invention have a structure represented in general Formula IV:

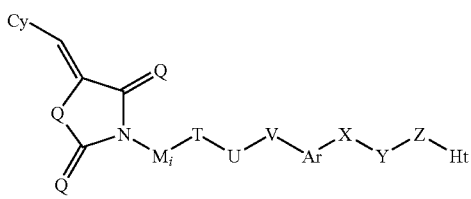

wherein, as valence and stability permit,

M represents, independently for each occurrence, a heteroatom or a substituted or unsubstituted methylene group, such as —CH$_2$—, —CHF—, —CHOH—, —CH(Me)—, —C(=O)—, etc., or two M taken together represent substituted or unsubstituted ethene or ethyne;

Q represents, independently for each occurrence, O or S, preferably O;

R, independently for each occurrence, represents H or lower alkyl, preferably H;

T and V, independently, are absent or represent —N(R)—, —O—, —S—, or —Se—, preferably N(R), O, or S, most preferably N(R);

U and Y, independently, represent —C(═O)—, —C(═S)—, —S(O$_2$)—, —S(O)—, or a methylene group optionally substituted with 1-2 C1-C2 lower alkyl groups, preferably —C(═O)—, —C(═S)—, or —S(O$_2$)—;

X and Z, independently, are absent or represent —N(R)—, —O—, —S—, or —Se—, preferably N(R), O, or S, most preferably N(R);

Cy represents a substituted or unsubstituted carbocyclic aliphatic, heterocyclic aliphatic, aryl, or heteroaryl group;

Ar represents a substituted or unsubstituted aryl or heteroaryl group;

Ht represents a substituted or unsubstituted heterocyclic aliphatic or heteroaryl group, preferably having a nitrogen member atom; and i represents an integer from 0 to 4, preferably from 0 to 2.

In certain embodiments, each of TUV and XYZ, independently, comprises an amide, ester, or sulfonamide linkage. In certain such embodiments, TUV comprises an amide (e.g., T is absent, U represents a carbonyl, and V represents N(R)), and XYZ comprises a sulfonamide (e.g., X is absent, Y represents a sulfonyl, and Z represents N(R)). In certain embodiments, R is H for all occurrences. In certain embodiments, X and Z are absent, and Ht represents a heterocyclic aliphatic ring, such as a piperidino, morpholino, or piperazinyl ring, e.g., forming an amide or sulfonamide with Y.

In certain embodiments, Cy represents a substituted or unsubstituted aryl or heteroaryl group, preferably a monocyclic group. In certain embodiments, substituents on Cy are selected from halogen, lower alkyl, lower heteroalkyl, azide, lower haloalkyl, hydroxyl, lower acyl, amine, amide, cyano, nitro, azido, sulfhydryl, sulfate, sulfonate, sulfamoyl, and sulfonamido, preferably halogen, lower alkyl, lower heteroalkyl, lower haloalkyl, hydroxyl, lower acyl, amine, amide, cyano, and nitro.

In certain embodiments, Ar is a phenyl ring, wherein V and X are preferably disposed in a para relationship. In certain embodiments, Ar is otherwise unsubstituted, while in other embodiments, additional substituents on Ar are selected from amino, hydroxyl, halogen, lower alkyl, and lower heteroalkyl.

In certain embodiments, Ht represents a nitrogen-containing heteroaryl ring, such as oxazole, thiazole, imidazole, or pyridyl, preferably oxazole or thiazole.

In certain embodiments, M$_i$ is absent (i.e., i═0) or represents a heteroalkyl or alkyl chain having from 1-3 member atoms.

Representative examples of compounds encompassed by the above formulae that are useful in the compositions and methods of the present invention include the following molecular structures, identified (ID) as compounds A-D"" whose bioactivities are shown in Table 1:

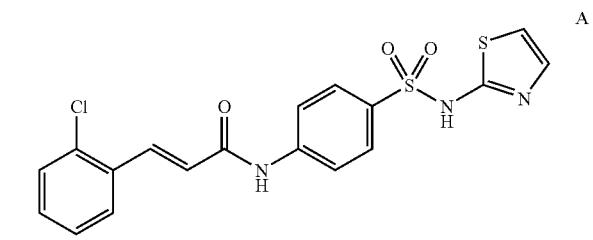

A

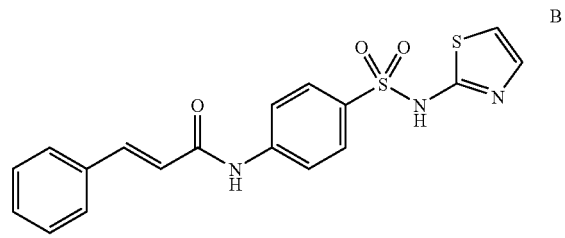

B

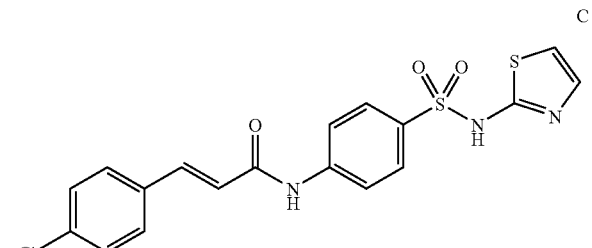

C

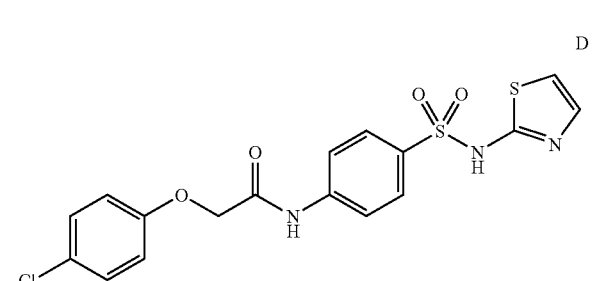

D

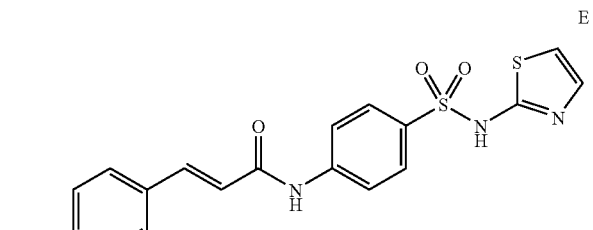

E

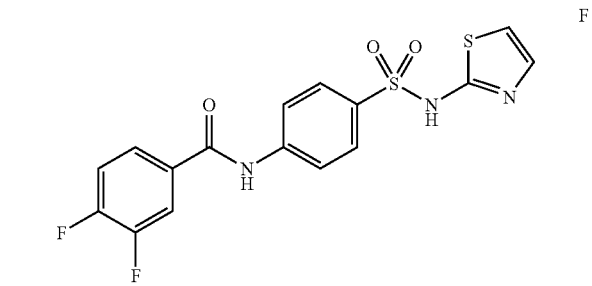

F

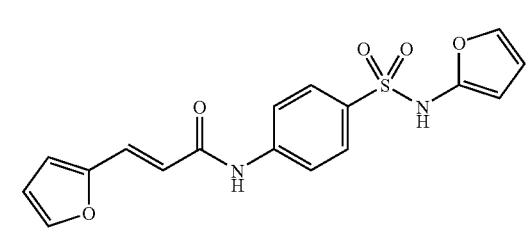
G
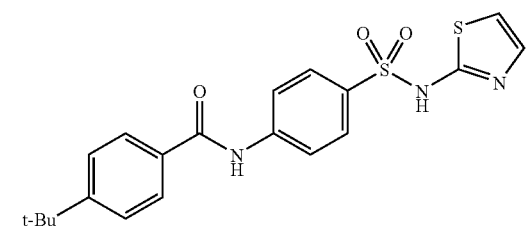
H
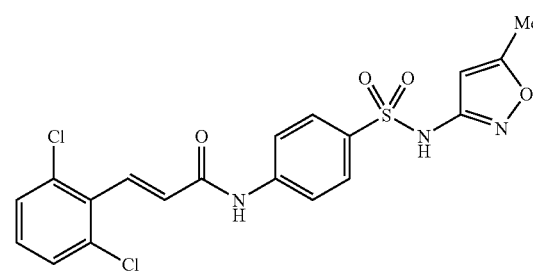
I
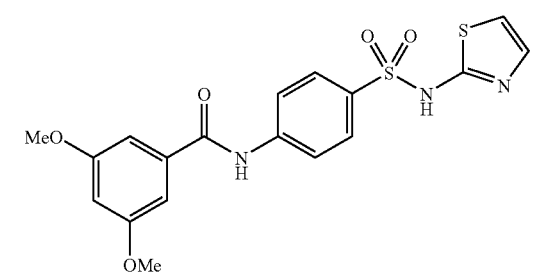
J
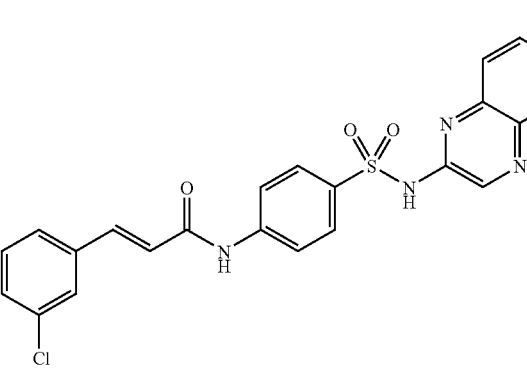
K
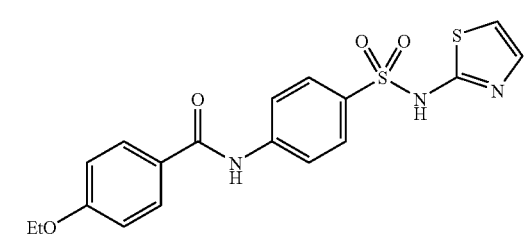
L
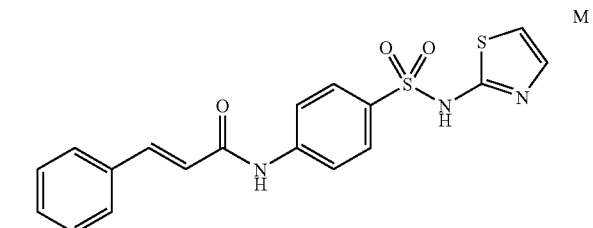
M
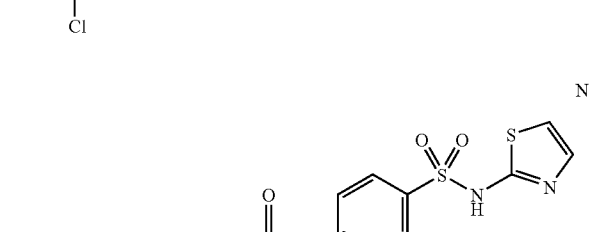
N
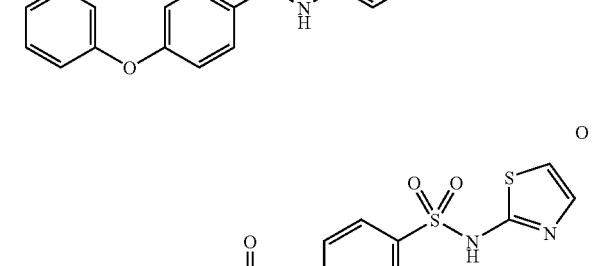
O
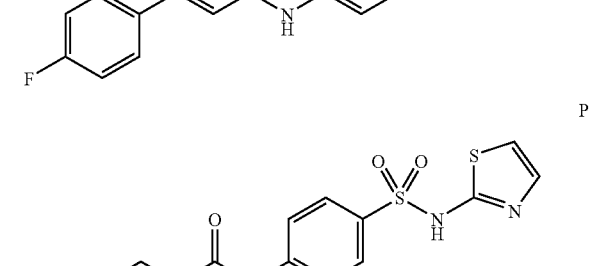
P
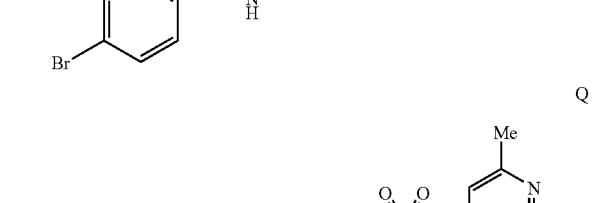
Q
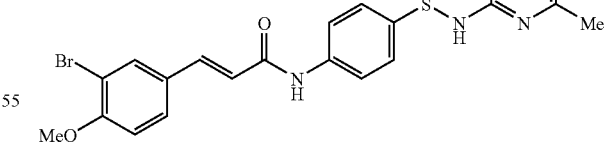
R

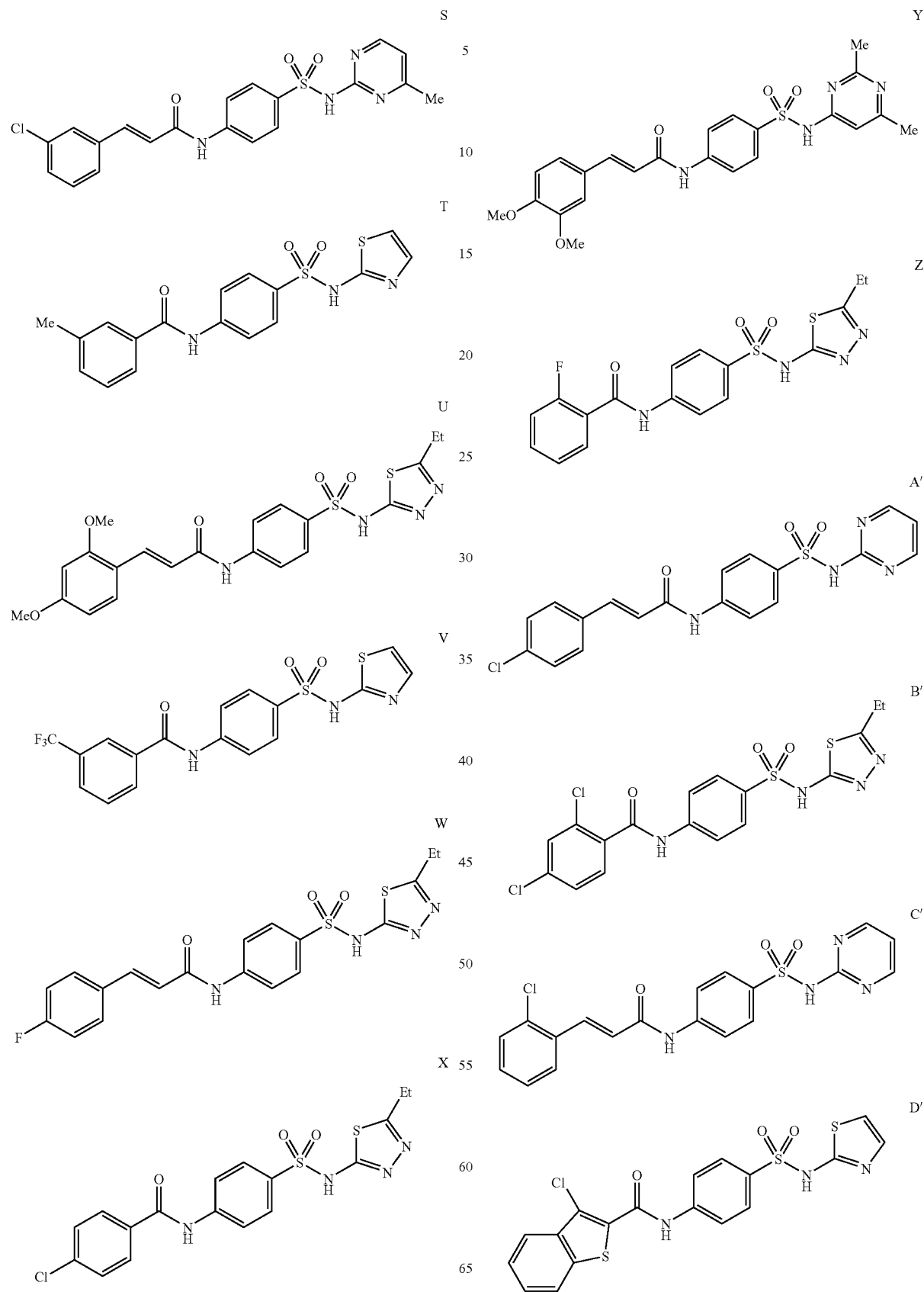

E'
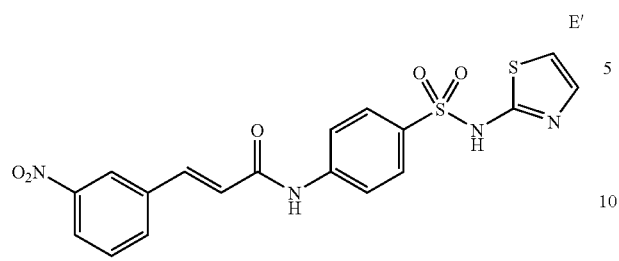
F'
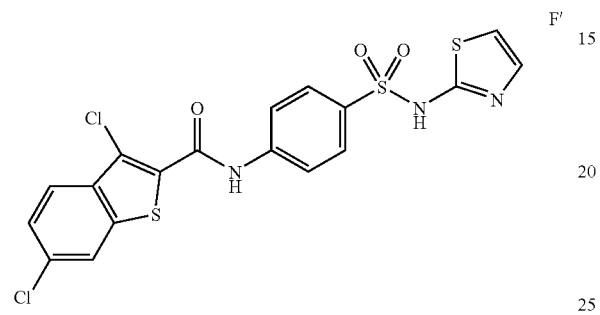
G'
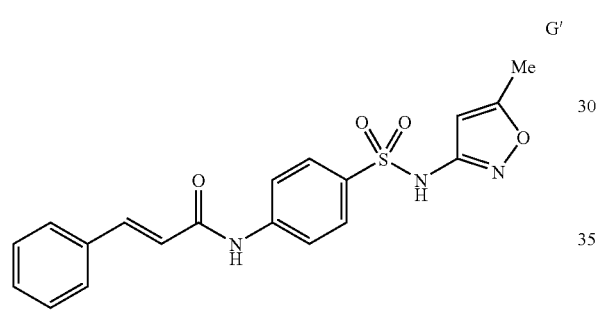
H'
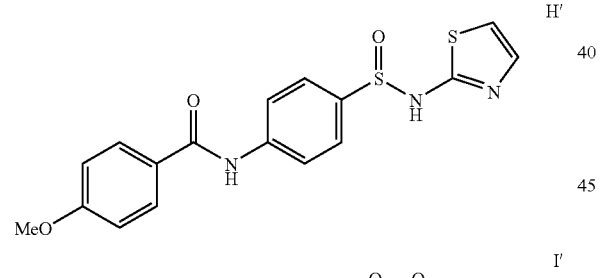
I'
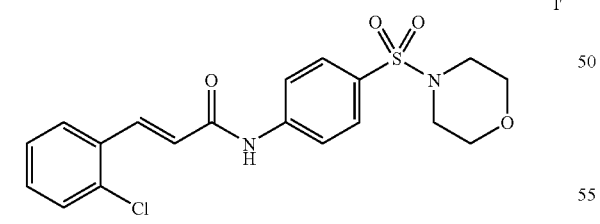
J'
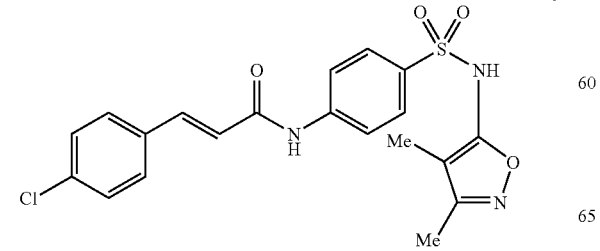
K'
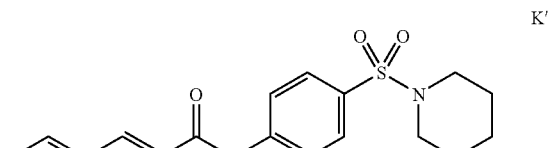
L'
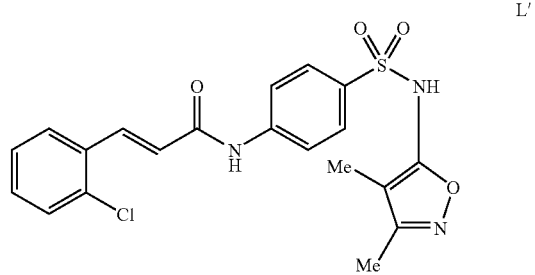
M'
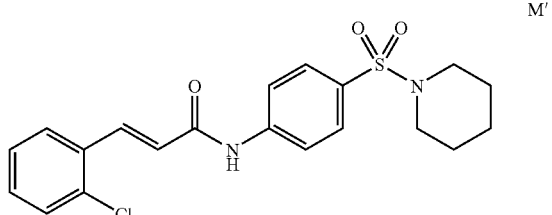
N'
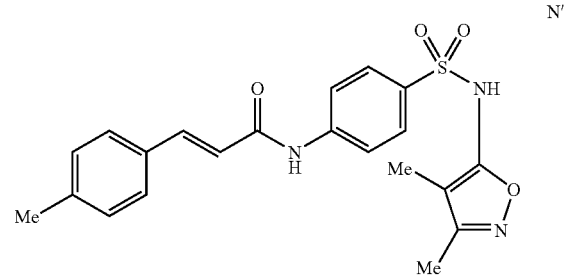
O'
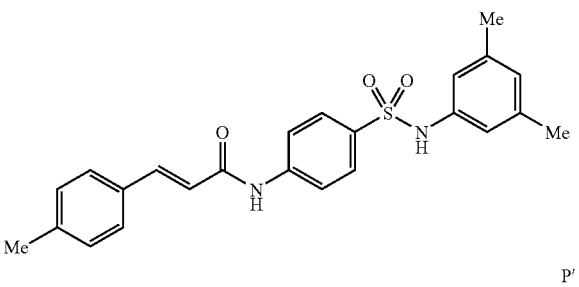
P'
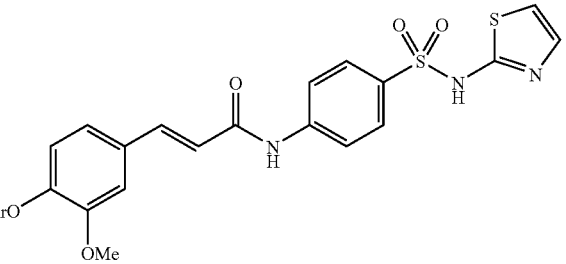

-continued
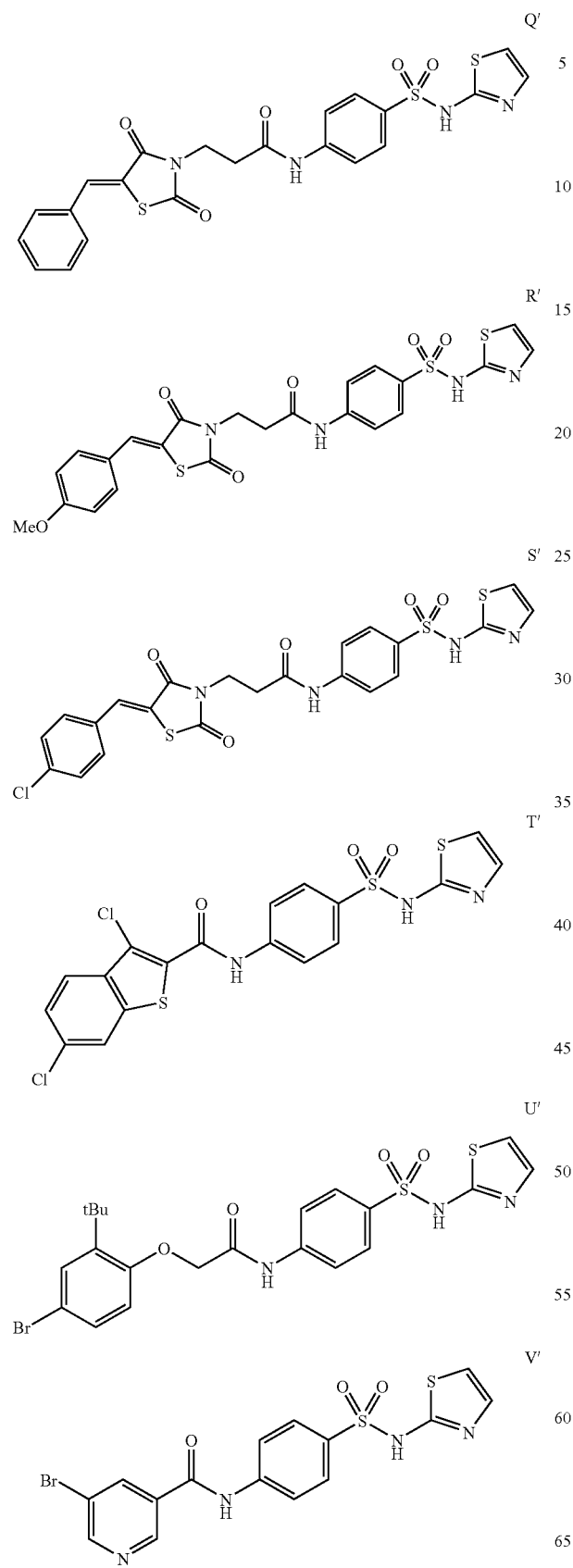
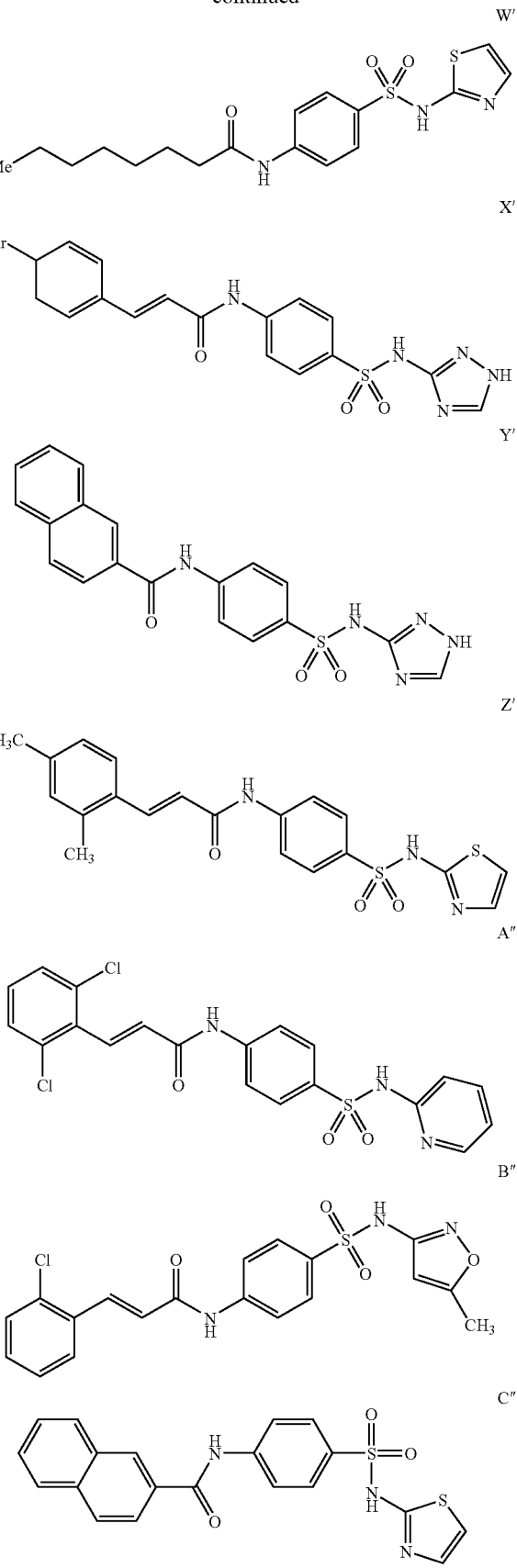

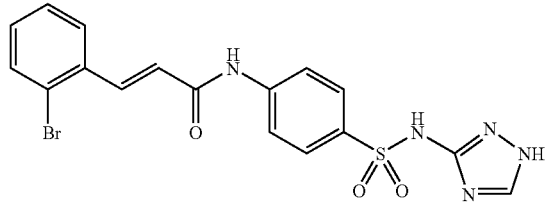
D″
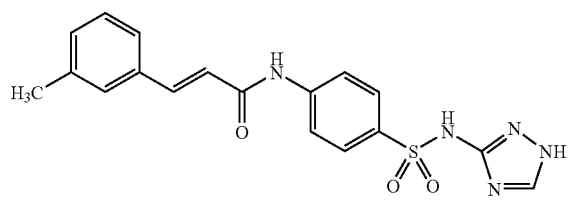
E″
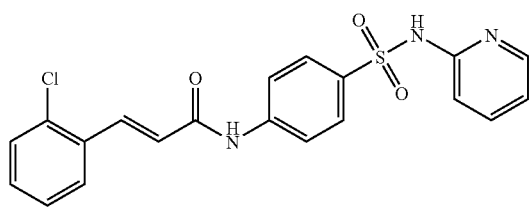
F″
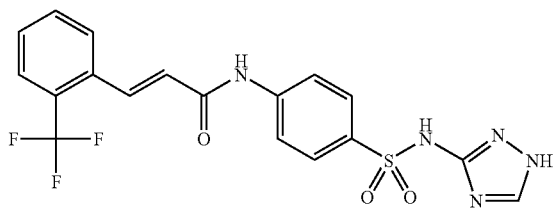
G″
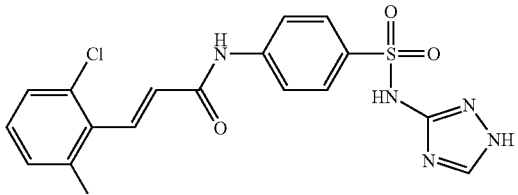
H″
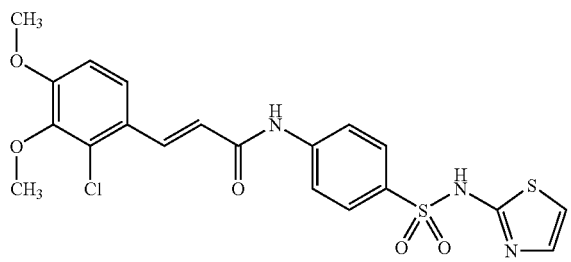
I″
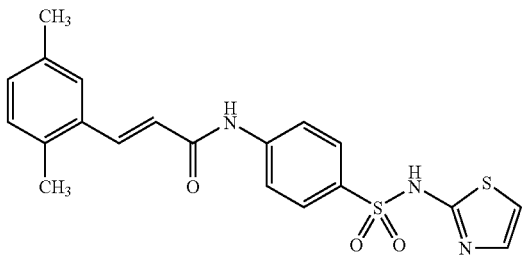
J″
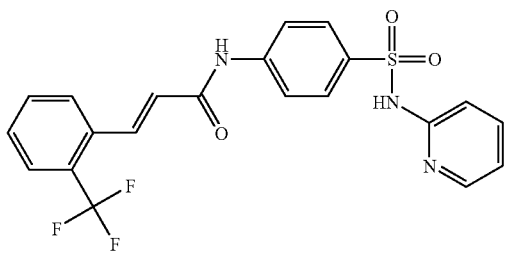
K″
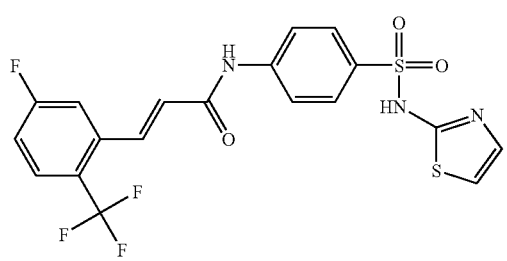
L″
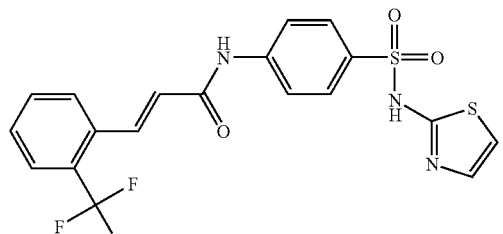
M″
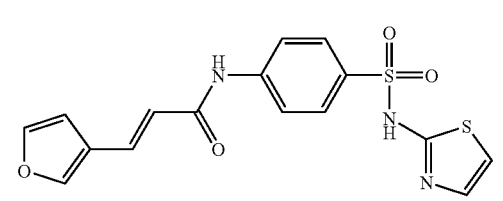
N″
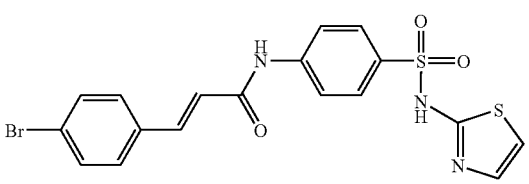
O″

-continued

-continued

-continued
R''''
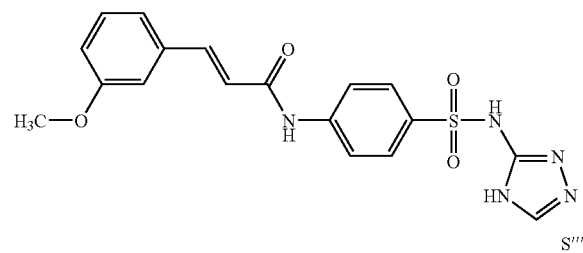
S''''
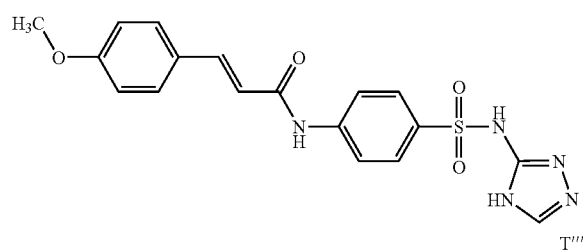
T''''
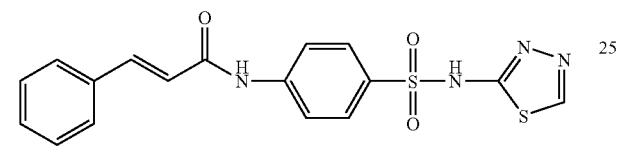
U''''
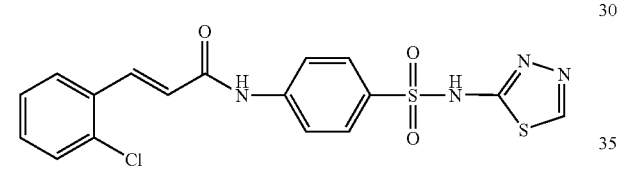
V''''
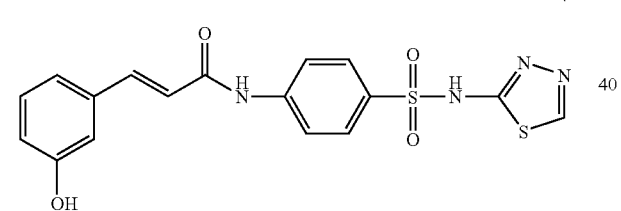
W''''
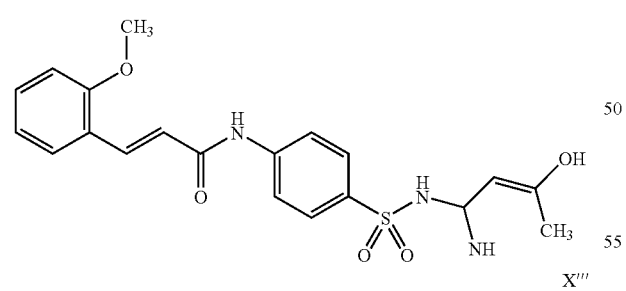
X''''
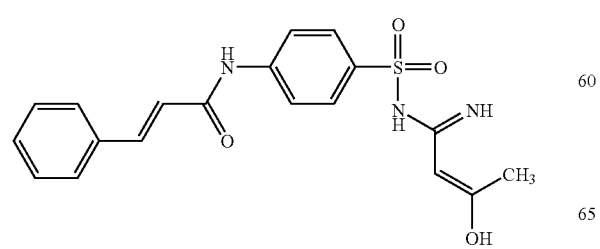
-continued
Y''''
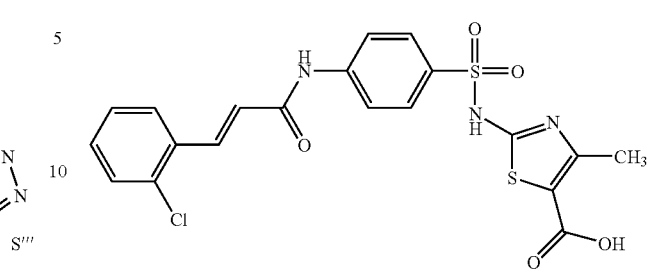
Z''''
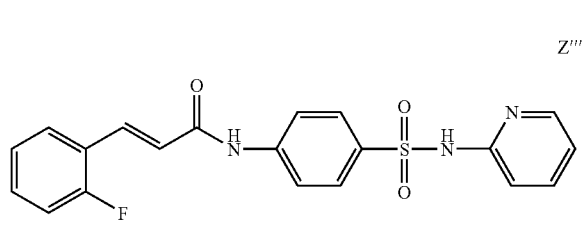
A''''
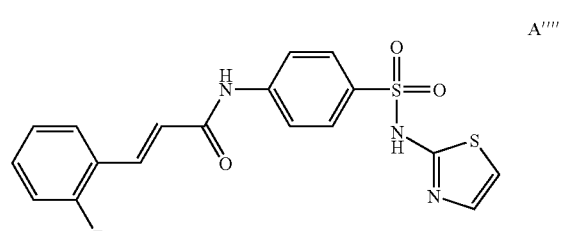
B''''
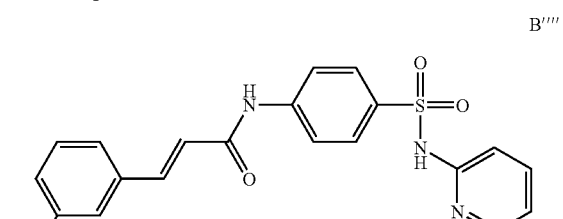
C''''
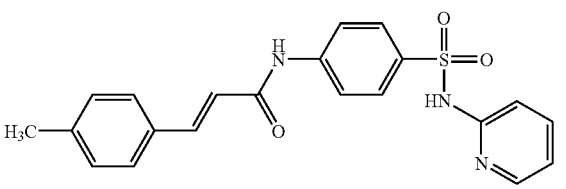
D''''
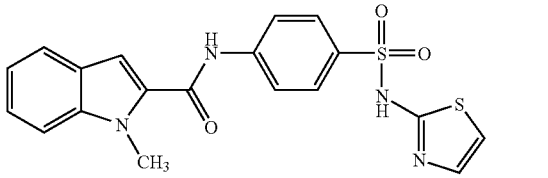
E''''
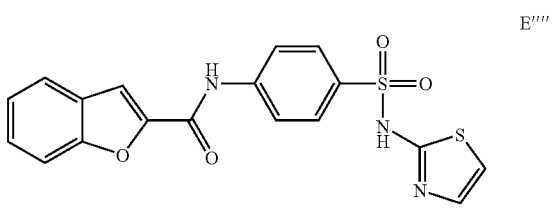

-continued
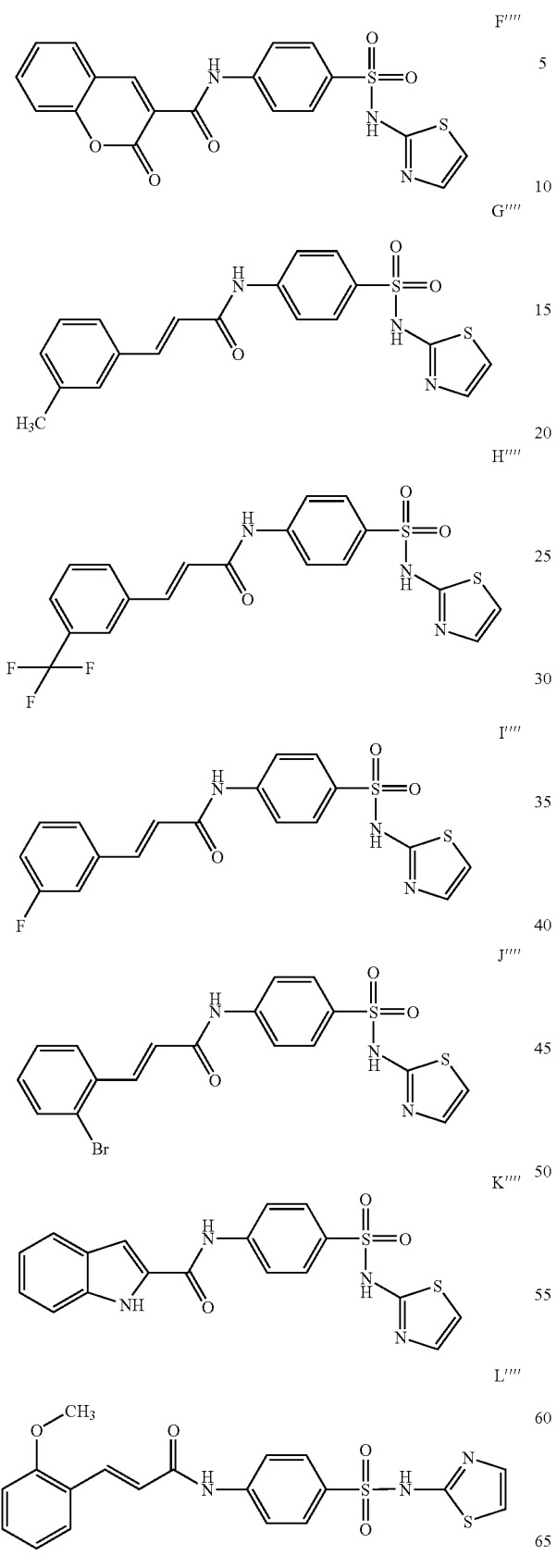
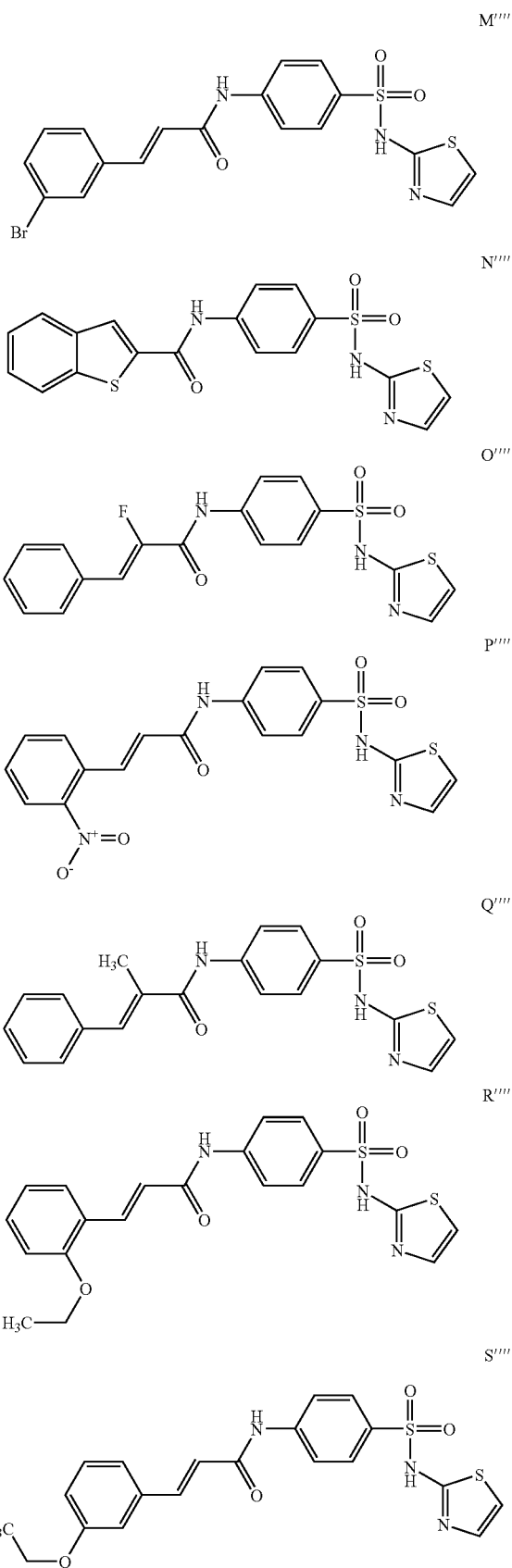

V. Exemplary Assays

Cell-based functional assays can be employed for identifying additional compounds such as those disclosed herein which exhibit similar or analogous therapeutic activity. Suitable assays are cited and described in the Exemplification below.

Potential therapeutic compounds, such as described above, can be tested by any of number of well known animal disease models. For instance, regarding Parkinson's disease, selected agents can be evaluated in animals treated with MPTP. The compound MPTP (1-methyl-4-phenyl-1,2,3,6-tetrahydropyridine) and its metabolite MPP$^+$ have been used to induce experimental parkinsonism. MPP$^+$ kills dopaminergic neurons in the substantia nigra, yielding a reasonable model of late parkinsonism. Turski et al., (1991) Nature 349:414.

Other models of Parkinson's disease are known in the art, such as the 6-hydroxydopamine model (6-OHDA) and the axotomy model. In the former model, a nigral cell body lesion is produced by injecting 6-OHDA unilaterally into the rat medial forebrain bundle. In the latter, nigral neurons were induced to degenerate by transecting their axons within the medial forebrain bundle. These models are described in Lin, *Promega Neural Notes* 1996, 11, 3-7, and references cited therein.

VI. Exemplary Pharmaceutical Preparations

While it is possible for a compound of the present invention to be administered alone, it is preferable to administer the compound as a pharmaceutical formulation (composition). The compounds of the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intrathecal, intracerebroventricular, intramuscular, or intravenous injection as, for example, a sterile solution or suspension, including administration using a minipump or other mechanical-assisted delivery, such as ALZET osmotic pumps that continuously deliver agents at controlled rates; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase 'therapeutically effective amount' as used herein means that amount of a compound, material, or composition comprising a compound of the present invention which is effective for producing some desired therapeutic effect in at least a sub-population of cells in an animal and thereby blocking the biological consequences of that pathway in the treated cells, at a reasonable benefit/risk ratio applicable to any medical treatment.

The phrase 'pharmaceutically acceptable' is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase 'pharmaceutically acceptable carrier' as used herein means a pharmaceutically acceptable material, composition or vehicle, such as a liquid or solid filler, diluent, excipient, solvent or encapsulating material, involved in carrying or transporting the subject compounds from one organ, or portion of the body, to another organ, or portion of the body. Each carrier must be 'acceptable' in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain subject compounds may contain a basic functional group, such as amino or alkylamino, and are, thus, capable of forming pharmaceutically acceptable salts with pharmaceutically acceptable acids. The term 'pharmaceutically acceptable salts' in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term 'pharmaceutically acceptable salts' in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in microencapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" 0 and B books, Corvallis, Ore., U.S.A., 1977).

VII. Synthetic Schemes and Identification of Active Compounds a. Combinatorial Libraries The compounds of the present invention, particularly libraries of variants having various representative classes of substituents, are amenable to combinatorial chemistry and other parallel synthesis schemes (see, for example, PCT WO 94/08051). The result is that large libraries of related compounds, e.g., a variegated library of compounds represented above, can be screened rapidly in high throughput assays in order to identify potential lead compounds, as well as to refine the specificity, toxicity, and/or cytotoxic-kinetic profile of a lead compound.

Simply for illustration, a combinatorial library for the purposes of the present invention is a mixture or set of chemically related compounds that may be screened together for a desired property. The preparation of many related compounds in a single reaction greatly reduces and simplifies the number of screening processes that need to be carried out. Screening for the appropriate physical properties can be done by conventional methods.

schemes, and for certain substitutions on the various substituents of the subject compounds, one of skill in the art will recognize the need for masking certain functional groups with a suitable protecting group. Such techniques are well known in the art and are easily applied to combinatorial synthesis schemes.

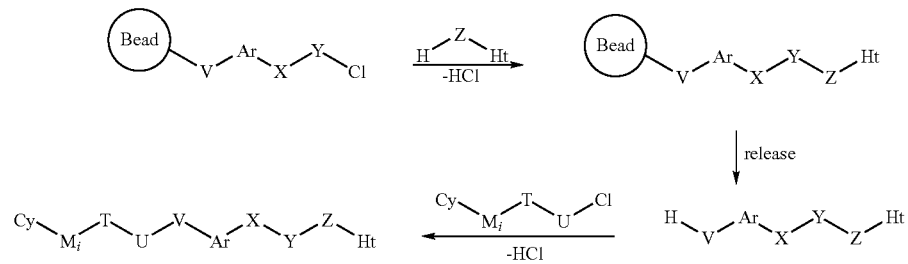

Diversity in the library can be created at a variety of different levels. For instance, the substrate aryl groups used in the combinatorial reactions can be diverse in terms of the core aryl moiety, e.g., a variegation in terms of the ring structure, and/or can be varied with respect to the other substituents.

A variety of techniques are available in the art for generating combinatorial libraries of small organic molecules such as the subject compounds. See, for example, Blondelle et al. (1995) *Trends Anal. Chem.* 14:83; the Affymax U.S. Pat. Nos. 5,359,115 and 5,362,899: the Ellman U.S. Pat. No. 5,288,514: the Still et al. PCT publication WO 94/08051; the ArQule U.S. Pat. Nos. 5,736,412 and 5,712,171; Chen et al. (1994) *JACS* 116:2661: Kerr et al. (1993) *JACS* 115:252; PCT publications WO92/10092, WO93/09668 and WO91/07087; and the Lerner et al. PCT publication WO93/20242). Accordingly, a variety of libraries on the order of about 100 to 1,000,000 or more diversomers of the subject compound scan be synthesized and screened for particular activity or property.

In an exemplary embodiment, a library of candidate compounds diversomers can be synthesized utilizing a scheme adapted to the techniques described in the Still et al. PCT publication WO 94/08051, e.g., being linked to a polymer bead by a hydrolyzable or photolyzable group, optionally located at one of the positions of the candidate compounds or a substituent of a synthetic intermediate. According to the Still et al. technique, the library is synthesized on a set of beads, each bead including a set of tags identifying the particular diversomer on that bead.

The structures of the compounds useful in the present invention lend themselves readily to efficient synthesis. The nature of the structures of the subject compounds, as generally set forth above, allows the rapid combinatorial assembly of such compounds. For example, as depicted below, solid phase routes can be employed to rapidly assemble a wide variety of structures of Formulae I and II for testing in the assays described herein. The structure of the subject compounds is well suited for such an approach, because the combinations TUV and XYZ, or subsets thereof, can be readily attached using reactions such as those depicted in FIGS. 1-31. These reactions generally are quite mild and have been successfully applied in combinatorial solid-phase synthesis schemes. Furthermore, the wide range of substrates and coupling partners suitable and available for these reactions permits the rapid assembly of large, diverse libraries of compounds for testing in assays as set forth herein. For certain In addition to the coupling steps depicted below, additional steps may be used to elaborate or functionalize the basic structural subunits, such as Ar, Cy, and Ht, while the structures are bound to the solid support. Furthermore, many variations on the above and related pathways permit the synthesis of widely diverse libraries of compounds that can be tested as therapeutics similar or analogous to those disclosed herein, e.g., by forming a T—U bond or X—Y bond as a coupling step, rather than forming the U—V or Y—Z bonds to couple subunits. All of these permutations and variations will be understood by one of skill in the art to be included in the scope of the present invention.

Exemplary reactions useful for generating compounds of Formulae I and II for use in the methods and compositions of the present invention are shown in FIGS. 1-31. The reaction conditions in the illustrated schemes of FIG. 1-31 are as follows:

1) $R_1CH_2CN$, $NaNH_2$, toluene
 (Arzneim-Forsch, 1990, 40, 11, 1242)
2) $H_2SO_4$, $H_2O$, reflux
 (Arzneim-Forsch, 1990, 40, 11, 1242)
3) $H_2SO_4$, EtOH, reflux
 (Arzneim-Forsch, 1990, 40, 11, 1242)
4) NaOH, EtOH, reflux
5) $(Boc)_2O$, 2M NaOH, THF
6) LiHDMS, $R_1X$, THF
 (Merck Patent Applic # WO 96/06609)
7) Pd—C, $H_2$, MeOH
8) t-BuONO, CuBr, HBr, $H_2O$
 (J. Org. Chem. 1977, 42, 2426)
9) $ArB(OH)_2$, $Pd(PPh_3)_4$, Dioxane
 (J. Med. Chem. 1996, 39, 217-223)
10) $R_{12}(H)C=CR_{13}R_{14}$, $Pd(OAc)_2$, $Et_3N$, DMF
 (Org. React. 1982, 27, 345)
11) $Tf_2O$, THF
 (J. Am. Chem. Soc. 1987, 109, 5478-5486)
12) $ArSnBu_3$, $Pd(PPh_3)_4$, Dioxane
 (J. Am. Chem. Soc. 1987, 109, 5478-5486)
13) $KMnO_4$, Py, $H_2O$
 (J. Med. Chem. 1996, 39, 217-223)
14) $NaOR_1$, THF
15) $NaSR_1$, THF
16) $HNR_1R_{13}$, THF
17) HONO, $NaBF_4$
 (Adv. Fluorine Chem. 1965, 4, 1-30)

18) Pd(OAc)$_2$, NaH, DPPF, PhCH$_3$, R$_{10}$H
   (J. Org. Chem. 1997, 62, 5413-5418)
19) i. R$_1$X, Et$_3$N, CH$_2$Cl$_2$, ii. R$_{13}$X
20) SOCl$_2$, cat DMF
21) CH$_2$N$_2$, Et$_2$O
22) Ag$_2$O, Na$_2$CO$_3$, Na$_2$S$_2$O$_3$, H$_2$O
   (Tetrahedron Lett. 1979, 2667)
23) AgO$_2$CPh, Et$_3$N, MeOH
   (Org. Syn., 1970, 50, 77; J. Am. Chem. Soc. 1987, 109, 5432)
24) LiOH, THF-MeOH
25) (EtO)$_2$P(O)CH$_2$CO$_2$R, BuLi, THF
26) MeO$_2$CCH(Br)=P(Ph)$_3$, benzene
27) KOH or KOtBu
28) Base, X(CH$_2$)$_n$CO$_2$R
29) DPPA, Et$_3$N, toluene
   (Synthesis 1985, 220)
30) HONO, H$_2$O
31) SO$_2$, CuCl, HCl, H$_2$O
   (Synthesis 1969, 1-10, 6)
32) Lawesson's reagent, toluene
   (Tetrahedron Asym. 1996, 7, 12, 3553)
33) R$_2$M, solvent
34) 30% H$_2$O$_2$, glacial CH$_3$CO$_2$H
   (Helv. Chim. Acta. 1968, 349, 323)
35) triphosgene, CH$_2$Cl$_2$
   (Tetrahedron Lett., 1996, 37, 8589)
36) i. (EtO)$_2$P(O)CHLiSO$_2$Oi—Pr, THF, ii. NaI
37) Ph$_3$PCH$_3$I, NaCH$_2$S(O)CH$_3$, DMSO
   (Synthesis 1987, 498)
38) Br$_2$, CHCl$_3$ or other solvent
   (Synthesis 1987, 498)
39) BuLi, Bu$_3$SnCl
40) ClSO$_2$OTMS, CCl$_4$
   (Chem. Ber. 1995, 128, 575-580)
41) MeOH—HCl, reflux
42) LAH, Et$_2$O or LiBH$_4$, EtOH or BH$_3$-THF
   (Tetrahedron Lett., 1996, 37, 8589)
43) MsCl, Et$_3$N, CH$_2$Cl$_2$
   (Tetrahedron Lett., 1996, 37, 8589)
44) Na$_2$SO$_3$, H$_2$O
   (Tetrahedron Lett., 1996, 37, 8589)
45) R$_2$R$_4$NH, Et$_3$N, CH$_2$Cl$_2$
46) R$_2$M, solvent
47) CH$_3$NH(OCH$_3$), EDC, HOBt, DIEA, CH$_2$Cl$_2$ or DMF
   (Tetrahedron Lett, 1981, 22, 3815)
48) MeLi, THF
49) mCPBA, CH$_2$Cl$_2$
50) HONO, Cu$_2$O, Cu(NO$_3$)$_2$, H$_2$O
   (J. Org. Chem. 1977, 42, 2053)
51) RIM, solvent
52) HONO, NaS(S)COEt, H$_2$O
   (Org. Synth. 1947, 27, 81)
53) HSR$_2$ or HSR$_4$, CH$_2$Cl$_2$
54) i-BuOC(O)Cl, Et$_3$N, NH$_3$, THF
55) R$_2$R$_4$NH, CH$_2$Cl$_2$, NaBH(OAc)$_3$
56) R$_2$R$_4$NH, MeOH/CH$_3$CO$_2$H, NaBH$_3$CN
57) R$_2$OH, EDC, HOBt, DIEA, CH$_2$Cl$_2$ or DMF
58) R$_2$OH, HBTU, HOBt, DIEA, CH$_2$Cl$_2$ or DMF
59) R$_2$R$_4$NH, EDC, HOBt, DIEA, CH$_2$Cl$_2$ or DMF
60) R$_2$R$_4$NH, HBTU, HOBt, DIEA, CH$_2$Cl$_2$ or DMF
61) POCl$_3$, Py, CH$_2$Cl$_2$
62) R$_2$R$_4$NCO, solvent
63) R$_2$OC(O)Cl, Et$_3$N, solvent
64) R$_2$CO$_2$H, EDC or HBTU, HOBt, DIEA, CH$_2$Cl$_2$ or DMF
65) R$_2$X, Et$_3$N, solvent
66) (CH$_3$S)$_2$C=N(CN), DMF, EtOH
   (J. Med. Chem. 1994, 37, 57-66)
67) R$_2$SO$_2$Cl, Et$_3$N, CH$_2$Cl$_2$
68) R$_2$— or R$_3$— or R$_4$—CHO, MeOH/CH$_3$CO$_2$H, NaBH$_3$CN
   (Synthesis 1975, 135-146)
69) Boc(Tr)-D or L-CysOH, HBTU, HOBt, DIEA, CH$_2$Cl$_2$ or DMF
70) Boc(Tr)-D or L-CysH, NaBH$_3$CN, MeOH/CH$_3$CO$_2$H
   (Synthesis 1975, 135-146)
71) S-Tr-N-Boc cysteinal, ClCH$_2$CH$_2$Cl or THF, NaBH(OAc)$_3$
   (J. Org. Chem. 1996, 61, 3849-3862)
72) TFA, CH$_2$Cl$_2$, Et$_3$SiH or (3:1:1) thioanisole/ethanedithiol/DMS
73) TFA, CH$_2$Cl$_2$
74) DPPA, Et$_3$N, toluene, HOCH$_2$CH$_2$SiCH$_3$
   (Tetrahedron Lett. 1984, 25, 3515)
75) TBAF, THF
76) Base, TrSH or BnSH
77) Base, R$_2$X or R$_4$X
78) R$_3$NH$_2$, MeOH/CH$_3$CO$_2$H, NaBH$_3$CN
79) N$_2$H$_4$, KOH
80) Pd$_2$(dba)$_3$, P(o-tol)$_3$, RNH$_2$, NaOtBu, Dioxane, R$_1$NH$_2$
   (Tetrahedron Lett. 1996, 37, 7181-7184).
81) Cyanamide.
82) Fmoc-Cl, sodium bicarbonate.
83) BnCOCl, sodium carbonate.
84) AllylOCOCl, pyridine.
85) Benzyl bromide, base.
86) Oxalyl chloride, DMSO.
87) RCONH$_2$.
88) Carbonyldiimidazole, neutral solvents (e.g., DCM, DMF, THF, toluene).
89) Thiocarbonyldiimidazole, neutral solvents (e.g., DCM, DMF, THF, toluene).
90) Cyanogen bromide, neutral solvents (e.g., DCM, DMF, THF, toluene).
91) RCOCl, Triethylamine
92) RNHNH$_2$, EDC.
93) RO$_2$CCOCl, Et$_3$N, DCM.
94) MsOH, Pyridine (J. Het. Chem., 1980, 607.)
95) Base, neutral solvents (e.g., DCM, toluene, THF).
96) H$_2$NOR, EDC.
97) RCSNH$_2$.
98) RCOCHBrR, neutral solvents (e.g., DCM, DMF, THF, toluene), (Org. Proc. Prep. Intl., 1992, 24, 127).
99) CH$_2$N$^2$, HCl. (Synthesis, 1993, 197).
100) NH$_2$NHR, neutral solvents (e.g., DCM, DMF, THF, toluene).
101) RSO$_2$Cl, DMAP. (Tetrahedron Lett., 1993, 34, 2749).
102) Et$_3$N, RX. (J. Org. Chem., 1990, 55, 6037).
103) NOCl or Cl$_2$ (J. Org. Chem., 1990, 55, 3916).
104) H$_2$NOH, neutral solvents (e.g., DCM, DMF, THF, toluene).
105) RCCR, neutral solvents (DCM, THF, Toluene).
106) RCHCHR, neutral solvents (DCM, THF, Toluene).
107) H$_2$NOH, HCl.
108) Thiocarbonyldiimidazole, SiO$_2$ or BF$_3$OEt$_2$. (J. Med. Chem., 1996, 39, 5228).
109) Thiocarbonyldiimidazole, DBU or DBN. (J. Med. Chem., 1996, 39, 5228).
110) HNO$_2$, HCl.
111) ClCH$_2$CO$_2$Et (Org. Reactions, 1959, 10, 143).
112) Morpholine enamine (Eur. J. Med. Chem., 1982, 17, 27).
113) RCOCHR'CN
114) RCOCHR'CO$_2$Et 115) $Na_2SO_3$
116) $H_2NCHRCO_2Et$
117) $EtO_2CCHRNCO$
118) $RCNHNH_2$.
119) $RCOCO_2H$, (J. Med. Chem., 1995, 38, 3741).
120) RCHO, KOAc.
121) 2-Fluoronitrobenzene.
122) $SnCl_2$, EtOH, DMF.
123) RCHO, $NaBH_3CN$, HOAc.
124) $NH_3$, MeOH.
125) $2,4,6-Me_3PhSO_2NH_2$.
126) $Et_2NH$, $CH_2Cl_2$
127) MeOC(O)Cl, $Et_3N$, $CH_2Cl_2$
128) $R_2NH_2$, EDC, HOBT, $Et_3N$, $CH_2Cl_2$
129) DBU, $PhCH_3$
130) $BocNHCH(CH_2STr)CH_2NH_2$, EDC, HOBT, $Et_3N$, $CH_2Cl_2$
131) $R_2NHCH_2CO_2Me$, HBTU, HOBT, $Et_3N$, $CH_2Cl_2$
132) $BocNHCH(CH_2STr)CH_2OMs$, LiHMDS, THF
133) $R_2NHCH_2CO_2Me$, $NaBH(OAc)_3$, $ClCH_2CH_2Cl$ or THF
134) $R_2NHCH_2CH(OEt)_2$, HBTU, HOBT, $Et_3N$, $CH_2Cl_2$
135) $NaBH(OAC)_3$, $ClCH_2CH_2Cl$ or THF, AcOH.
136) Piperidine, DMF.
137) $Pd(Ph_3P)_4$, $Bu_3SnH$.
138) $RCO_2H$, EDC, HOBT, $Et_3N$, DCM.
139) $RNH_2$, neutral solvents.
140) RCHO, $NaBH_3CN$, HOAc.
141) RNCO, solvent.
142) $RCO_2H$, EDC or HBTU, HOBt, DIEA, $CH_2Cl_2$ or DMF.
143) RCOCl, Triethylamine
144) $RSO_2Cl$, $Et_3N$, $CH_2Cl_2$.
145) $SnCl_2$, EtOH, DMF.
146) $RNH_2$, EDC, HOBt, DIEA, $CH_2Cl_2$ or DMF.
147) Dibromoethane, $Et_3N$, $CH_2Cl_2$
148) Oxalyl chloride, neutral solvents.
149) LiOH, THF-MeOH.
150) Carbonyldiimidazole, neutral solvents (e.g., DCM, DMF, THF, toluene).
151) $RNH_2$, $Et_3N$, $CH_2Cl_2$.
152) Base, RX.
153) DBU, $PhCH_3$
154) DPPA, $Et_3N$, toluene (Synthesis 1985, 220)
155) $SOCl_2$, cat DMF.
156) ArH, Lewis Acid ($AlCl_3$, $SnCl_4$, $TiCl_4$), $CH_2Cl_2$.
157) $H_2NCHRCO_2Et$, neutral solvents.
158) $BocHNCHRCO_2H$, EDC OR HBTU, HOBt, DIEA, $CH_2Cl_2$ or DMF.
159) TFA, $CH_2Cl_2$.

VIII. Business Methods

One aspect of the present invention relates to a kit comprising compounds as described herein, e.g., of Formula I, II, III or IV, for promoting survival of substantia nigra neuronal cells, dopaminergic cells, or motoneurons, in a patient, preferably a human, and in association with instructions (written and/or pictorial) describing the use of the formulation for promoting survival of substantia nigra neuronal cells, dopaminergic cells, or motoneurons, and optionally, warnings of possible side effects and drug-drug or drug-food interactions.

Another aspect of the present invention relates to a kit comprising compounds as described herein, e.g., of Formula I, II, III or IV, for treating a disorder characterized by loss of dopaminergic neurons and/or motoneurons, or for treating or preventing Parkinson's disease, or ALS, or limiting damage to neuronal cells by Parkinsonian conditions, in a patient, preferably a human, and in association with instructions (written and/or pictorial) describing the use of the formulation for treating a disorder characterized by loss of dopaminergic neurons and/or motoneurons, or for treating or preventing Parkinson's disease, or ALS, or limiting damage to neuronal cells by Parkinsonian conditions, and optionally, warnings of possible side effects and drug-drug or drug-food interactions.

The invention further contemplates a method for conducting a pharmaceutical business, comprising: (a) manufacturing a pharmaceutical preparation comprising a sterile pharmaceutical excipient and compounds as described herein, e.g., of Formula II or II; and (b) marketing (e.g., providing promotional and/or informative presentations (such as displays, telemarketing, and lectures), products (such as trial samples of the preparation), and/or documentation (including leaflets, pamphlets, websites, posters, etc.)) to healthcare providers, such as doctors, hospitals, clinics, etc., a benefit of using the pharmaceutical preparation for promoting survival of substantia nigra neuronal cells, dopaminergic cells, or motoneurons.

The invention further contemplates a method for conducting a pharmaceutical business, comprising: (a) manufacturing a pharmaceutical preparation comprising a sterile pharmaceutical excipient and compounds as described herein, e.g., of Formula I, II, III or IV; and (b) marketing (e.g., providing promotional and/or informative presentations (such as displays, telemarketing, and lectures), products (such as trial samples of the preparation), and/or documentation (including leaflets, pamphlets, websites, posters, etc.)) to healthcare providers, such as doctors, hospitals, clinics, etc., a benefit of using the pharmaceutical preparation for treating a disorder characterized by loss of dopaminergic neurons and/or motoneurons, or for treating or preventing Parkinson's disease, or ALS, or limiting damage to neuronal cells by Parkinsonian conditions.

Another aspect of the invention provides for a method for conducting a pharmaceutical business, comprising: (a) providing a distribution network for selling the pharmaceutical composition comprising a sterile pharmaceutical excipient and compounds as described herein, e.g., of Formula I, II, III or IV; and (b) providing instruction material to patients or physicians for using the pharmaceutical composition for promoting survival of substantia nigra neuronal cells, dopaminergic cells, or motoneurons.

Another aspect of the invention provides for a method for conducting a pharmaceutical business, comprising: (a) providing a distribution network for selling the pharmaceutical composition comprising a sterile pharmaceutical excipient and compounds as described herein, e.g., of Formula I, II, III or IV; and (b) providing instruction material to patients or physicians for treating a disorder characterized by loss of dopaminergic neurons and/or motoneurons, or for treating or preventing Parkinson's disease, or ALS, or limiting damage to neuronal cells by Parkinsonian conditions.

Another aspect of the invention provides for a method for conducting a pharmaceutical business, comprising: (a) determining an appropriate pharmaceutical preparation and dosage of a compounds as described herein, e.g., of Formula I, II, III or IV, for promoting survival of substantia nigra neuronal cells, dopaminergic cells, or motoneurons; (b) conducting therapeutic profiling of the pharmaceutical preparation for efficacy and toxicity in animals; (c) providing a distribution network for selling a pharmaceutical composition having an acceptable therapeutic profile; and, optionally, (d) providing a sales group for marketing the preparation to healthcare providers.

Yet another aspect of the invention provides for a method for conducting a pharmaceutical business, comprising: (a) determining an appropriate pharmaceutical preparation and dosage of a compounds as described herein, e.g., of Formula I, II, III or IV, for treating a disorder characterized by loss of dopaminergic neurons and/or motoneurons, or for treating or preventing Parkinson's disease, or ALS, or limiting damage to neuronal cells by Parkinsonian conditions; (b) conducting therapeutic profiling of the pharmaceutical preparation for efficacy and toxicity in animals; (c) providing a distribution network for selling a pharmaceutical composition having an acceptable therapeutic profile; and, optionally, (d) providing a sales group for marketing the preparation to healthcare providers.

EXEMPLIFICATION

The invention now being generally described, it will be more readily understood by reference to the following examples, which are included merely for purposes of illustration of certain aspects and embodiments of the present invention, and are not intended to limit the invention.

Parkinson's disease (PD) is characterized by a dysfunction in the dopaminergic activity of the substantia nigra that is caused by neuronal degeneration. This results in a state of dopamine (DA) deficiency causing the movement disorder symptoms including rigidity, tremor bradykinesis, gait difficulty, and postural instability. The most effective treatment for PD to date is the oral administration of the dopamine precursor Levodopa. Levodopa penetrates the central nervous system and is enzymatically converted to dopamine. It is believed that beneficial effects of Levodopa result from increased concentration of dopamine in the brain. Unfortunately, neither Levodopa nor any of the less commonly utilized medications typically stem the progression of the disease, which is caused by the degeneration of dopaminergic neurons in the substantia nigra Neurotrophic activity promotes the survival and maintains the phenotypic differentiation of nerve cells. Hence, neurotrophic molecules may be useful in protecting responsive neurons against a variety of different forms of nerve damages. Neurotrophic molecules specific for midbrain substantia nigra dopaminergic neurons would be of clinical interest because those neurons play an important role in the regulation of motor activity and because progressive degeneration of the substantia nigra dopaminergic neurons is the hallmark of PD. Here, we describe a method for screening small molecule libraries for neurotrophic activity on the embryonic precursors of the substantia nigra dopaminergic neurons that degenerate in PD. This bioassay for identifying neurotrophic activity directed to dopaminergic neurons that may be useful in treating PD is based on an assay previously described (Lin et al, *J. Neurochem* 1994, 63, 758-768) and implemented with modification in the present invention. This bioassay used dissociated cell cultures of embryonic midbrain, where high-affinity dopamine (DA) uptake and expression of tyrosine hydroxylase (TH), the rate-limiting enzyme in DA synthesis, can be used as markers for dopaminergic neuron survival and differentiation. We screened various libraries of natural products and small molecules for trophic activities specific for mesencephalon dopaminergic neurons.

Compound A as depicted above was discovered based on its ability to promote the functional activity and survival in cell culture of dopaminergic nerve cells isolated from the rat embryo mesencephalon, These dopaminergic nerve cells are the embryonic precursor of the dopaminergic nerve cell in the adult substantia nigra that degenerate in PD. Therefore, compound A and related compounds may be useful in reducing the neuronal degeneration that causes the symptoms of PD.

Furthermore, compound A may be useful in treating other forms of damage to or improper function of dopaminergic nerve cells in human patients such as schizophrenia and other forms of psychosis. Current treatments of such conditions require drugs active at dopamine receptors, suggesting that improper function of the dopaminergic neurons enervating these receptor-bearing neuronal populations may be involved in the disease process, Other conditions that may be treated with compound A include those that are caused or contributed to by death or decreased function of dopaminergic neurons.

Methods

Cell Culture

Primary midbrain cultures were prepared from rat embryo ventral mesencephalon as described previously by Lin et al (1994). In brief, rostral mesencephalic tegmentum of embryonic day 16 rat embryos was collected in DMEM/F12 (Hyclone SH30023.01) containing 2 mM glutamine on ice, The tissue was treated with 0.1% trypsin in Hanks' balanced salt solution (HBSS, Gibco 14175-095) for 15 min at 37° C. and dissociated mechanically by mild trituration with a fire-polished glass pipet in growth medium plus 2% heat-inactivated fetal bovine serum (FBS). The growth medium consisted of equal volumes of Dulbecco's minimal essential medium DMEM (Gibco 12100-046) and HAM's F12 nutrient mixture (Gibco 21700-075) supplemented with 33 mM glucose, 13 mM sodium bicarbonate, 5 mM HEPES, 2 mM glutamine, 25 μg/ml insulin, 100 μg/ml transferrin, 60 μM putrescine, 20 nM progesterone, 30 nM sodium selenite, 5 U/ml penicillin G and 5 μg/ml streptomycin. 24-well tissue culture plate was coated by adding 15 μg/ml poly-1-ornithine hydrobromide solution at 0.5 ml/well, incubated at room temperature for 1 hr. The coating solution was removed and the well washed 3 times with distilled water and one wash with HBSS. The dissociated cells were plated onto polyornithine-coated wells at 250,000-350,000 trypan blue-excluding viable cells per well in 500 μl of above medium containing 1% FBS. After 3 h when most of the cells had adhered to the bottom of the well, the medium was replaced with 500 μl of fresh medium without FBS. A serial dilution of the sample to be assayed for trophic activity was added to each well in duplicate at the time of medium change or within 24 h thereafter. Unless otherwise stated, cultures were incubated at 37° C. without any further medium change up to 7 days. Primary hindbrain cultures were prepared as described for the midbrain cultures except that the rostral raphe region (instead of the rostral mesencephalon) was dissected and trypsinized for 20 (instead of 15) min.

Dopamine (DA) Uptake Assay

[$^3$H]DA uptake was measured in cultures at day 7, and all the solutions were maintained at 37° C. The growth medium was removed, and the cultures were rinsed twice with 0.25 ml of uptake buffer, which consists of HBSS (Gibco 11201-092) supplemented with 28 mM glucose, 15 mM HEPES, 1 mM ascorbic acid (an antioxidant), and 0.5 nM pargyline (a monoamine oxidase inhibitor). The cultures were then incubated with 0.25 ml of fresh uptake buffer containing 50 nM [$^3$H]DA (NEN/DuPont) for 20 min at 37° C. [$^3$H]DA uptake was stopped by removing the incubation mixture, and cells were then washed twice with 0.5 ml of the uptake buffer at room temperature. To release [$^3$H]DA from the cells, the cultures were lysed with 0.2 ml of 0.1 N NaOH for 1 h at room temperature, the lysate was then added to 1 ml of Microscint-20 (Packard 6013621), and counted for radioactivity in a microplate scintillation counter (Packard TopCount, NXT). Background values were obtained by adding to the uptake buffer 0.5 mM GBR-12909, a specific inhibitor of the high-affinity uptake pump of the dopaminergic neurons, and were usually <5% of the $^3$H uptake in untreated control cultures. Forskolin (Fk, 25 µM) was employed as a positive control.

Immunocytochemistry

The primary antibodies were: anti-TH monoclonal (1:400, Boehringer-Mannheim); anti-GFAP polyclonal (1:200, DAKO); anti-NSE polyclonal (1:2000, Polysciences Inc.); anti-tryptophan hydroxylase polyclonal (TPH) (1:500, Eugene Tech) and anti-islet-1 monoclonal (1:100, Developmental Studies Hybridoma Bank). Cultures were fixed with 4% paraformaldehyde in phosphate buffered saline (PBS), blocked with 3% bovine serum albumin plus 3% normal goat serum and permeabilized w/0.5% Triton in PBS. The primary antibodies were diluted in PBS containing 3% BSA and 0.4% Triton. Cells were visualized with the peroxidase-coupled avidin-biotin staining Vectastain ABC kit (Vector labs). Process-bearing TH-positive cells were counted at 100× magnification in consecutive fields covering the whole 16-mm-diameter culture well. GFAP-positive cells were counted in half the culture well. NSE-positive cells were counted in 3 photographed fields.

Serotonin (5-HT) and γ-Aminobutyric Acid (GABA) Uptake Assays

Cells were incubated and treated as for measuring [$^3$H]DA uptake with the following exceptions. For measuring serotonin uptake, [$^3$H]DA was replaced with 50 nM [$^3$H]serotonin (Amersham), and background values were obtained by adding 10 µM citalopram (a specific inhibitor of neuronal serotonin uptake). Fot measuring GABA uptake, the uptake buffer consists of HBSS (Gibco 11201-092) containing 5.6 mM glucose and was supplemented with 1.3 mM EDTA, 10 µM aminooxyacetic acid (a transaminase inhibitor to prevent GABA decomposition), 2 mM β-alanine (to inhibit glial uptake of GABA) and 0.1 µM [$^{14}$C]GABA (NEN/DuPont). Background values were obtained by adding 1 mM diaminobutyric acid, a specific inhibitor of neuronal GABA uptake. FBS (2%) was added as a positive control.

Staining for Apoptotic DA Neurons

To measure the percent of DA neurons undergoing apoptosis after different treatments, DIV-13 cultures (which were medium changed twice on DIV 5 and 9) were first stained with an anti-TH antibody and with FITC-conjugated goat anti-mouse secondary antibody (1:200, Jackson Lab) for 1 h at room temperature to label DA neurons. Cultures were then incubated with the fluorescent DNA dye Hoechst 33258 (Sigma), at 4 µg/ml for 5 min at room temperature, to visualize nuclear morphology. Cells were viewed under an inverted fluorescence microscope (Olympus) equipped with appropriate filters. Healthy and apoptotic TH$^+$ cells TH$^+$ cell numbers were counted in the entire area of each well by an observer who is blinded to the treatment.

Statistical Analysis

Data are expressed as the means±SD. All experiments were repeated at least two times. Data were analyzed by ANOVA, and the significance of intergroup differences was determined by Student's t-test (two-tailed). For multiple comparisons, ANOVA followed by post hoc Dunnett's test was performed. Differences at p<0.05 were considered significant.

Results

Identification of a Dopaminotrophic Small Molecule

Figure 32A:
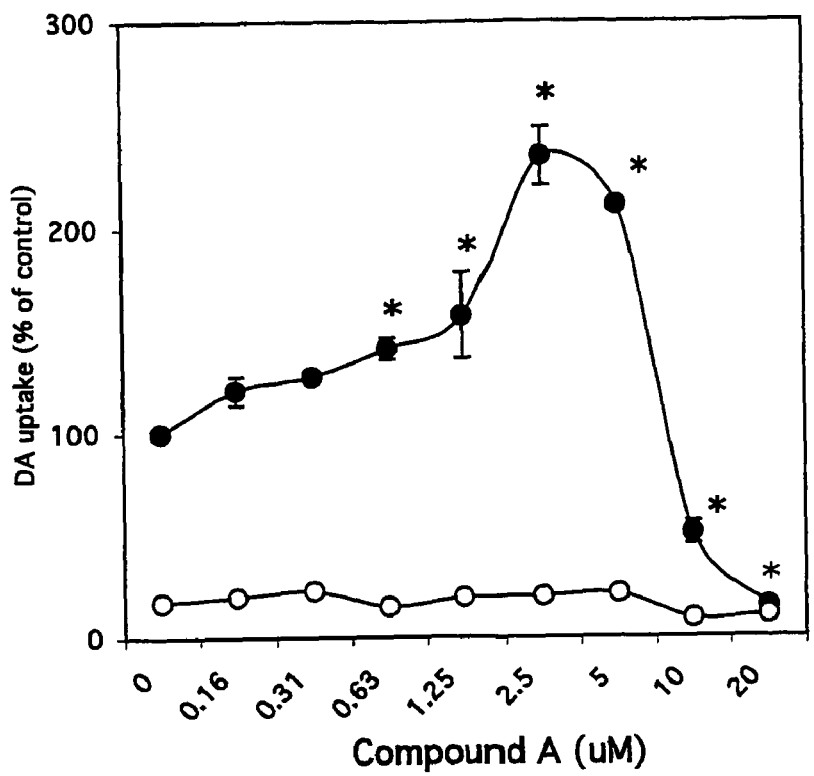
FIG. 32 shows the effects of compound A in midbrain cultures. All treatments were initiated at the time of plating. (A) Compound A stimulates dopamine (DA) uptake in a dose-dependent manner. DA uptake was measured at 7 days in vitro (DIV) in the absence (●) or presence (o) of 10 µM GBR-12909. (B) Compound A promotes survival of $TH^+$ neurons. Cultures were immunostained for TH at DIV 7 (●) or DIV 12 (o). *$p<0.05$, compared to corresponding untreated control, Student's t test. All data represent the average with standard deviation (SD) shown in error bars. In some instances, SDs are within the area of the symbols.

Various natural product/small molecule libraries were tested in the dopamine uptake assay above to identify a neurotrophic activity for midbrain dopaminergic neurons. Dopamine uptake measures the number and activity of specific dopamine reuptake transporters and reflects the functional differentiation of the dopaminergic neurons. Out of over 10,000 compounds tested, we identified one, compound A, that reproducibly stimulated DA uptake. The effect of compound A was dose-dependent with a maximal effect at around 2.5 µM (FIG. 32A). Inclusion of the DA transporter inhibitor GBR-12909 abolished uptake, verifying that the observed uptake was specific to DA neurons, without effects on noradrenergic neurons, glial cells, or nonspecific absorption. At concentrations above 10 µM, compound A was toxic and hence decreased DA uptake.

Figure 32B:
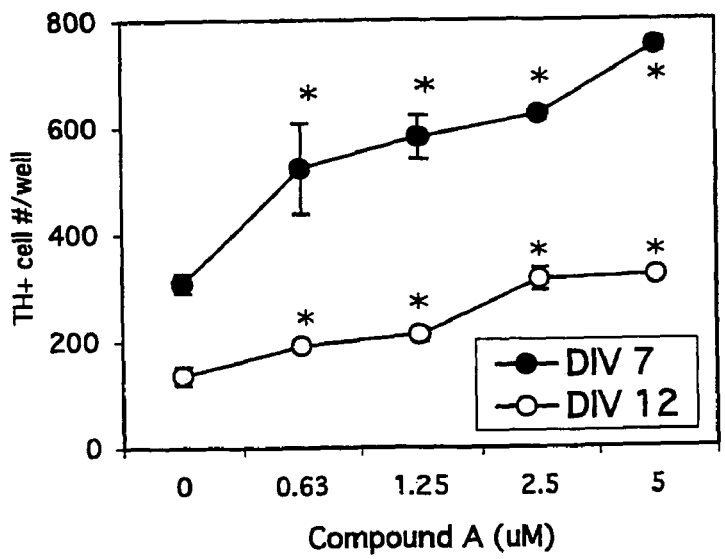

The percent stimulation by compound A remained about the same between DIV 5 and 7 (data not shown). In different experiments, the maximal stimulation by compound A on DIV 6 varied between 180-280%, comparable to that of GDNF in this assay (Lin et al. *J Biol Chem* 1994, 265, 8942-8947). Compound A upregulated tyrosine hydroxylase (TH) immunoreactivity in mesencephalic cultures. More significantly, the number of TH positive neurons, a plausible index for dopaminergic neuron survival, also was increased by compound A dose-dependently in the same concentration range that it increased DA uptake (FIG. 32B). Adding 2.5-5 µM of compound A once at the time of plating resulted in about twice as many DA neurons at either day 7 or day 12. Consistent with these findings, TH enzyme and protein were elevated following compound A treatment (data not shown).

Specificity

The effect of compound A in the midbrain culture appeared rather selective for dopaminergic neurons relative to neurons generally, because visual inspection of compound A-treated cultures by phase-contrast microscopy did not reveal an obvious difference from control cultures with respect to neuronal density. Because TH-positive neurons make up only ~0.4% of the total population, an increase in their number in the presence of compound A would not significantly affect the number of phase-contrast-bright cells. The visual observation was confirmed by total neuron immunocytochemical staining for neuron-specific enolase (NSE). NSE-positive cell numbers in the compound A-treated wells were indistinguishable from the non-treated control wells (FIG. 33A).

Compound A did not increase the density of astrocytes nor their expression of GFAP in the midbrain cultures. GFAP-positive cell numbers was not affected with the compound A treatment (FIG. 33B). Moreover, CUR-162590 had little, if any, effect on GABA-containing or serotonergic neurons, the two most abundant neuronal populations in the midbrain cultures. Neither GABA (FIG. 33C) nor serotonin (FIG. 33D) uptake was significantly affected by compound A in the concentration range that increased DA uptake. These data suggest that compound A acts directly and specifically on TH$^+$ neurons.

Since the aforementioned bioactivities are reminiscent of those of GDNF (Lin et al. *J Biol Chem* 1994, 265, 8942-8947), and since GDNF also increases the number of cranial motoneurons in these midbrain cultures (Zurn et al. *Neuroreport* 1994, 6, 113-118), we looked for this specific class of neurons using antibody directed against islet-1 (Ericson et al. *Science* 1992, 256, 1555-1560). Compound A produced a small but significant, (115-150% of control) increase in the number of islet-1$^+$ motoneurons which constitute only ~0.2% of the cells plated in the culture (FIG. 33E). Thus, like GDNF, compound A promotes the survival of both DA neurons and cranial motoneurons that, combined, account for <1% of the cells in these cultures.

The relative specificity of compound A in midbrain dopaminergic neurons was further investigated in the embryonic hindbrain culture where raphe nucleus containing the major serotonergic neurons reside. Compound A did not promote the survival of neurons immunoreactive for the key serotonin-synthesizing enzyme TPH (FIG. 33F), nor did it increase serotonin uptake in the hindbrain culture at concentrations necessary for increasing dopamine uptake in the midbrain culture (FIG. 33G). At 10 μM, compound A showed cytotoxicity on the hindbrain culture, as reflected in the inhibition of serotonin uptake, just as that observed in the midbrain culture in which compound A above 10 μM inhibited the dopamine uptake.

Figure 34A:
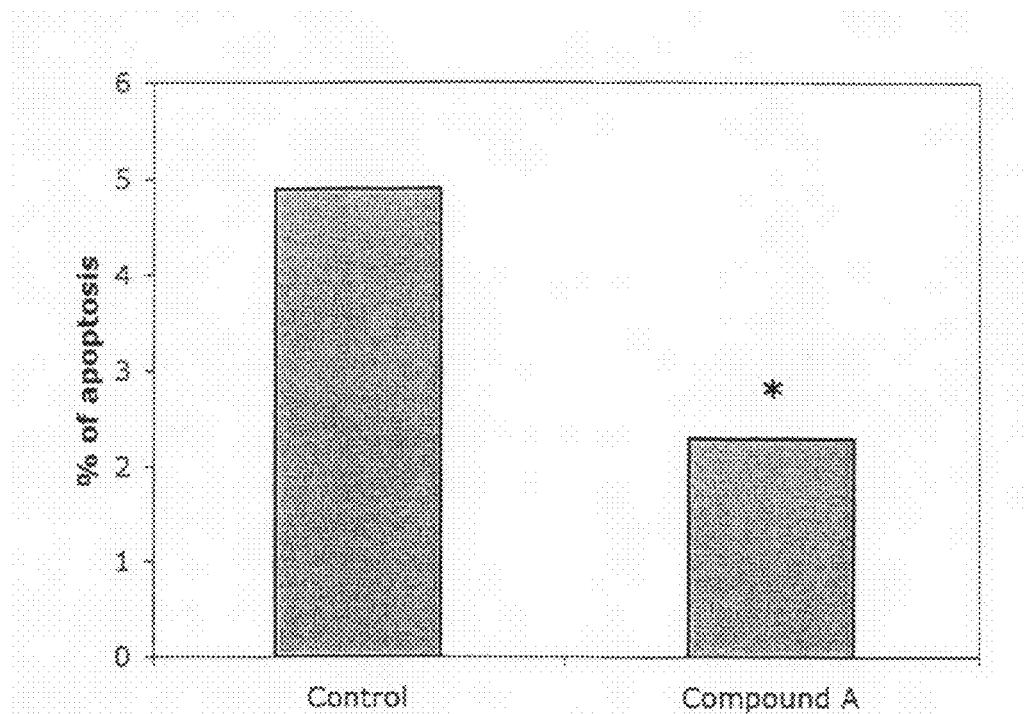
FIG. 34 depicts mechanism of compound A effect in midbrain cultures. 2.5 µM compound A was added at the time of plating. (A) Compound A reduces the rate of apoptosis of TH-positive cells. *$p<0.05$ versus Con, Student's t test. (B) Compound A protects TH-positive cells from $MPP^+$ induced neurotoxicity. Cultures at DIV 4 were treated with 2 µM $MPP^+$ (open bars) for 36 hrs, and processed for TH staining. *$p<0.05$ versus corresponding cultures not treated with $MPP^+$ (solid bars). #$p<0.05$ versus corresponding cultures without Compound A, Student's t test. Data represent averages (n=3) with SD shown in error bars.

Effect of compound A on DA neuron apoptosis. To explore the mechanism by which Compound A promotes DA neuron survival, we compared the amount of apoptosis of $TH^+$ cells in cultures with and without compound A treatment. We identified apoptotic $TH^+$ cells by the appearance of fragmented nuclei containing condensed chromatin as revealed by Hoechst dye (Clarkson et al. *Neuroport* 1995, 7, 145-149; Burke et al. *J Neurochem* 1998, 71, 517-525). We found that treatment with compound A reduced the rate of apoptosis by about 50% (FIG. 34A). Hence, the effect of compound A in enhancing DA neuron survival is mediated, at least in part, by a reduction in apoptotic cell death.

Figure 34B:
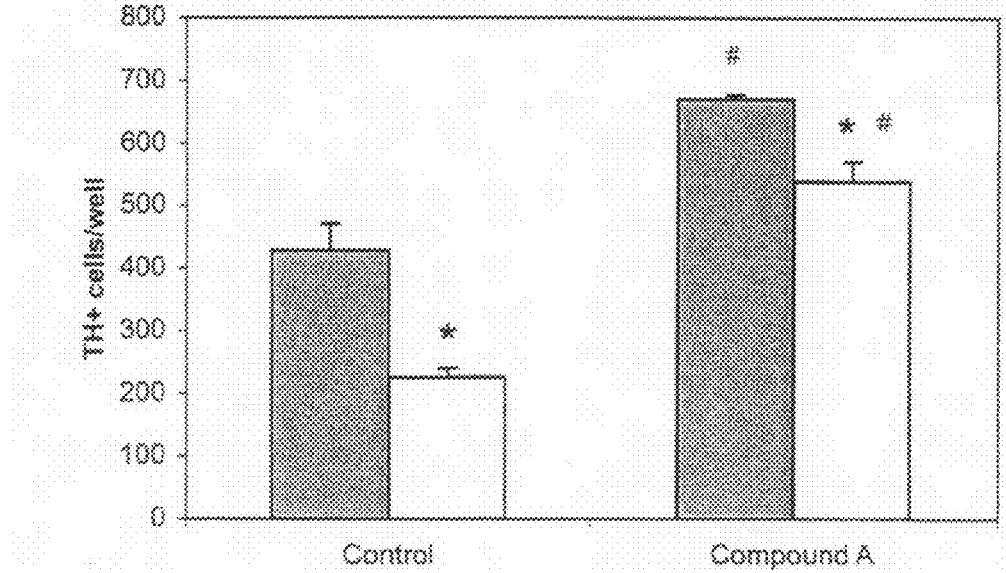
Figure 35:
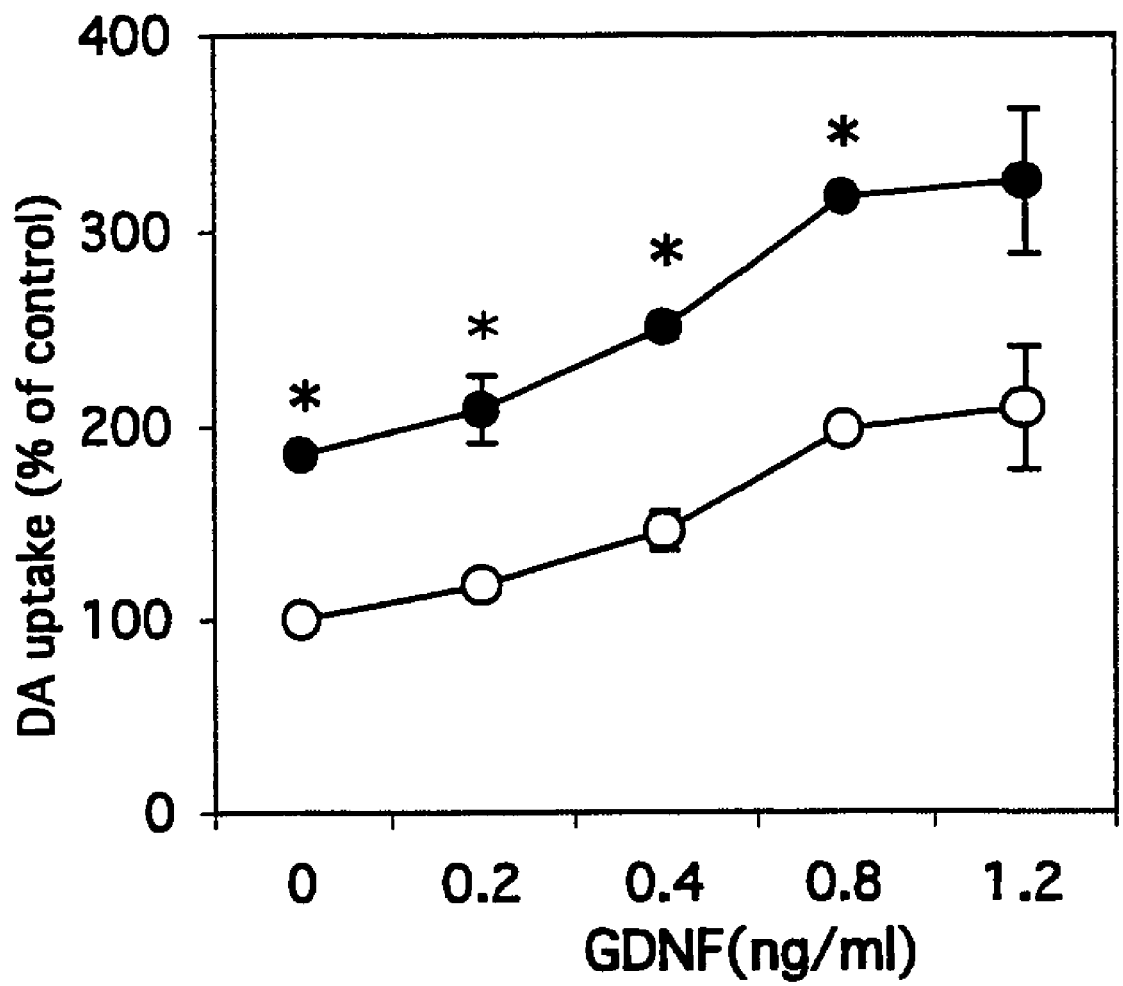
FIG. 35 depicts the additive effect of conjoint administration of compound A with GDNF. Cells were treated with GDNF in the absence (o) or presence (●) of 2.5 µM compound A. Each data point is the average of duplicate assays. Data represent percent of untreated control. *$p<0.05$ compared to corresponding GDNF alone treatment, Student's t test.

Compound A and cell death induced by toxin treatment. Toxins and free radicals have been implicated in the cell loss that occurs in PD (Gerlach and Riederer, *J Neural Transm* 1996, 103, 987-1041). Midbrain DA neurons are selectively vulnerable to MPTP (Mytilineou and Cohen, *Science* 1984, 225, 529-531), a neurotoxin that can cause the acute onset of Parkinsonian symptoms in both humans and animals (Langston et al. *Science* 1983, 219, 979-980; Heikkila et al. *Science* 1984, 225, 1451-1453). Having shown that compound A increases the survival of cultured DA neurons, we investigated whether compound A could also reduce the susceptibility of these neurons to $MPP^+$, the active metabolite of MPTP. Exposure of control cultures to 2 μM $MPP^+$ for 36 h destroyed 48% of the $TH^+$ neurons. However, the neuronal loss was reduced to 20% in compound A-treated cultures (FIG. 34B). compound A mostly prevented this loss (Fig. These data indicate that compound A protects DA neurons them from neurotoxin-induced degeneration.

Structurally Related Compounds

Several compounds (Compounds B-B") which are structurally similar to that of compound A were found to stimulate dopamine uptake in the midbrain culture. The stimulation was dose dependent between 2.5 and 20 μM. The activity profiles of three active analogues are shown in FIG. 36: compound X' and compound Y' showed no cytotoxicity even at 20 μM, compound Z' showed a higher stimulation maximum, and all three had lower half-maximal effective concentrations (EC50) of about 0.2 μM. These observations suggest that compound A may represent a prototype of a class of molecules that can be optimized via medicinal chemistry to get a pharmacologically desirable drug to treat certain neurodegenerative diseases such as PD.

Additive/Synergistic Effect of Compound A and GDNF

Since the GDNF effect on DA uptake plateaus around 1 ng/ml (Lin et al. Science 1993, 260, 1130-1132; Lin et al. *J. Neurochem* 1994, 63, 758-768), we added 2.5 μM compound A to increasing concentrations of GDNF. The addition of compound A to a maximally effective concentration of GDNF increased DA uptake above that reached by either GDNF or compound A alone (FIG. 37). The combined effect is at least as potent as that of forskolin, a cAMP stimulator used as positive control in the assay. Potentially, conjoint administration of compound A (or other subject compounds) with GDNF (or related factors) may provide an effective therapy for treating Parkinson's disease, allowing each compound to be administered in a lower dose in combination than would be required for either alone, thereby reducing any undesirable side effects that may be associated with dosing either compound at the therapeutic dose required for administration alone.

All of the above-cited references and publications are hereby incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A kit for treating a disorder characterized by loss of dopaminergic and/or motoneurons, or for treating Parkinson's disease, or amyotrophic lateral sclerosis (ALS), or limiting damage to neuronal cells by Parkinsonian conditions, in a patient, comprising one of the following compounds and a pharmaceutically acceptable carrier:

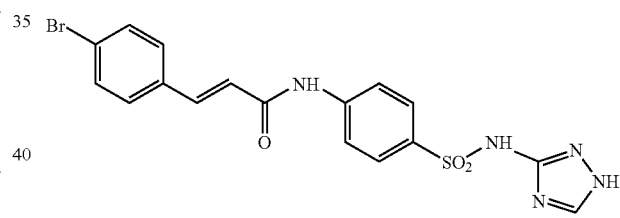

Compound X'

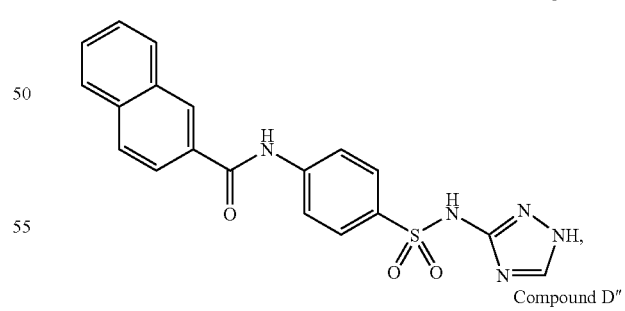

Compound Y'

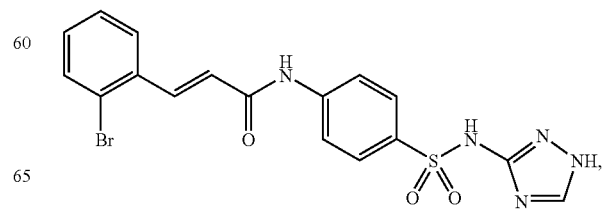

Compound D"

-continued
Compound E″
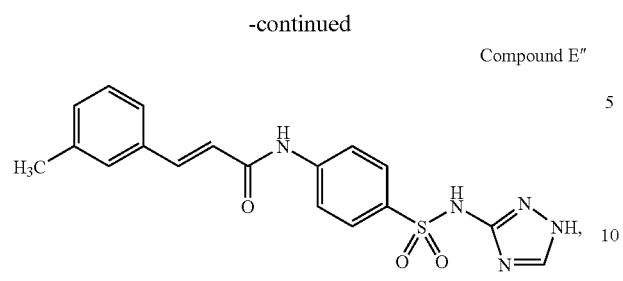
Compound R‴′
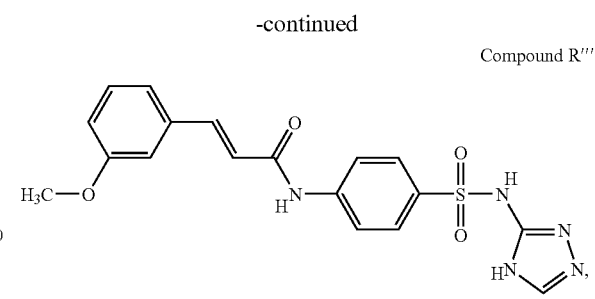
Compound G″
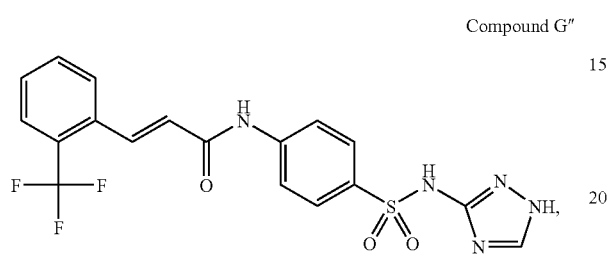
Compound S‴′
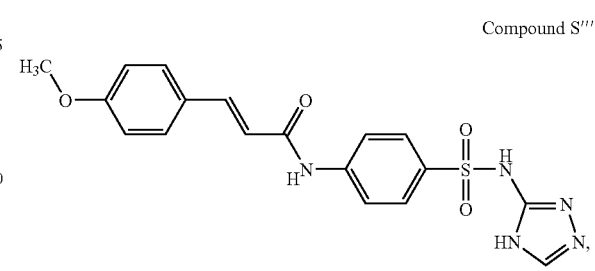
Compound H″
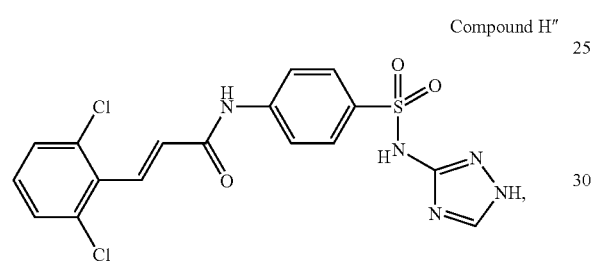
Compound X‴′
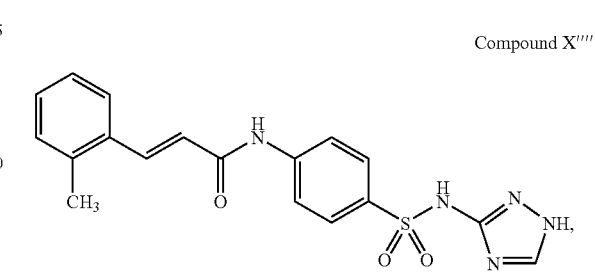
Compound R‴
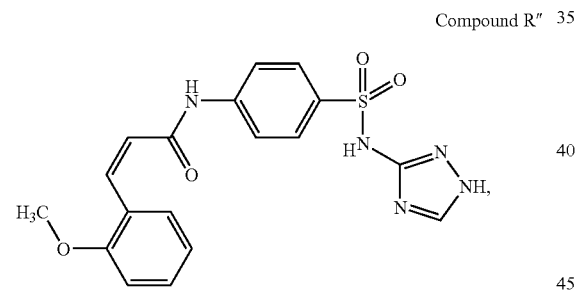
Compound A‴″
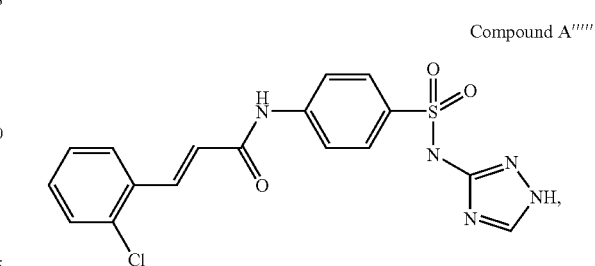
Compound S‴
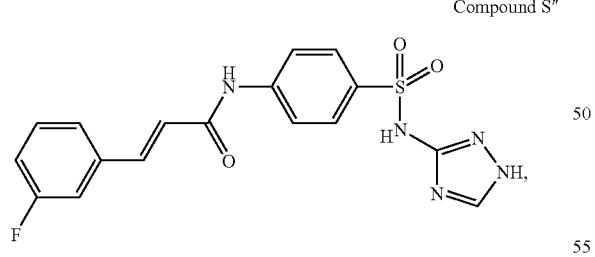
Compound B‴″
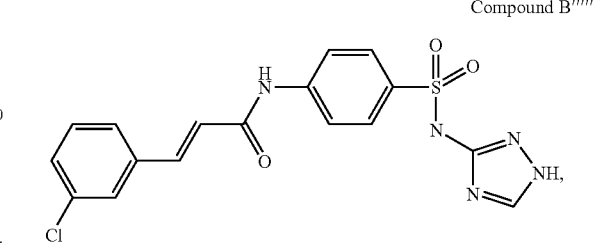
Compound Q‴
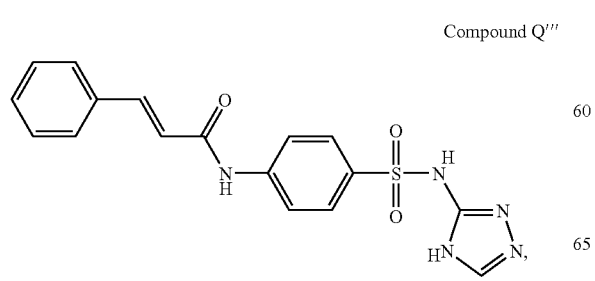
Compound W‴′
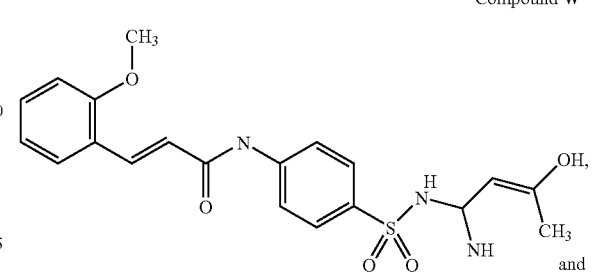
and Compound X'''

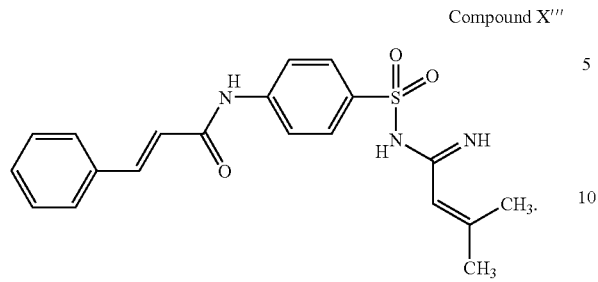

2. A kit for treating a disorder characterized by loss of dopaminergic and/or motoneurons, or for treating Parkinson's disease, or amyotrophic lateral sclerosis (ALS), or limiting damage to neuronal cells by Parkinsonian conditions, in a patient, comprising one of the following compounds and a pharmaceutically acceptable carrier:

Compound I'

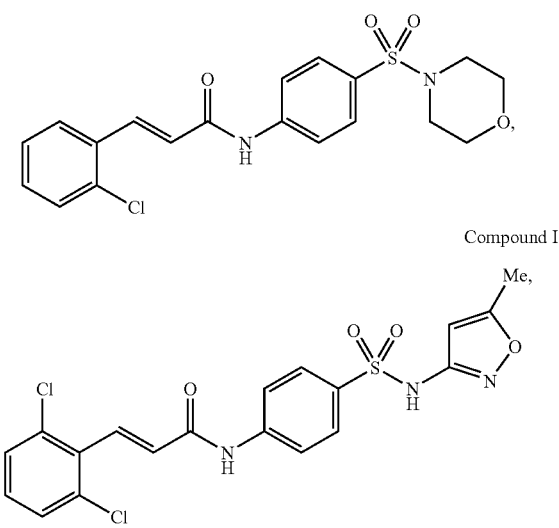

Compound I

Compound G

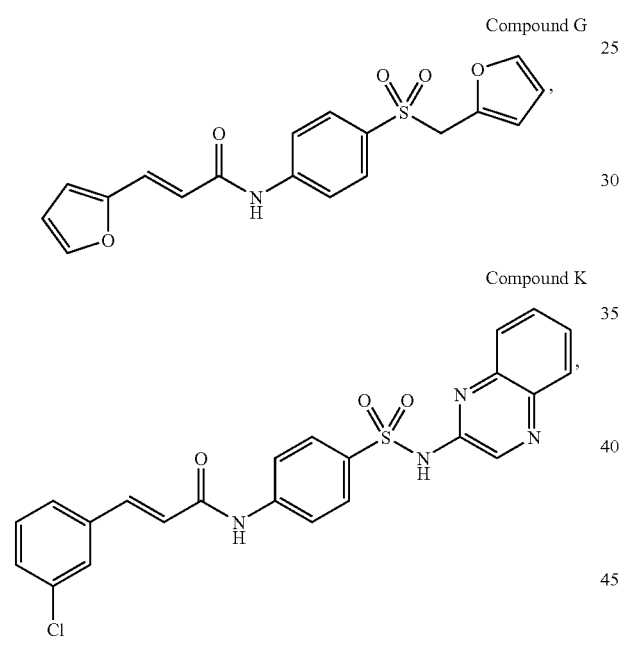

Compound G'

Compound K

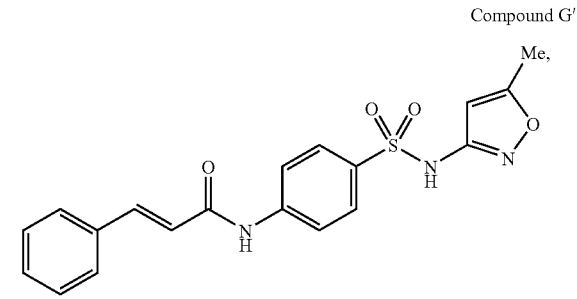

Compound B"

Compound K'

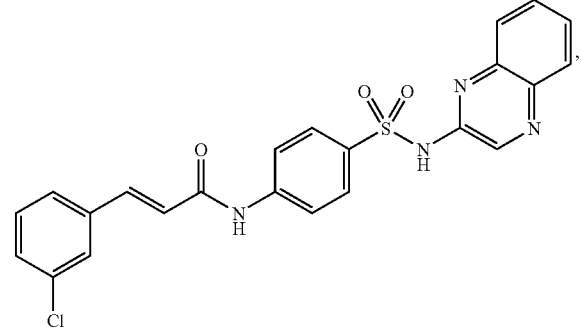

Compound J'

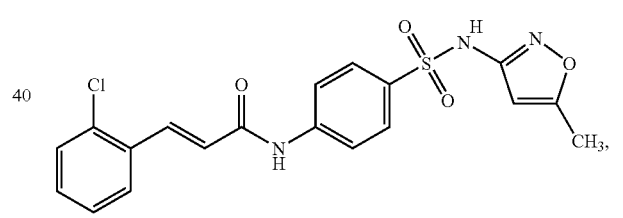
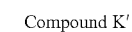

Compound M'

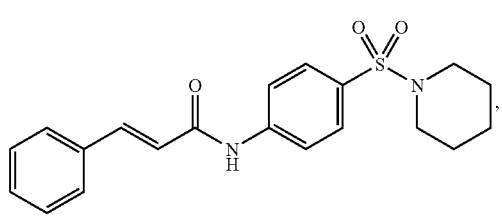

Compound L'

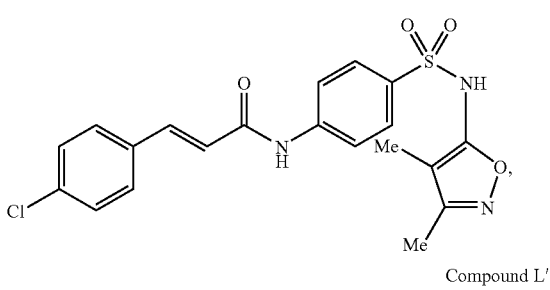

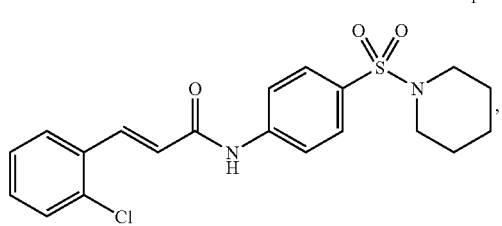
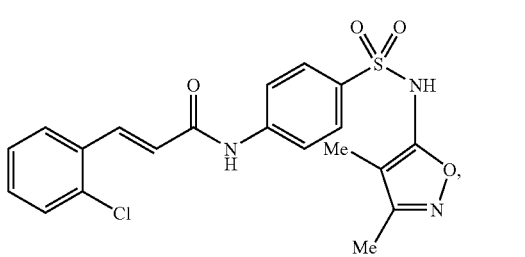

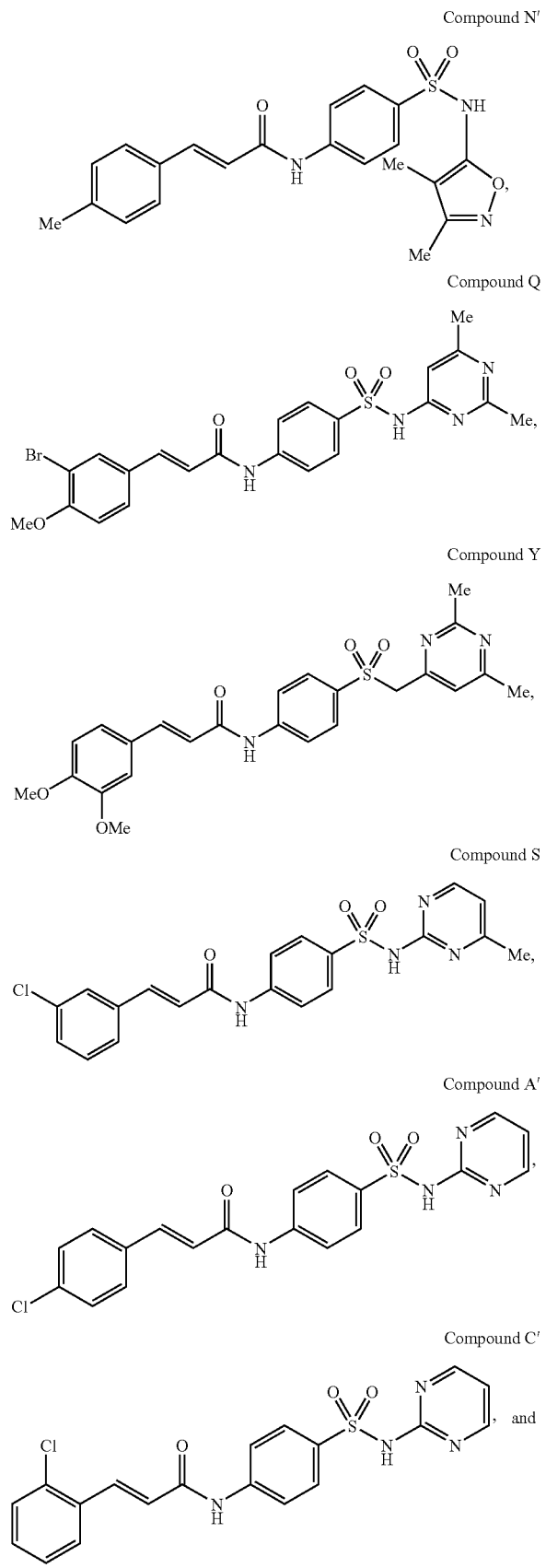
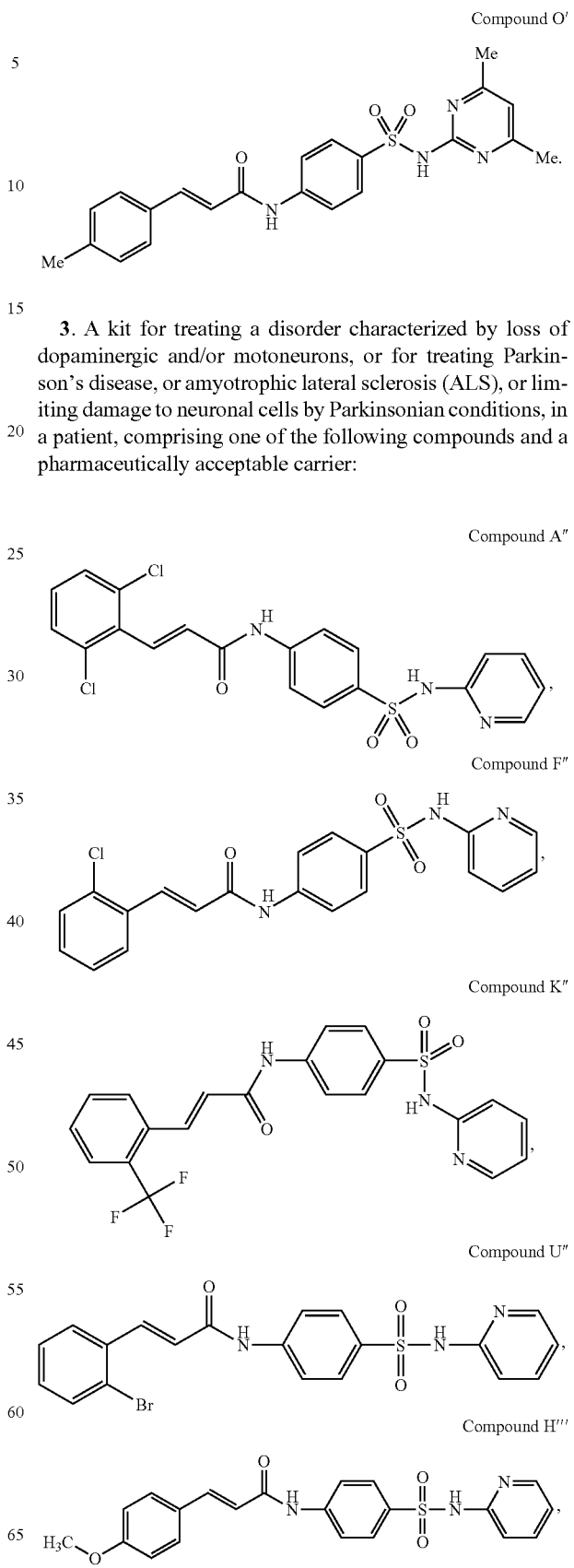
3. A kit for treating a disorder characterized by loss of dopaminergic and/or motoneurons, or for treating Parkinson's disease, or amyotrophic lateral sclerosis (ALS), or limiting damage to neuronal cells by Parkinsonian conditions, in a patient, comprising one of the following compounds and a pharmaceutically acceptable carrier:

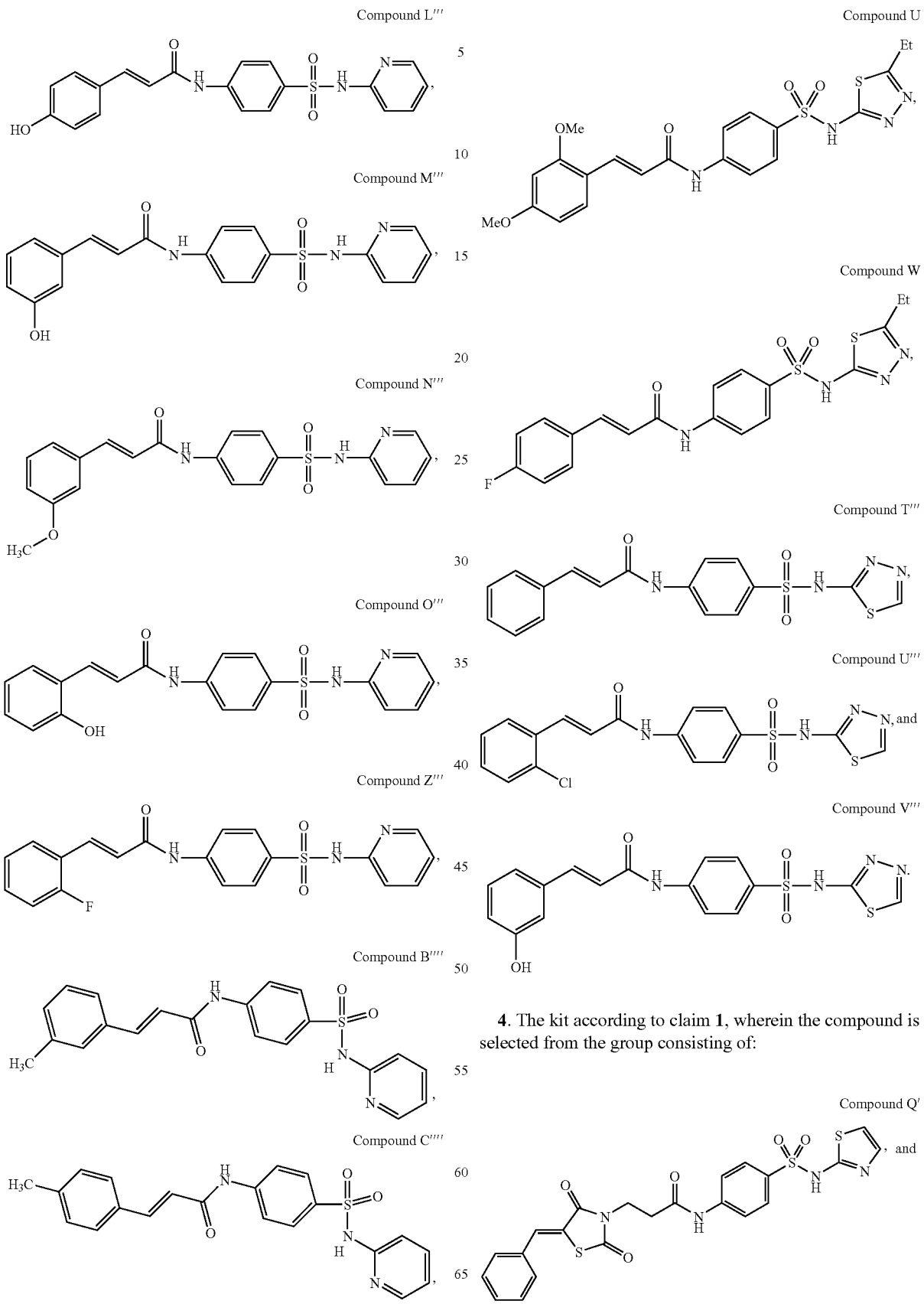
4. The kit according to claim 1, wherein the compound is selected from the group consisting of:

Compound R'

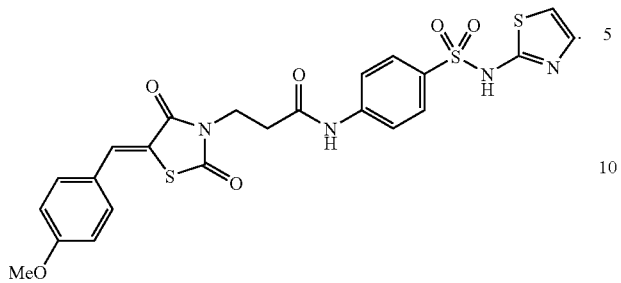

5. The kit according to claim 1, wherein the compound is

Compound A

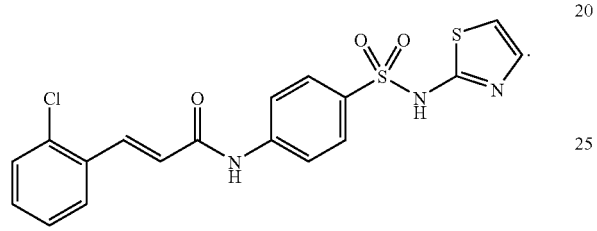

6. The kit according to claim 1, wherein the compound is selected from the group consisting of:

Compound W''''

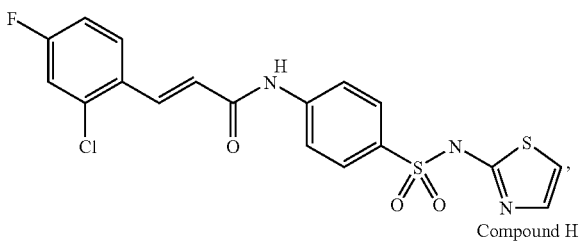

Compound H

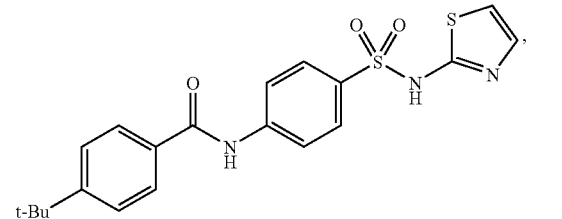

Compound O''''

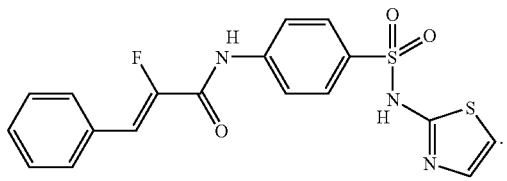

7. The kit according to claim 1, wherein the compound is

Compound Z

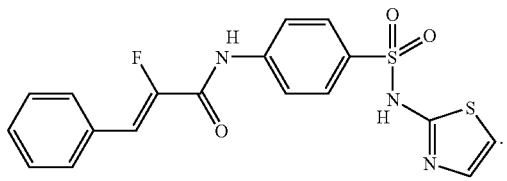

8. The kit according to claim 1, wherein the disease is schizophrenia, diabetic neuropathies, or immune-mediated neuropathies.

9. The kit according to claim 2, wherein the disease is schizophrenia, diabetic neuropathies, or immune-mediated neuropathies.

10. The kit according to claim 3, wherein the disease is schizophrenia, diabetic neuropathies, or immune-mediated neuropathies.

11. The kit according to claim 4, wherein the disease is schizophrenia, diabetic neuropathies, or immune-mediated neuropathies.

12. The kit according to claim 5, wherein the disease is schizophrenia, diabetic neuropathies, or immune-mediated neuropathies.

13. The kit according to claim 6, wherein the disease is schizophrenia, diabetic neuropathies, or immune-mediated neuropathies.

14. The kit according to claim 7, wherein the disease is schizophrenia, diabetic neuropathies, or immune-mediated neuropathies.

* * * * *